(12) United States Patent
Huang

(10) Patent No.: US 10,711,275 B2
(45) Date of Patent: Jul. 14, 2020

(54) METHODS AND COMPOSITIONS FOR INTERFERENCE WITH DNA POLYMERASE AND DNA SYNTHESIS

(71) Applicant: Georgia State University Research Foundation, Inc., Atlanta, GA (US)

(72) Inventor: Zhen Huang, Marietta, GA (US)

(73) Assignee: Zhen Huang, Marietta, GA (US)

( * ) Notice: Subject to any disclaimer, the term of this patent is extended or adjusted under 35 U.S.C. 154(b) by 536 days.

(21) Appl. No.: 14/903,682

(22) PCT Filed: Jul. 11, 2014

(86) PCT No.: PCT/US2014/046275
§ 371 (c)(1),
(2) Date: Jan. 8, 2016

(87) PCT Pub. No.: WO2015/006641
PCT Pub. Date: Jan. 15, 2015

(65) Prior Publication Data
US 2016/0281093 A1    Sep. 29, 2016

Related U.S. Application Data

(60) Provisional application No. 61/845,793, filed on Jul. 12, 2013.

(51) Int. Cl.
*C12N 9/12* (2006.01)
*C12N 15/113* (2010.01)
*C12N 15/11* (2006.01)
*A61K 47/42* (2017.01)

(52) U.S. Cl.
CPC .......... *C12N 15/1137* (2013.01); *A61K 47/42* (2013.01); *C12N 9/1252* (2013.01); *C12N 15/11* (2013.01); *C12N 2310/14* (2013.01); *C12N 2310/18* (2013.01); *C12N 2320/30* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 5,219,740 A | 6/1993 | Miller | |
| 5,539,082 A | 7/1996 | Nielsen | |
| 5,714,331 A | 2/1998 | Buchardt | |
| 5,719,262 A | 2/1998 | Buchardt | |
| 6,177,542 B1 | 1/2001 | Ruoslahti | |
| 6,576,239 B1 | 6/2003 | Ruoslahti | |
| 2002/0055174 A1 | 5/2002 | Rittner | |
| 2002/0068272 A1 | 6/2002 | Larocca | |
| 2003/0003100 A1 | 1/2003 | Levy | |
| 2003/0083261 A1 | 5/2003 | Yu | |
| 2003/0125283 A1 | 7/2003 | Gatenby | |
| 2003/0166601 A1 | 9/2003 | Woodle | |
| 2005/0071088 A1 | 3/2005 | Landfield | |
| 2005/0147993 A1 | 7/2005 | Khan | |
| 2006/0061315 A1 | 3/2006 | Scaria | |
| 2006/0070133 A1 | 3/2006 | Dean | |
| 2006/0147922 A1 | 7/2006 | Watts | |
| 2006/0233807 A1 | 10/2006 | Svanborg | |
| 2006/0242725 A1 | 10/2006 | Strong | |
| 2007/0212332 A1 | 9/2007 | Baylink | |
| 2007/0231862 A1 | 10/2007 | Diamond | |
| 2009/0087899 A1 | 4/2009 | McKnight | |
| 2009/0176710 A1 | 7/2009 | Hadwiger | |
| 2009/0257951 A1 | 10/2009 | Ruoslahti | |
| 2009/0305329 A1 | 12/2009 | Szllak | |
| 2010/0099627 A1 | 4/2010 | Seger | |
| 2010/0143454 A1 | 6/2010 | McLinden | |
| 2010/0322862 A1 | 12/2010 | Ruoslahti | |

FOREIGN PATENT DOCUMENTS

| | | |
|---|---|---|
| WO | 9007936 | 7/1990 |
| WO | 9102805 | 3/1991 |
| WO | 9303769 | 3/1993 |
| WO | 9310218 | 5/1993 |
| WO | 9311230 | 6/1993 |
| WO | 9319191 | 9/1993 |
| WO | 9325234 | 12/1993 |

(Continued)

OTHER PUBLICATIONS

Davis et al., Molecular Pharmaceutics, 2009, vol. 6, pp. 659-668.*
Wang et al., Microbio and Molecular Bio Reviews, 2004, vol. 68, pp. 432-452.*
Doi et al., Current Biology, 2003, vol. 13, pp. 41-46.*
Davis, Molecular Pharmaceutics, 2009, vol. 6, pp. 659-668.*
Karpala et al., Immunology and Cell Biology, 2005, vol. 83, pp. 211-216.*
Agmon, "The dimeric proto-ribosome: Structural details and possible implications on the origin of life", Int J Mol Sci., 10:2921-34 (2009).
Brewis et al.; "Particle assembly incorporating a VP22-BH3 fusion protein, facilitating intracellular delivery, regulated release, and apoptosis", Mol. Ther. 7, 262-270 (2003).
Bucci, et al., "In vivo delivery of the caveolin-1 scaffolding domain inhibits nitric oxide synthesis and reduces inflamation", Nat. Med., 6:1362-7 (2000).

(Continued)

*Primary Examiner* — Mindy G Brown
(74) *Attorney, Agent, or Firm* — Pabst Patent Group LLP

(57) ABSTRACT

Disclosed are methods and compositions for inhibiting DNA synthesis in a cell using RNA. Inhibition of DNA synthesis by RNA can be used, for example, in analytical methods, as a research tool to affect cells under study, to synchronize cell cycle in a cell culture, and to inhibit cell growth. For example, inhibition of DNA synthesis in cancer cells can be used to inhibit cancer cells and treat cancer. The RNA can be any RNA, such as whole cell RNA, whole cell mRNA, whole cell ribosomal RNA, whole cell transfer RNA, synthetic RNA, recombinant RNA, modified RNA, or a combination. The composition can comprise RNA and a pharmaceutically acceptable carrier or RNA, a targeting molecule, and a pharmaceutically acceptable carrier. The targeting molecule can be a tumor-targeting peptide.

13 Claims, 2 Drawing Sheets

Specification includes a Sequence Listing.

(56) References Cited

FOREIGN PATENT DOCUMENTS

| WO | 9325698 | 12/1993 | | |
|---|---|---|---|---|
| WO | 9403622 | 2/1994 | | |
| WO | 9412649 | 6/1994 | | |
| WO | 9428938 | 12/1994 | | |
| WO | 9500655 | 1/1995 | | |
| WO | 9511984 | 5/1995 | | |
| WO | WO-2009136291 | A2 * | 11/2009 | ............ A61Q 19/08 |

OTHER PUBLICATIONS

Carrasco, et al., "Selenium derivatization and crystallization of DNA and RNA oligonucleotides for X-ray crystallography using multiple anomalous dispersion", Nucleic Acids Res., 32:1638-46 (2004).
Chabes and Stillman "Constitutively high dNTP concentration inhibits cell cycle progression and the DNA damage checkpoint in yeast *Saccharomyces cerevisiae*", PNAS, 104:1183-8 (2007).
Cheah, et al., "Control of alternative RNA splicing and gene expression by eukaryotic riboswitches", Nature, 447:497-500 (2007).
Davis, et al., "The first targeted delivery of snRNA in humans viâ a self-assembling, cyclodextrin polymer-based nanoparticle: from concept to clinic", Mol Pharm, 6(3):659-68 (2009).
Derossi, et al., "Trojan peptides: the penetratin system for intracellular delivery", Trends Cell Biol., 8:84-7 (1998).
Derossi, et al., "The third helix of the Antennapedia homeodomain translocates through biological membranes", Biol.Chem. 269, 10444-50 (1994).
Elledge and Davis, "Two genes differentially regulated in the cell cycle and by DNA-damaging agents encode alternative regulatory subunits of ribonucleotide reductase", Genes Dev., 4:740-51 (1990).
Elliott and O\Hare, "Intercellular trafficking and protein delivery by a herpesvirus structural protein", Cell, 88(2):223-33 (1997).
Elmquist, et al.. "VE-cadherin-derived cell-penetrating peptide, pVEC, with carrier functions", Exp. Cell Res., 269:237-44 (2001).
Fire, et al., "Potent and specific genetic interference by double-stranded RNA in Caenorhabditis elegane", Nature, 391:806-11 (1998).
Fischer, et al., "Structure-activity relationship of truncated and substituted analogues of the intracellular delivery vector Penetratin", J. Pept. Res., 55:163-72 (2000).
Fox, et al., "An exit cavity was crucial to the polymerase activity of the early ribosome", Astrobiology, 12:57-60 (2012).
Frankel and Pabo, "Cellular uptake of the tat protein from human immunodeficiency virus", Cell, 55:1189-93 (1988).
Freemont, et al., "Cocrystal structure of an editing complex of Klenow fragment with DNA", PNAS, 85:8924-8 (1988).
Gao, et al., "A cell-penetrating peptide from a novel pVII-pIX phage-displayed random peptide library", Bioorg, Med. Chem., 10:4057-65 (2002).
Gening, et al., "RNA aptamers selected against DNA polymerase beta inhibit the polymerase activities of DNA polymerases beta and kappa", Nucleic Acids Res., 34(9):2579-86 (2006).
Gesteland, et al., "The Nature of Modern RNA Suggests a Prebiotic RNA", The RNA World, 3rd ed. ,vol. (43), Cold Spring Harbor, NY,: Cold Spring Harbor Laboratory Press (2006).
Golosov, et al., "The mechanism of the translocation step in DNA replication by DNA polymerase I: a computer simulation analysis", Structure, 18:83-93 (2010).
Gon, et al., "Increase in dNTP pool size during the DNA damage response plays a key role in spontaneous and induced-mutagenesis in *Escherichia coli*", PNAS, 108:19311-6 (2011).
Green and Loewenstein, "Autonomous functional domains of chemically synthesized human immunodeficiency virus tat trans-activator protein", Cell, 55:1179-88 (1988).
Guo, et al., "Mammalian microRNAs predominantly act to decrease target mRNA: levels", Nature, 466:835-40 (2010).

Hamzah, et al., "Vascular targeting of anti-CD40 antibodies and IL-2 into autochthonous tumors enhances immunotherapy in mice", J. Clin. Invest., 118:1691-9 (2008).
Harms, et al., "High resolution structure of the large ribosomal subunit from a mesophilic eubacterium", Cell, 107:679-88 (2001).
Heo and Sung, "Vernalization-mediated epigenetic silencing by a long intronic noncoding RNA", Science, 331:76-9 (2011).
Hoffman, et al., "Progressive vascular changes in a transgenic mouse model of squamous cell carcinoma", Cancer Cell, 4(5):383-91. (2003).
Hong and Clayman, "Isolation of a peptide for targeted drug delivery into human head and neck solid tumors", Cancer Res., 60:6551-6 (2000).
Ji and Mathews, "Analysis of mutagenesis induced by a thermolabile T4 phage deoxycytidylate hydroxymethylase suggests localized deoxyribonucleotide pool imbalance", Mol Gen Genet., 226:257-64 (1991).
Joyce, et al., "Stage-specific vascular markers revealed by phage display in a mouse model of pancreatic islet tumorigenesis", Cancer Cell, 4:393-403 (2003).
Karmali, et al., "Targeting of albumin-embedded paclitaxel nanoparticles to tumors", Nanomedicine, 5:73-82 (2009).
Laakkonen, et al., "A tumor-homing peptide with a targeting specificity related to lymphatic vessels", Nature Med. 8:751-5 (2002).
Laakkonen, et al., "Antitumor activity of a homing peptide that targets tumor lymphatics and tumor cells", PNAS, 101:9381-6 (2004).
Lakhin, et al., "Isolation and characterization of high affinity aptamers against DNA polymerase iota", Nucleic Acid Therapeutics, 22(1):49-57 (2012).
Landon, et al., "Combinatorial discovery of tumor targeting peptides using phage display", J Cellular Biochem., 90(3):509-17 (2003).
Lin, et al., "Inhibition of nuclear translocation of transcription factor NF-kappa B by a synthetic peptide containing a cell membrane-permeable motif and nuclear localization sequence", J. Biol. Chem. 270, 14255-8 (1995).
Lundberg, et al., "Cell membrane translocation of the N-terminal (1-28) part of the prion protein", Biochem. Biophys. Res. Commun., 299:85-90 (2002).
Ma, et al., "Structural basis for 5'-end-specific recognition of guide RNA by the A. fulgidus Piwi protein", Nature, 434:666-70 (2005).
MacRae, et al., "Structural basis for double-stranded RNA processing by Dicer", Science, 311:195-8 (2006).
Mathews and Ji, "DNA precursor asymmetries, replication fidelity, and variable genome evolution", Bioessays., 14:295-301 (1992).
Mathews, "DNA precursor metabolism and genomic stability", FASEB J, 20:1300-14 (2006).
Meade and Dowdy, "Exogenous siRNA delivery using peptide transduction domains/cell penetrating peptides", Adv Drug Deliv Rev., 59(2-3):134-40 (2007).
Mello and Conte, "Revealing the world of RNA interference", Nature, 431:338-42 (2004).
Morris, et al., "A peptide carrier for the delivery of biologically active proteins into mammalian cells", Nature Biotechnol., 19:1173-6 (2001).
Nagano, et al., "The Air noncoding RNA epigenetically silences transcription by targeting G9a to chromatin", Science, 322:1717-20 (2008).
Nielsen, et al., "Sequence-selective recognition of DNA by strand displacement with a thymine-substituted polyamide", Science, 254:1497 1500 (1991).
Niida, et al., "Mechanisms of dNTP supply that play an essential role in maintaining genome integrity in eukaryotic cells", Cancer Sci., 101:2505-9 (2010).
Nishitani and Lygerou, "Control of DNA replication licensing in a cell cycle", Genes Cells, 7:523-534 (2002).
Nissen, et al., "The structural basis of ribosome activity in peptide bond synthesis", Science, 289:920-30 (2000).
Oehlke, et al. , "Cellular uptake of an alpha-helical amphipathic model peptide with the potential to deliver polar compounds into the cell interior non-endocytically", Biochim. Biophys. Acta., 1414:127-39 (1998).

(56) References Cited

OTHER PUBLICATIONS

Park, et al., "Structure-activity analysis of buforin II, a histone H2A-derived antimicrobial peptide: the proline hinge is responsible for the cell-penetrating ability of buforin II", PNAS, 97:8245-50 (2000).

Paulsson and Chattoraj, "Origin inactivation in bacterial DNA replication control", Mol Microbiol., 61:9-15 (2006).

Pooga, et al., "Cell penetration by transportan", FASEB J., 12:67-77 (1998).

Rampazzo, et al., "Regulation by degradation, a cellular defense against deoxyribonucleotide pool imbalances", Mutat Res., 703:2-10 (2010).

Rousselle, et al., "New advances in the transport of doxorubicin through the blood-brain barrier by a peptide vector-mediated strategy", Pharmacol. 57,679-86 (2000).

Ruoslahti, et al., "Targeting of drugs and nanoparticles to tumors", J. Cell Biology, (2010).

Savchenko, et al., "Molecular basis of the antimutagenic activity of the house-cleaning inosine triphosphate pyrophosphatase RdgB from *Escherichia coli*", J Mol Biol., 374:1091-1103 (2007).

Sudarsan, et al., "Tandem riboswitch architectures exhibit complex gene control functions", Science, 314:300-4 (2006).

Vigneron, et al., "Guanidinium-cholesterol cationic lipids: efficient vectors for the transfection of eukaryotic cells", PNAS, 93:9682-6 (1998).

Wiedenheft, et al., "RNA-guided genetic silencing systems in bacteria and archaea", Nature, 482:331-8 (2012).

Wowor, et al., "Thermodynamics of the DNA structural selectivity of the Pol I DNA polymerases from *Escherichia coli* and *Thermus aquaticus*", Biophys J., 98:3015-24 (2010).

Wu, et al., "Targeted Therapy for Cancer", J. Cancer Molecules, 2(2):57-66 (2006).

Zhao, et al., "A suppressor of two essential checkpoint genes identifies a novel protein that negatively affects dNTP pools", Mol Cell, 2:329-40 (1998).

Zorko and Langel, "Cell-penetrating peptides: mechanism and kinetics of cargo delivery", Adv Drug Deliv Rev., 57:629-45 (2005).

International Search Report for PCT application PCT/US2014/046275 dated Feb. 16, 2015.

\* cited by examiner

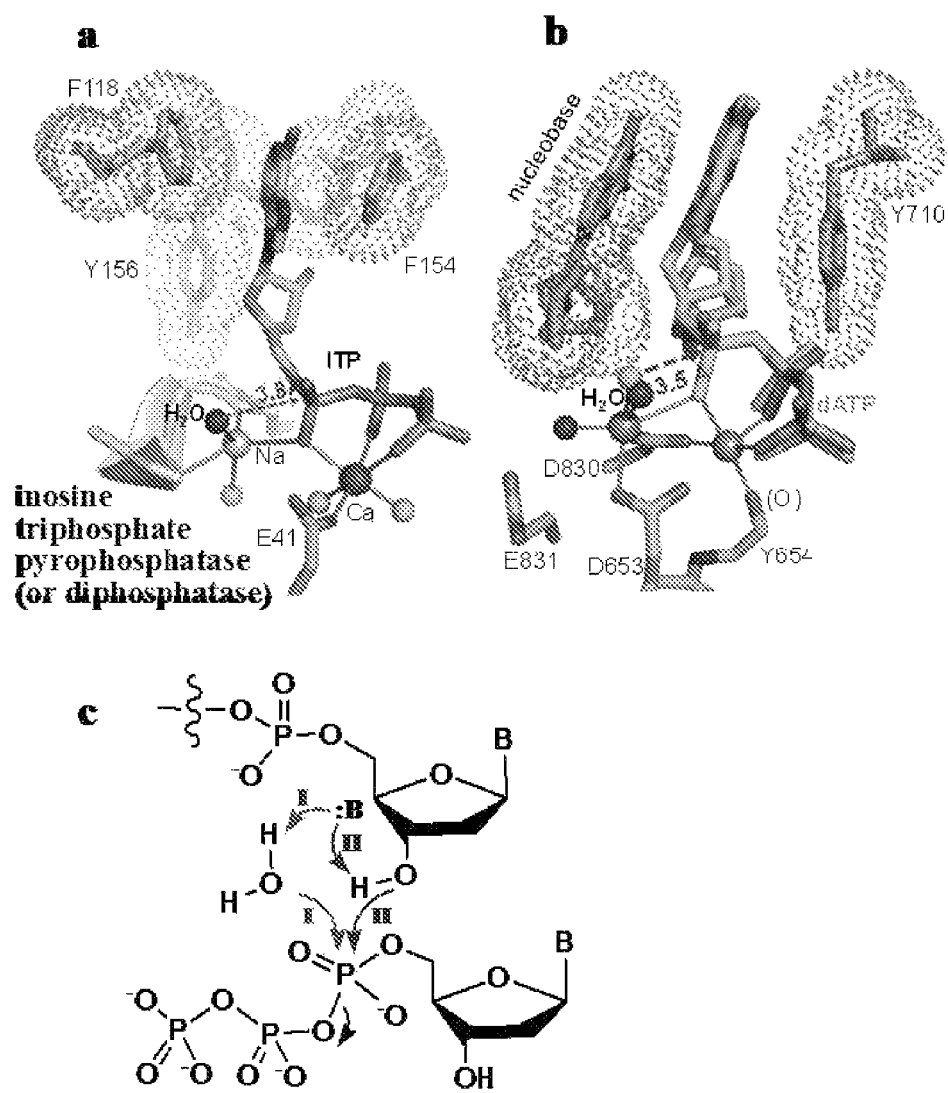
FIGS. 3A, 3B, and 3C

SEQUENCE LISTING

<160> NUMBER OF SEQ ID NOS: 186

<210> SEQ ID NO 1
<211> LENGTH: 12

```
<212> TYPE: RNA
<213> ORGANISM: Artificial Sequence
<220> FEATURE:
<223> OTHER INFORMATION: RNA Oligonucleotide

<400> SEQUENCE: 1
auccgaguca gg                                                              12

<210> SEQ ID NO 2
<211> LENGTH: 12
<212> TYPE: RNA
<213> ORGANISM: Artificial Sequence
<220> FEATURE:
<223> OTHER INFORMATION: RNA Oligonucleotide

<400> SEQUENCE: 2
ccugacucgg au                                                              12

<210> SEQ ID NO 3
<211> LENGTH: 18
<212> TYPE: RNA
<213> ORGANISM: Artificial Sequence
<220> FEATURE:
<223> OTHER INFORMATION: RNA Oligonucleotide

<400> SEQUENCE: 3
ucgacaucga caucgaca                                                        18

<210> SEQ ID NO 4
<211> LENGTH: 24
<212> TYPE: RNA
<213> ORGANISM: Artificial Sequence
<220> FEATURE:
<223> OTHER INFORMATION: RNA Oligonucleotide

<400> SEQUENCE: 4
ucgacaucga caucgacauc gaca                                                 24

<210> SEQ ID NO 5
<211> LENGTH: 24
<212> TYPE: RNA
<213> ORGANISM: Artificial Sequence
<220> FEATURE:
<223> OTHER INFORMATION: RNA Oligonucleotide

<400> SEQUENCE: 5 auggauug gcgauaaaaa acaa                                                   24

<210> SEQ ID NO 6
<211> LENGTH: 69
<212> TYPE: RNA
<213> ORGANISM: Artificial Sequence
<220> FEATURE:
<223> OTHER INFORMATION: RNA Oligonucleotide

<400> SEQUENCE: 6
gggagcccug ucaccggaug ugcuuuccgg ucugaugagu ccgugaggac aaaacagggc          60
ucccgaauu                                                                  69

<210> SEQ ID NO 7
<211> LENGTH: 55
<212> TYPE: DNA
<213> ORGANISM: Artificial Sequence
<220> FEATURE:
<223> OTHER INFORMATION: DNA Oligonucleotide
```

<400> SEQUENCE: 7

```
tgtacgtttc ggcctttcgg cctcatcagg ttgcctatag tgagtcgtat tacgc        55
```

<210> SEQ ID NO 8
<211> LENGTH: 21
<212> TYPE: DNA
<213> ORGANISM: Artificial Sequence
<220> FEATURE:
<223> OTHER INFORMATION: DNA Oligonucleotide

<400> SEQUENCE: 8

```
gcgtaatacg actcactata g                                            21
```

<210> SEQ ID NO 9
<211> LENGTH: 5
<212> TYPE: PRT
<213> ORGANISM: Artificial Sequence
<220> FEATURE:
<223> OTHER INFORMATION: Peptide

<400> SEQUENCE: 9

Cys Asn Gly Arg Cys
1               5

<210> SEQ ID NO 10
<211> LENGTH: 9
<212> TYPE: PRT
<213> ORGANISM: Artificial Sequence
<220> FEATURE:
<223> OTHER INFORMATION: Peptide

<400> SEQUENCE: 10

Cys Ser Arg Pro Arg Arg Ser Glu Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Peptide

<400> SEQUENCE: 11

Cys Ser Arg Pro Arg Arg Ser Val Cys
1               5

<210> SEQ ID NO 12
<211> LENGTH: 9
<212> TYPE: PRT
<213> ORGANISM: Artificial Sequence
<220> FEATURE:
<223> OTHER INFORMATION: Peptide

<400> SEQUENCE: 12

Cys Ser Arg Pro Arg Arg Ser Trp Cys
1               5

<210> SEQ ID NO 13
<211> LENGTH: 31
<212> TYPE: PRT
<213> ORGANISM: Artificial Sequence
<220> FEATURE:
<223> OTHER INFORMATION: Peptide

<400> SEQUENCE: 13

Lys Asp Glu Pro Gln Arg Arg Ser Ala Arg Leu Ser Ala Lys Pro Ala

```
               1               5                  10                  15
Pro Pro Lys Pro Glu Pro Lys Pro Lys Ala Pro Ala Lys Lys
            20                  25                  30
```

<210> SEQ ID NO 14
<211> LENGTH: 10
<212> TYPE: PRT
<213> ORGANISM: Artificial Sequence
<220> FEATURE:
<223> OTHER INFORMATION: Peptide

<400> SEQUENCE: 14

```
Pro Gln Arg Arg Ser Ala Arg Leu Ser Ala
1               5                   10
```

<210> SEQ ID NO 15
<211> LENGTH: 10
<212> TYPE: PRT
<213> ORGANISM: Artificial Sequence
<220> FEATURE:
<223> OTHER INFORMATION: Peptide

<400> SEQUENCE: 15

```
Pro Lys Arg Arg Ser Ala Arg Leu Ser Ala
1               5                   10
```

<210> SEQ ID NO 16
<211> LENGTH: 13
<212> TYPE: PRT
<213> ORGANISM: Artificial Sequence
<220> FEATURE:
<223> OTHER INFORMATION: Peptide

<400> SEQUENCE: 16

```
Cys Gly Arg Glu Cys Pro Arg Leu Cys Gln Ser Ser Cys
1               5                   10
```

<210> SEQ ID NO 17
<211> LENGTH: 13
<212> TYPE: PRT
<213> ORGANISM: Artificial Sequence
<220> FEATURE:
<223> OTHER INFORMATION: Peptide

<400> SEQUENCE: 17

```
Cys Asn Gly Arg Cys Val Ser Gly Cys Ala Gly Arg Cys
1               5                   10
```

<210> SEQ ID NO 18
<211> LENGTH: 6
<212> TYPE: PRT
<213> ORGANISM: Artificial Sequence
<220> FEATURE:
<223> OTHER INFORMATION: Peptide

<400> SEQUENCE: 18

```
Asn Gly Arg Ala His Ala
1               5
```

<210> SEQ ID NO 19
<211> LENGTH: 9
<212> TYPE: PRT
<213> ORGANISM: Artificial Sequence
<220> FEATURE:
<223> OTHER INFORMATION: Peptide

<400> SEQUENCE: 19

Cys Val Leu Asn Gly Arg Met Glu Cys
1               5

<210> SEQ ID NO 20
<211> LENGTH: 5
<212> TYPE: PRT
<213> ORGANISM: Artificial Sequence
<220> FEATURE:
<223> OTHER INFORMATION: Peptide

<400> SEQUENCE: 20

Cys Asn Gly Arg Cys
1               5

<210> SEQ ID NO 21
<211> LENGTH: 7
<212> TYPE: PRT
<213> ORGANISM: Artificial Sequence
<220> FEATURE:
<223> OTHER INFORMATION: Peptide

<400> SEQUENCE: 21

Cys Gly Ser Leu Val Arg Cys
1               5

<210> SEQ ID NO 22
<211> LENGTH: 8
<212> TYPE: PRT
<213> ORGANISM: Artificial Sequence
<220> FEATURE:
<223> OTHER INFORMATION: Peptide

<400> SEQUENCE: 22

Cys Leu Ser Gly Ser Leu Ser Cys
1               5

<210> SEQ ID NO 23
<211> LENGTH: 9
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(2)
<223> OTHER INFORMATION: Xaa = any amino acid
<220> FEATURE:
<221> NAME/KEY: MISC_FEATURE
<222> LOCATION: (8)..(9)
<223> OTHER INFORMATION: Xaa = any amino acid

<400> SEQUENCE: 23

Xaa Xaa Cys Asn Gly Arg Cys Xaa Xaa
1               5

<210> SEQ ID NO 24
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = cysteine, or any amino acid

```
<220> FEATURE:
<221> NAME/KEY: MISC_FEATURE
<222> LOCATION: (8)..(8)
<223> OTHER INFORMATION: Xaa = cysteine, or any amino acid
<220> FEATURE:
<221> NAME/KEY: MISC_FEATURE
<222> LOCATION: (9)..(10)
<223> OTHER INFORMATION: Xaa = any amino acid

<400> SEQUENCE: 24

Cys Xaa Xaa Xaa Asn Gly Arg Xaa Xaa Xaa Cys
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (6)..(11)
<223> OTHER INFORMATION: Xaa = any amino acid

<400> SEQUENCE: 25

Cys Asn Gly Arg Cys Xaa Xaa Xaa Xaa Xaa Xaa
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Peptide

<400> SEQUENCE: 26

Cys Asn Gly Arg Cys Val Ser Gly Cys Ala Gly Arg Cys
1               5                   10

<210> SEQ ID NO 27
<211> LENGTH: 6
<212> TYPE: PRT
<213> ORGANISM: Artificial Sequence
<220> FEATURE:
<223> OTHER INFORMATION: Peptide

<400> SEQUENCE: 27

Asn Gly Arg Ala His Ala
1               5

<210> SEQ ID NO 28
<211> LENGTH: 9
<212> TYPE: PRT
<213> ORGANISM: Artificial Sequence
<220> FEATURE:
<223> OTHER INFORMATION: Peptide

<400> SEQUENCE: 28

Cys Val Leu Asn Gly Arg Met Glu Cys
1               5

<210> SEQ ID NO 29
<211> LENGTH: 5
<212> TYPE: PRT
<213> ORGANISM: Artificial Sequence
<220> FEATURE:
<223> OTHER INFORMATION: Peptide

<400> SEQUENCE: 29
```

```
Cys Asn Gly Arg Cys
1               5

<210> SEQ ID NO 30
<211> LENGTH: 9
<212> TYPE: PRT
<213> ORGANISM: Artificial Sequence
<220> FEATURE:
<223> OTHER INFORMATION: Peptide

<400> SEQUENCE: 30

Ala Leu Asn Gly Arg Glu Glu Ser Pro
1               5

<210> SEQ ID NO 31
<211> LENGTH: 8
<212> TYPE: PRT
<213> ORGANISM: Artificial Sequence
<220> FEATURE:
<223> OTHER INFORMATION: Peptide

<400> SEQUENCE: 31

Cys Val Leu Asn Gly Arg Met Glu
1               5

<210> SEQ ID NO 32
<211> LENGTH: 10
<212> TYPE: PRT
<213> ORGANISM: Artificial Sequence
<220> FEATURE:
<223> OTHER INFORMATION: Peptide

<400> SEQUENCE: 32

Cys Lys Val Cys Asn Gly Arg Cys Cys Gly
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Peptide

<400> SEQUENCE: 33

Cys Glu Met Cys Asn Gly Arg Cys Met Gly
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Peptide

<400> SEQUENCE: 34

Cys Pro Leu Cys Asn Gly Arg Cys Ala Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Peptide

<400> SEQUENCE: 35
```

Cys Pro Thr Cys Asn Gly Arg Cys Val Arg
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Peptide

<400> SEQUENCE: 36

Cys Gly Val Cys Asn Gly Arg Cys Gly Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Peptide

<400> SEQUENCE: 37

Cys Glu Gln Cys Asn Gly Arg Cys Gly Gln
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Peptide

<400> SEQUENCE: 38

Cys Arg Asn Cys Asn Gly Arg Cys Glu Gly
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Peptide

<400> SEQUENCE: 39

Cys Val Leu Cys Asn Gly Arg Cys Trp Ser
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Peptide

<400> SEQUENCE: 40

Cys Val Thr Cys Asn Gly Arg Cys Arg Val
1               5                   10

<210> SEQ ID NO 41
<211> LENGTH: 10
<212> TYPE: PRT
<213> ORGANISM: Artificial Sequence
<220> FEATURE:
<223> OTHER INFORMATION: CTECNGRCQL

<400> SEQUENCE: 41

Cys Thr Glu Cys Asn Gly Arg Cys Gln Leu

<210> SEQ ID NO 42
<211> LENGTH: 10
<212> TYPE: PRT
<213> ORGANISM: Artificial Sequence
<220> FEATURE:
<223> OTHER INFORMATION: Peptide

<400> SEQUENCE: 42

Cys Arg Thr Cys Asn Gly Arg Cys Leu Glu
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Peptide

<400> SEQUENCE: 43

Cys Glu Thr Cys Asn Gly Arg Cys Val Gly
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Peptide

<400> SEQUENCE: 44

Cys Ala Val Cys Asn Gly Arg Cys Gly Phe
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Peptide

<400> SEQUENCE: 45

Cys Arg Asp Leu Asn Gly Arg Lys Val Met
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Peptide

<400> SEQUENCE: 46

Cys Ser Cys Cys Asn Gly Arg Cys Gly Asp
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Peptide

<400> SEQUENCE: 47

Cys Trp Gly Cys Asn Gly Arg Cys Arg Met
1               5                   10

```
<210> SEQ ID NO 48
<211> LENGTH: 10
<212> TYPE: PRT
<213> ORGANISM: Artificial Sequence
<220> FEATURE:
<223> OTHER INFORMATION: Peptide

<400> SEQUENCE: 48

Cys Pro Leu Cys Asn Gly Arg Cys Ala Arg
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Peptide

<400> SEQUENCE: 49

Cys Lys Ser Cys Asn Gly Arg Cys Leu Ala
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Peptide

<400> SEQUENCE: 50

Cys Val Pro Cys Asn Gly Arg Cys His Glu
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Peptide

<400> SEQUENCE: 51

Cys Gln Ser Cys Asn Gly Arg Cys Val Arg
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Peptide

<400> SEQUENCE: 52

Cys Arg Thr Cys Asn Gly Arg Cys Gln Val
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Peptide

<400> SEQUENCE: 53

Cys Val Gln Cys Asn Gly Arg Cys Ala Leu
1               5                   10
```

```
<210> SEQ ID NO 54
<211> LENGTH: 10
<212> TYPE: PRT
<213> ORGANISM: Artificial Sequence
<220> FEATURE:
<223> OTHER INFORMATION: Peptide

<400> SEQUENCE: 54

Cys Arg Cys Cys Asn Gly Arg Cys Ser Pro
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Peptide

<400> SEQUENCE: 55

Cys Ala Ser Asn Asn Gly Arg Val Val Leu
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Peptide

<400> SEQUENCE: 56

Cys Gly Arg Cys Asn Gly Arg Cys Leu Leu
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Peptide

<400> SEQUENCE: 57

Cys Trp Leu Cys Asn Gly Arg Cys Gly Arg
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Peptide

<400> SEQUENCE: 58

Cys Ser Lys Cys Asn Gly Arg Cys Gly His
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Peptide

<400> SEQUENCE: 59

Cys Val Trp Cys Asn Gly Arg Cys Gly Leu
1               5                   10
```

```
<210> SEQ ID NO 60
<211> LENGTH: 10
<212> TYPE: PRT
<213> ORGANISM: Artificial Sequence
<220> FEATURE:
<223> OTHER INFORMATION: Peptide

<400> SEQUENCE: 60

Cys Ile Arg Cys Asn Gly Arg Cys Ser Val
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Peptide

<400> SEQUENCE: 61

Cys Gly Glu Cys Asn Gly Arg Cys Val Glu
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Peptide

<400> SEQUENCE: 62

Cys Glu Gly Val Asn Gly Arg Arg Leu Arg
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Peptide

<400> SEQUENCE: 63

Cys Leu Ser Cys Asn Gly Arg Cys Pro Ser
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Peptide

<400> SEQUENCE: 64

Cys Glu Val Cys Asn Gly Arg Cys Ala Leu
1               5                   10

<210> SEQ ID NO 65
<211> LENGTH: 9
<212> TYPE: PRT
<213> ORGANISM: Artificial Sequence
<220> FEATURE:
<223> OTHER INFORMATION: Peptide

<400> SEQUENCE: 65

Cys Asn Ser Arg Leu His Leu Arg Cys
1               5

<210> SEQ ID NO 66
```

```
<211> LENGTH: 9
<212> TYPE: PRT
<213> ORGANISM: Artificial Sequence
<220> FEATURE:
<223> OTHER INFORMATION: Peptide

<400> SEQUENCE: 66

Cys Glu Asn Trp Trp Gly Asp Val Cys
1               5

<210> SEQ ID NO 67
<211> LENGTH: 21
<212> TYPE: PRT
<213> ORGANISM: Artificial Sequence
<220> FEATURE:
<223> OTHER INFORMATION: Peptide

<400> SEQUENCE: 67

Trp Arg Cys Val Leu Arg Glu Gly Pro Ala Gly Gly Cys Ala Trp Phe
1               5                   10                  15

Asn Arg His Arg Leu
            20

<210> SEQ ID NO 68
<211> LENGTH: 9
<212> TYPE: PRT
<213> ORGANISM: Artificial Sequence
<220> FEATURE:
<223> OTHER INFORMATION: Peptide

<400> SEQUENCE: 68

Cys Leu Ser Ser Arg Leu Asp Ala Cys
1               5

<210> SEQ ID NO 69
<211> LENGTH: 8
<212> TYPE: PRT
<213> ORGANISM: Artificial Sequence
<220> FEATURE:
<223> OTHER INFORMATION: Peptide

<400> SEQUENCE: 69

Cys Val Leu Arg Gly Gly Arg Cys
1               5

<210> SEQ ID NO 70
<211> LENGTH: 9
<212> TYPE: PRT
<213> ORGANISM: Artificial Sequence
<220> FEATURE:
<223> OTHER INFORMATION: Peptide

<400> SEQUENCE: 70

Cys Asn Ser Arg Leu Gln Leu Arg Cys
1               5

<210> SEQ ID NO 71
<211> LENGTH: 7
<212> TYPE: PRT
<213> ORGANISM: Artificial Sequence
<220> FEATURE:
<223> OTHER INFORMATION: Peptide

<400> SEQUENCE: 71

Cys Gly Val Arg Leu Gly Cys
1               5
```

```
<210> SEQ ID NO 72
<211> LENGTH: 8
<212> TYPE: PRT
<213> ORGANISM: Artificial Sequence
<220> FEATURE:
<223> OTHER INFORMATION: Peptide

<400> SEQUENCE: 72

Cys Lys Asp Trp Gly Arg Ile Cys
1               5

<210> SEQ ID NO 73
<211> LENGTH: 8
<212> TYPE: PRT
<213> ORGANISM: Artificial Sequence
<220> FEATURE:
<223> OTHER INFORMATION: Peptide

<400> SEQUENCE: 73

Cys Leu Asp Trp Gly Arg Ile Cys
1               5

<210> SEQ ID NO 74
<211> LENGTH: 8
<212> TYPE: PRT
<213> ORGANISM: Artificial Sequence
<220> FEATURE:
<223> OTHER INFORMATION: Peptide

<400> SEQUENCE: 74

Cys Thr Arg Ile Thr Glu Ser Cys
1               5

<210> SEQ ID NO 75
<211> LENGTH: 7
<212> TYPE: PRT
<213> ORGANISM: Artificial Sequence
<220> FEATURE:
<223> OTHER INFORMATION: Peptide

<400> SEQUENCE: 75

Cys Glu Thr Leu Pro Ala Cys
1               5

<210> SEQ ID NO 76
<211> LENGTH: 8
<212> TYPE: PRT
<213> ORGANISM: Artificial Sequence
<220> FEATURE:
<223> OTHER INFORMATION: Peptide

<400> SEQUENCE: 76

Cys Arg Thr Gly Thr Leu Phe Cys
1               5

<210> SEQ ID NO 77
<211> LENGTH: 8
<212> TYPE: PRT
<213> ORGANISM: Artificial Sequence
<220> FEATURE:
<223> OTHER INFORMATION: Peptide

<400> SEQUENCE: 77

Cys Gly Arg Ser Leu Asp Ala Cys
1               5
```

```
<210> SEQ ID NO 78
<211> LENGTH: 9
<212> TYPE: PRT
<213> ORGANISM: Artificial Sequence
<220> FEATURE:
<223> OTHER INFORMATION: Peptide

<400> SEQUENCE: 78

Cys Arg His Trp Phe Asp Val Val Cys
1               5

<210> SEQ ID NO 79
<211> LENGTH: 8
<212> TYPE: PRT
<213> ORGANISM: Artificial Sequence
<220> FEATURE:
<223> OTHER INFORMATION: Peptide

<400> SEQUENCE: 79

Cys Ala Asn Ala Gln Ser His Cys
1               5

<210> SEQ ID NO 80
<211> LENGTH: 8
<212> TYPE: PRT
<213> ORGANISM: Artificial Sequence
<220> FEATURE:
<223> OTHER INFORMATION: Peptide

<400> SEQUENCE: 80

Cys Gly Asn Pro Ser Tyr Arg Cys
1               5

<210> SEQ ID NO 81
<211> LENGTH: 20
<212> TYPE: PRT
<213> ORGANISM: Artificial Sequence
<220> FEATURE:
<223> OTHER INFORMATION: Peptide

<400> SEQUENCE: 81

Tyr Pro Cys Gly Gly Glu Ala Val Ala Gly Val Ser Ser Val Arg Thr
1               5                   10                  15

Met Cys Ser Glu
            20

<210> SEQ ID NO 82
<211> LENGTH: 20
<212> TYPE: PRT
<213> ORGANISM: Artificial Sequence
<220> FEATURE:
<223> OTHER INFORMATION: Peptide

<400> SEQUENCE: 82

Leu Asn Cys Asp Tyr Gln Gly Thr Asn Pro Ala Thr Ser Val Ser Val
1               5                   10                  15

Pro Cys Thr Val
            20

<210> SEQ ID NO 83
<211> LENGTH: 7
<212> TYPE: PRT
<213> ORGANISM: Artificial Sequence
<220> FEATURE:
<223> OTHER INFORMATION: Peptide

<400> SEQUENCE: 83
```

```
Cys Leu Pro Val Ala Ser Cys
1               5

<210> SEQ ID NO 84
<211> LENGTH: 7
<212> TYPE: PRT
<213> ORGANISM: Artificial Sequence
<220> FEATURE:
<223> OTHER INFORMATION: Peptide

<400> SEQUENCE: 84

Cys Gly Ala Arg Glu Met Cys
1               5

<210> SEQ ID NO 85
<211> LENGTH: 8
<212> TYPE: PRT
<213> ORGANISM: Artificial Sequence
<220> FEATURE:
<223> OTHER INFORMATION: Peptide

<400> SEQUENCE: 85

Cys Lys Gly Arg Ser Ser Ala Cys
1               5

<210> SEQ ID NO 86
<211> LENGTH: 8
<212> TYPE: PRT
<213> ORGANISM: Artificial Sequence
<220> FEATURE:
<223> OTHER INFORMATION: Peptide

<400> SEQUENCE: 86

Cys Trp Ala Arg Ala Gln Gly Cys
1               5

<210> SEQ ID NO 87
<211> LENGTH: 8
<212> TYPE: PRT
<213> ORGANISM: Artificial Sequence
<220> FEATURE:
<223> OTHER INFORMATION: Peptide

<400> SEQUENCE: 87

Cys Leu Gly Arg Ser Ser Val Cys
1               5

<210> SEQ ID NO 88
<211> LENGTH: 8
<212> TYPE: PRT
<213> ORGANISM: Artificial Sequence
<220> FEATURE:
<223> OTHER INFORMATION: Peptide

<400> SEQUENCE: 88

Cys Thr Ser Pro Gly Gly Ser Cys
1               5

<210> SEQ ID NO 89
<211> LENGTH: 8
<212> TYPE: PRT
<213> ORGANISM: Artificial Sequence
<220> FEATURE:
<223> OTHER INFORMATION: Peptide

<400> SEQUENCE: 89
```

```
Cys Met Gly Arg Trp Arg Leu Cys
1               5

<210> SEQ ID NO 90
<211> LENGTH: 8
<212> TYPE: PRT
<213> ORGANISM: Artificial Sequence
<220> FEATURE:
<223> OTHER INFORMATION: Peptide

<400> SEQUENCE: 90

Cys Val Gly Glu Cys Gly Gly Cys
1               5

<210> SEQ ID NO 91
<211> LENGTH: 7
<212> TYPE: PRT
<213> ORGANISM: Artificial Sequence
<220> FEATURE:
<223> OTHER INFORMATION: Peptide

<400> SEQUENCE: 91

Cys Val Ala Trp Leu Asn Cys
1               5

<210> SEQ ID NO 92
<211> LENGTH: 7
<212> TYPE: PRT
<213> ORGANISM: Artificial Sequence
<220> FEATURE:
<223> OTHER INFORMATION: Peptide

<400> SEQUENCE: 92

Cys Arg Arg Phe Gln Asp Cys
1               5

<210> SEQ ID NO 93
<211> LENGTH: 7
<212> TYPE: PRT
<213> ORGANISM: Artificial Sequence
<220> FEATURE:
<223> OTHER INFORMATION: Peptide

<400> SEQUENCE: 93

Cys Leu Met Gly Val His Cys
1               5

<210> SEQ ID NO 94
<211> LENGTH: 8
<212> TYPE: PRT
<213> ORGANISM: Artificial Sequence
<220> FEATURE:
<223> OTHER INFORMATION: Peptide

<400> SEQUENCE: 94

Cys Lys Leu Leu Ser Gly Val Cys
1               5

<210> SEQ ID NO 95
<211> LENGTH: 8
<212> TYPE: PRT
<213> ORGANISM: Artificial Sequence
<220> FEATURE:
<223> OTHER INFORMATION: Peptide

<400> SEQUENCE: 95

Cys Phe Val Gly His Asp Leu Cys
```

```
1               5

<210> SEQ ID NO 96
<211> LENGTH: 7
<212> TYPE: PRT
<213> ORGANISM: Artificial Sequence
<220> FEATURE:
<223> OTHER INFORMATION: Peptide

<400> SEQUENCE: 96

Cys Arg Cys Leu Asn Val Cys
1               5

<210> SEQ ID NO 97
<211> LENGTH: 7
<212> TYPE: PRT
<213> ORGANISM: Artificial Sequence
<220> FEATURE:
<223> OTHER INFORMATION: Peptide

<400> SEQUENCE: 97

Cys Lys Leu Met Gly Glu Cys
1               5

<210> SEQ ID NO 98
<211> LENGTH: 9
<212> TYPE: PRT
<213> ORGANISM: Artificial Sequence
<220> FEATURE:
<223> OTHER INFORMATION: Peptide

<400> SEQUENCE: 98

Cys Ala Arg Ser Lys Asn Lys Asp Cys
1               5

<210> SEQ ID NO 99
<211> LENGTH: 6
<212> TYPE: PRT
<213> ORGANISM: Artificial Sequence
<220> FEATURE:
<223> OTHER INFORMATION: Peptide

<400> SEQUENCE: 99

Cys Arg Lys Asp Lys Cys
1               5

<210> SEQ ID NO 100
<211> LENGTH: 13
<212> TYPE: PRT
<213> ORGANISM: Artificial Sequence
<220> FEATURE:
<223> OTHER INFORMATION: Peptide

<400> SEQUENCE: 100

Cys Val Ala Leu Cys Arg Glu Ala Cys Gly Glu Gly Cys
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Peptide

<400> SEQUENCE: 101

Cys Ser Ser Gly Cys Ser Lys Asn Cys Leu Glu Met Cys
1               5                   10
```

```
<210> SEQ ID NO 102
<211> LENGTH: 8
<212> TYPE: PRT
<213> ORGANISM: Artificial Sequence
<220> FEATURE:
<223> OTHER INFORMATION: Peptide

<400> SEQUENCE: 102

Cys Ile Gly Glu Val Glu Val Cys
1               5

<210> SEQ ID NO 103
<211> LENGTH: 9
<212> TYPE: PRT
<213> ORGANISM: Artificial Sequence
<220> FEATURE:
<223> OTHER INFORMATION: Peptide

<400> SEQUENCE: 103

Cys Lys Trp Ser Arg Leu His Ser Cys
1               5

<210> SEQ ID NO 104
<211> LENGTH: 9
<212> TYPE: PRT
<213> ORGANISM: Artificial Sequence
<220> FEATURE:
<223> OTHER INFORMATION: Peptide

<400> SEQUENCE: 104

Cys Trp Arg Gly Asp Arg Lys Ile Cys
1               5

<210> SEQ ID NO 105
<211> LENGTH: 9
<212> TYPE: PRT
<213> ORGANISM: Artificial Sequence
<220> FEATURE:
<223> OTHER INFORMATION: Peptide

<400> SEQUENCE: 105

Cys Glu Arg Val Val Gly Ser Ser Cys
1               5

<210> SEQ ID NO 106
<211> LENGTH: 9
<212> TYPE: PRT
<213> ORGANISM: Artificial Sequence
<220> FEATURE:
<223> OTHER INFORMATION: Peptide

<400> SEQUENCE: 106

Cys Leu Ala Lys Glu Asn Val Val Cys
1               5

<210> SEQ ID NO 107
<211> LENGTH: 13
<212> TYPE: PRT
<213> ORGANISM: Artificial Sequence
<220> FEATURE:
<223> OTHER INFORMATION: Peptide

<400> SEQUENCE: 107

Cys Gly Phe Glu Cys Val Arg Gln Cys Pro Glu Arg Cys
1               5                   10
```

<210> SEQ ID NO 108
<211> LENGTH: 8
<212> TYPE: PRT
<213> ORGANISM: Artificial Sequence
<220> FEATURE:
<223> OTHER INFORMATION: Peptide

<400> SEQUENCE: 108

Cys Gly Phe Glu Leu Glu Thr Cys
1               5

<210> SEQ ID NO 109
<211> LENGTH: 8
<212> TYPE: PRT
<213> ORGANISM: Artificial Sequence
<220> FEATURE:
<223> OTHER INFORMATION: Peptide

<400> SEQUENCE: 109

Cys Thr Leu Arg Asp Arg Asn Cys
1               5

<210> SEQ ID NO 110
<211> LENGTH: 8
<212> TYPE: PRT
<213> ORGANISM: Artificial Sequence
<220> FEATURE:
<223> OTHER INFORMATION: Peptide

<400> SEQUENCE: 110

Cys Ile Gly Glu Val Glu Val Cys
1               5

<210> SEQ ID NO 111
<211> LENGTH: 8
<212> TYPE: PRT
<213> ORGANISM: Artificial Sequence
<220> FEATURE:
<223> OTHER INFORMATION: Peptide

<400> SEQUENCE: 111

Cys Gly Lys Arg Tyr Arg Asn Cys
1               5

<210> SEQ ID NO 112
<211> LENGTH: 8
<212> TYPE: PRT
<213> ORGANISM: Artificial Sequence
<220> FEATURE:
<223> OTHER INFORMATION: Peptide

<400> SEQUENCE: 112

Cys Leu Arg Pro Tyr Leu Asn Cys
1               5

<210> SEQ ID NO 113
<211> LENGTH: 12
<212> TYPE: PRT
<213> ORGANISM: Artificial Sequence
<220> FEATURE:
<223> OTHER INFORMATION: Peptide

<400> SEQUENCE: 113

Cys Thr Val Asn Glu Ala Tyr Lys Thr Arg Met Cys
1               5                   10

```
<210> SEQ ID NO 114
<211> LENGTH: 12
<212> TYPE: PRT
<213> ORGANISM: Artificial Sequence
<220> FEATURE:
<223> OTHER INFORMATION: Peptide

<400> SEQUENCE: 114

Cys Arg Leu Arg Ser Tyr Gly Thr Leu Ser Leu Cys
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Peptide

<400> SEQUENCE: 115

Cys Arg Pro Trp His Asn Gln Ala His Thr Glu Cys
1               5                   10

<210> SEQ ID NO 116
<211> LENGTH: 9
<212> TYPE: PRT
<213> ORGANISM: Artificial Sequence
<220> FEATURE:
<223> OTHER INFORMATION: Peptide

<400> SEQUENCE: 116

Ser Trp Cys Glu Pro Gly Trp Cys Arg
1               5

<210> SEQ ID NO 117
<211> LENGTH: 7
<212> TYPE: PRT
<213> ORGANISM: Artificial Sequence
<220> FEATURE:
<223> OTHER INFORMATION: Peptide

<400> SEQUENCE: 117

Cys Lys Ala Ala Lys Asn Lys
1               5

<210> SEQ ID NO 118
<211> LENGTH: 7
<212> TYPE: PRT
<213> ORGANISM: Artificial Sequence
<220> FEATURE:
<223> OTHER INFORMATION: Peptide

<400> SEQUENCE: 118

Cys Lys Gly Ala Lys Ala Arg
1               5

<210> SEQ ID NO 119
<211> LENGTH: 8
<212> TYPE: PRT
<213> ORGANISM: Artificial Sequence
<220> FEATURE:
<223> OTHER INFORMATION: Peptide

<400> SEQUENCE: 119

Val Gly Val Gly Glu Trp Ser Val
1               5

<210> SEQ ID NO 120
```

```
<211> LENGTH: 7
<212> TYPE: PRT
<213> ORGANISM: Artificial Sequence
<220> FEATURE:
<223> OTHER INFORMATION: Peptide

<400> SEQUENCE: 120

Tyr Ser Gly Lys Trp Gly Trp
1               5

<210> SEQ ID NO 121
<211> LENGTH: 7
<212> TYPE: PRT
<213> ORGANISM: Artificial Sequence
<220> FEATURE:
<223> OTHER INFORMATION: Peptide

<400> SEQUENCE: 121

Gly Leu Ser Gly Gly Arg Ser
1               5

<210> SEQ ID NO 122
<211> LENGTH: 7
<212> TYPE: PRT
<213> ORGANISM: Artificial Sequence
<220> FEATURE:
<223> OTHER INFORMATION: Peptide

<400> SEQUENCE: 122

Leu Met Leu Pro Arg Ala Asp
1               5

<210> SEQ ID NO 123
<211> LENGTH: 7
<212> TYPE: PRT
<213> ORGANISM: Artificial Sequence
<220> FEATURE:
<223> OTHER INFORMATION: Peptide

<400> SEQUENCE: 123

Leu Pro Arg Tyr Leu Leu Ser
1               5

<210> SEQ ID NO 124
<211> LENGTH: 9
<212> TYPE: PRT
<213> ORGANISM: Artificial Sequence
<220> FEATURE:
<223> OTHER INFORMATION: Peptide

<400> SEQUENCE: 124

Cys Ser Cys Phe Arg Asp Val Cys Cys
1               5

<210> SEQ ID NO 125
<211> LENGTH: 9
<212> TYPE: PRT
<213> ORGANISM: Artificial Sequence
<220> FEATURE:
<223> OTHER INFORMATION: Peptide

<400> SEQUENCE: 125

Cys Arg Asp Val Val Ser Val Ile Cys
1               5

<210> SEQ ID NO 126
<211> LENGTH: 7
```

```
<212> TYPE: PRT
<213> ORGANISM: Artificial Sequence
<220> FEATURE:
<223> OTHER INFORMATION: Peptide

<400> SEQUENCE: 126

Tyr Ser Gly Lys Trp Gly Lys
1               5

<210> SEQ ID NO 127
<211> LENGTH: 8
<212> TYPE: PRT
<213> ORGANISM: Artificial Sequence
<220> FEATURE:
<223> OTHER INFORMATION: Peptide

<400> SEQUENCE: 127

Gly Ile Ser Ala Leu Val Leu Ser
1               5

<210> SEQ ID NO 128
<211> LENGTH: 7
<212> TYPE: PRT
<213> ORGANISM: Artificial Sequence
<220> FEATURE:
<223> OTHER INFORMATION: Peptide

<400> SEQUENCE: 128

Ser Arg Arg Gln Pro Leu Ser
1               5

<210> SEQ ID NO 129
<211> LENGTH: 7
<212> TYPE: PRT
<213> ORGANISM: Artificial Sequence
<220> FEATURE:
<223> OTHER INFORMATION: Peptide

<400> SEQUENCE: 129

Met Ser Pro Gln Leu Ala Thr
1               5

<210> SEQ ID NO 130
<211> LENGTH: 7
<212> TYPE: PRT
<213> ORGANISM: Artificial Sequence
<220> FEATURE:
<223> OTHER INFORMATION: Peptide

<400> SEQUENCE: 130

Met Arg Arg Asp Glu Gln Arg
1               5

<210> SEQ ID NO 131
<211> LENGTH: 7
<212> TYPE: PRT
<213> ORGANISM: Artificial Sequence
<220> FEATURE:
<223> OTHER INFORMATION: Peptide

<400> SEQUENCE: 131

Gln Val Arg Arg Val Pro Glu
1               5

<210> SEQ ID NO 132
<211> LENGTH: 7
<212> TYPE: PRT
```

```
<213> ORGANISM: Artificial Sequence
<220> FEATURE:
<223> OTHER INFORMATION: Peptide

<400> SEQUENCE: 132

Val Arg Arg Gly Ser Pro Gln
1               5

<210> SEQ ID NO 133
<211> LENGTH: 7
<212> TYPE: PRT
<213> ORGANISM: Artificial Sequence
<220> FEATURE:
<223> OTHER INFORMATION: Peptide

<400> SEQUENCE: 133

Gly Gly Arg Gly Ser Trp Glu
1               5

<210> SEQ ID NO 134
<211> LENGTH: 7
<212> TYPE: PRT
<213> ORGANISM: Artificial Sequence
<220> FEATURE:
<223> OTHER INFORMATION: Peptide

<400> SEQUENCE: 134

Phe Arg Val Arg Gly Ser Pro
1               5

<210> SEQ ID NO 135
<211> LENGTH: 7
<212> TYPE: PRT
<213> ORGANISM: Artificial Sequence
<220> FEATURE:
<223> OTHER INFORMATION: Peptide

<400> SEQUENCE: 135

Arg Val Arg Gly Pro Glu Arg
1               5

<210> SEQ ID NO 136
<211> LENGTH: 7
<212> TYPE: PRT
<213> ORGANISM: Artificial Sequence
<220> FEATURE:
<223> OTHER INFORMATION: Peptide

<400> SEQUENCE: 136

Val Lys Ser Val Cys Arg Thr
1               5

<210> SEQ ID NO 137
<211> LENGTH: 7
<212> TYPE: PRT
<213> ORGANISM: Artificial Sequence
<220> FEATURE:
<223> OTHER INFORMATION: Peptide

<400> SEQUENCE: 137

Trp Arg Gln Asn Met Pro Leu
1               5

<210> SEQ ID NO 138
<211> LENGTH: 7
<212> TYPE: PRT
<213> ORGANISM: Artificial Sequence
```

```
<220> FEATURE:
<223> OTHER INFORMATION: Peptide

<400> SEQUENCE: 138

Ser Arg Arg Phe Val Gly Gly
1               5

<210> SEQ ID NO 139
<211> LENGTH: 7
<212> TYPE: PRT
<213> ORGANISM: Artificial Sequence
<220> FEATURE:
<223> OTHER INFORMATION: Peptide

<400> SEQUENCE: 139

Ala Leu Glu Arg Arg Ser Leu
1               5

<210> SEQ ID NO 140
<211> LENGTH: 7
<212> TYPE: PRT
<213> ORGANISM: Artificial Sequence
<220> FEATURE:
<223> OTHER INFORMATION: Peptide

<400> SEQUENCE: 140

Ala Arg Arg Gly Trp Thr Leu
1               5

<210> SEQ ID NO 141
<211> LENGTH: 7
<212> TYPE: PRT
<213> ORGANISM: Artificial Sequence
<220> FEATURE:
<223> OTHER INFORMATION: Peptide

<400> SEQUENCE: 141

Ser Met Ser Ile Ala Arg Leu
1               5

<210> SEQ ID NO 142
<211> LENGTH: 7
<212> TYPE: PRT
<213> ORGANISM: Artificial Sequence
<220> FEATURE:
<223> OTHER INFORMATION: Peptide

<400> SEQUENCE: 142

Val Ser Phe Leu Glu Tyr Arg
1               5

<210> SEQ ID NO 143
<211> LENGTH: 7
<212> TYPE: PRT
<213> ORGANISM: Artificial Sequence
<220> FEATURE:
<223> OTHER INFORMATION: Peptide

<400> SEQUENCE: 143

Arg Gly Arg Trp Leu Ala Leu
1               5

<210> SEQ ID NO 144
<211> LENGTH: 7
<212> TYPE: PRT
<213> ORGANISM: Artificial Sequence
<220> FEATURE:
```

```
<223> OTHER INFORMATION: Peptide

<400> SEQUENCE: 144

Glu Val Arg Ser Arg Leu Ser
1               5

<210> SEQ ID NO 145
<211> LENGTH: 7
<212> TYPE: PRT
<213> ORGANISM: Artificial Sequence
<220> FEATURE:
<223> OTHER INFORMATION: Peptide

<400> SEQUENCE: 145

Val Arg Ala Arg Leu Met Ser
1               5

<210> SEQ ID NO 146
<211> LENGTH: 7
<212> TYPE: PRT
<213> ORGANISM: Artificial Sequence
<220> FEATURE:
<223> OTHER INFORMATION: Peptide

<400> SEQUENCE: 146

Arg Val Gly Leu Val Ala Arg
1               5

<210> SEQ ID NO 147
<211> LENGTH: 7
<212> TYPE: PRT
<213> ORGANISM: Artificial Sequence
<220> FEATURE:
<223> OTHER INFORMATION: Peptide

<400> SEQUENCE: 147

Arg Val Arg Leu Val Asn Leu
1               5

<210> SEQ ID NO 148
<211> LENGTH: 5
<212> TYPE: PRT
<213> ORGANISM: Artificial Sequence
<220> FEATURE:
<223> OTHER INFORMATION: Peptide

<400> SEQUENCE: 148

Cys Arg Glu Lys Ala
1               5

<210> SEQ ID NO 149
<211> LENGTH: 5
<212> TYPE: PRT
<213> ORGANISM: Artificial Sequence
<220> FEATURE:
<223> OTHER INFORMATION: Peptide

<400> SEQUENCE: 149

Cys Arg Pro Pro Arg
1               5

<210> SEQ ID NO 150
<211> LENGTH: 9
<212> TYPE: PRT
<213> ORGANISM: Artificial Sequence
<220> FEATURE:
<223> OTHER INFORMATION: Peptide
```

```
<400> SEQUENCE: 150

Cys Gly Arg Lys Ser Lys Thr Val Cys
1               5

<210> SEQ ID NO 151
<211> LENGTH: 6
<212> TYPE: PRT
<213> ORGANISM: Artificial Sequence
<220> FEATURE:
<223> OTHER INFORMATION: Peptide

<400> SEQUENCE: 151

Cys Ala Arg Pro Ala Arg
1               5

<210> SEQ ID NO 152
<211> LENGTH: 6
<212> TYPE: PRT
<213> ORGANISM: Artificial Sequence
<220> FEATURE:
<223> OTHER INFORMATION: Peptide

<400> SEQUENCE: 152

Cys Pro Lys Arg Pro Arg
1               5

<210> SEQ ID NO 153
<211> LENGTH: 6
<212> TYPE: PRT
<213> ORGANISM: Artificial Sequence
<220> FEATURE:
<223> OTHER INFORMATION: Peptide

<400> SEQUENCE: 153

Cys Lys Arg Ala Val Arg
1               5

<210> SEQ ID NO 154
<211> LENGTH: 9
<212> TYPE: PRT
<213> ORGANISM: Artificial Sequence
<220> FEATURE:
<223> OTHER INFORMATION: Peptide

<400> SEQUENCE: 154

Cys Arg Asn Ser Trp Lys Pro Asn Cys
1               5

<210> SEQ ID NO 155
<211> LENGTH: 5
<212> TYPE: PRT
<213> ORGANISM: Artificial Sequence
<220> FEATURE:
<223> OTHER INFORMATION: Peptide

<400> SEQUENCE: 155

Arg Gly Ser Ser Ser
1               5

<210> SEQ ID NO 156
<211> LENGTH: 9
<212> TYPE: PRT
<213> ORGANISM: Artificial Sequence
<220> FEATURE:
<223> OTHER INFORMATION: Peptide
```

```
<400> SEQUENCE: 156

Cys Arg Ser Thr Arg Ala Asn Pro Cys
1               5

<210> SEQ ID NO 157
<211> LENGTH: 9
<212> TYPE: PRT
<213> ORGANISM: Artificial Sequence
<220> FEATURE:
<223> OTHER INFORMATION: Peptide

<400> SEQUENCE: 157

Cys Pro Lys Thr Arg Arg Val Pro Cys
1               5

<210> SEQ ID NO 158
<211> LENGTH: 9
<212> TYPE: PRT
<213> ORGANISM: Artificial Sequence
<220> FEATURE:
<223> OTHER INFORMATION: Peptide

<400> SEQUENCE: 158

Cys Ser Gly Met Ala Arg Thr Lys Cys
1               5

<210> SEQ ID NO 159
<211> LENGTH: 7
<212> TYPE: PRT
<213> ORGANISM: Artificial Sequence
<220> FEATURE:
<223> OTHER INFORMATION: Peptide

<400> SEQUENCE: 159

Gly Gly Gly Val Phe Trp Gln
1               5

<210> SEQ ID NO 160
<211> LENGTH: 7
<212> TYPE: PRT
<213> ORGANISM: Artificial Sequence
<220> FEATURE:
<223> OTHER INFORMATION: Peptide

<400> SEQUENCE: 160

His Gly Arg Val Arg Pro His
1               5

<210> SEQ ID NO 161
<211> LENGTH: 7
<212> TYPE: PRT
<213> ORGANISM: Artificial Sequence
<220> FEATURE:
<223> OTHER INFORMATION: Peptide

<400> SEQUENCE: 161

Val Val Leu Val Thr Ser Ser
1               5

<210> SEQ ID NO 162
<211> LENGTH: 8
<212> TYPE: PRT
<213> ORGANISM: Artificial Sequence
<220> FEATURE:
<223> OTHER INFORMATION: Peptide

<400> SEQUENCE: 162
```

```
Cys Leu His Arg Gly Asn Ser Cys
1               5
```

<210> SEQ ID NO 163
<211> LENGTH: 12
<212> TYPE: PRT
<213> ORGANISM: Artificial Sequence
<220> FEATURE:
<223> OTHER INFORMATION: Peptide

<400> SEQUENCE: 163

```
Cys Arg Ser Trp Asn Lys Ala Asp Asn Arg Ser Cys
1               5                   10
```

<210> SEQ ID NO 164
<211> LENGTH: 9
<212> TYPE: PRT
<213> ORGANISM: Artificial Sequence
<220> FEATURE:
<223> OTHER INFORMATION: Peptide

<400> SEQUENCE: 164

```
Cys Gly Arg Lys Ser Lys Thr Val Cys
1               5
```

<210> SEQ ID NO 165
<211> LENGTH: 6
<212> TYPE: PRT
<213> ORGANISM: Artificial Sequence
<220> FEATURE:
<223> OTHER INFORMATION: Peptide

<400> SEQUENCE: 165

```
Cys Lys Arg Ala Val Arg
1               5
```

<210> SEQ ID NO 166
<211> LENGTH: 9
<212> TYPE: PRT
<213> ORGANISM: Artificial Sequence
<220> FEATURE:
<223> OTHER INFORMATION: Peptide

<400> SEQUENCE: 166

```
Cys Arg Asn Ser Trp Lys Pro Asn Cys
1               5
```

<210> SEQ ID NO 167
<211> LENGTH: 9
<212> TYPE: PRT
<213> ORGANISM: Artificial Sequence
<220> FEATURE:
<223> OTHER INFORMATION: Peptide

<400> SEQUENCE: 167

```
Cys Pro Lys Thr Arg Arg Val Pro Cys
1               5
```

<210> SEQ ID NO 168
<211> LENGTH: 9
<212> TYPE: PRT
<213> ORGANISM: Artificial Sequence
<220> FEATURE:
<223> OTHER INFORMATION: Peptide

<400> SEQUENCE: 168

Cys Ser Gly Met Ala Arg Thr Lys Cys
1               5

<210> SEQ ID NO 169
<211> LENGTH: 6
<212> TYPE: PRT
<213> ORGANISM: Artificial Sequence
<220> FEATURE:
<223> OTHER INFORMATION: Peptide

<400> SEQUENCE: 169

Cys Ala Arg Pro Ala Arg
1               5

<210> SEQ ID NO 170
<211> LENGTH: 6
<212> TYPE: PRT
<213> ORGANISM: Artificial Sequence
<220> FEATURE:
<223> OTHER INFORMATION: Peptide

<400> SEQUENCE: 170

Cys Pro Lys Arg Pro Arg
1               5

<210> SEQ ID NO 171
<211> LENGTH: 16
<212> TYPE: PRT
<213> ORGANISM: Artificial Sequence
<220> FEATURE:
<223> OTHER INFORMATION: Peptide

<400> SEQUENCE: 171

Arg Gln Pro Lys Ile Trp Phe Pro Asn Arg Arg Lys Pro Trp Lys Lys
1               5                   10                  15

<210> SEQ ID NO 172
<211> LENGTH: 11
<212> TYPE: PRT
<213> ORGANISM: Artificial Sequence
<220> FEATURE:
<223> OTHER INFORMATION: Peptide

<400> SEQUENCE: 172

Gly Arg Lys Lys Arg Arg Gln Arg Pro Pro Gln
1               5                   10

<210> SEQ ID NO 173
<211> LENGTH: 16
<212> TYPE: PRT
<213> ORGANISM: Artificial Sequence
<220> FEATURE:
<223> OTHER INFORMATION: Peptide

<400> SEQUENCE: 173

Arg Gln Ile Lys Ile Trp Phe Gln Asn Arg Arg Met Lys Trp Lys Lys
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: Peptide

<400> SEQUENCE: 174

Arg Gln Ile Ala Ile Trp Phe Gln Asn Arg Arg Met Lys Trp Ala Ala

<210> SEQ ID NO 175
<211> LENGTH: 9
<212> TYPE: PRT
<213> ORGANISM: Artificial Sequence
<220> FEATURE:
<223> OTHER INFORMATION: Peptide

<400> SEQUENCE: 175

Arg Lys Lys Arg Arg Gln Arg Arg Arg
1               5

<210> SEQ ID NO 176
<211> LENGTH: 21
<212> TYPE: PRT
<213> ORGANISM: Artificial Sequence
<220> FEATURE:
<223> OTHER INFORMATION: Peptide

<400> SEQUENCE: 176

Thr Arg Ser Ser Arg Ala Gly Leu Gln Phe Pro Val Gly Arg Val His
1               5                   10                  15

Arg Leu Leu Arg Lys
            20

<210> SEQ ID NO 177
<211> LENGTH: 26
<212> TYPE: PRT
<213> ORGANISM: Artificial Sequence
<220> FEATURE:
<223> OTHER INFORMATION: Peptide

<400> SEQUENCE: 177

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 178
<211> LENGTH: 18
<212> TYPE: PRT
<213> ORGANISM: Artificial Sequence
<220> FEATURE:
<223> OTHER INFORMATION: Peptide

<400> SEQUENCE: 178

Lys Leu Ala Leu Lys Leu Ala Leu Lys Ala Leu Lys Ala Ala Leu Lys
1               5                   10                  15

Leu Ala

<210> SEQ ID NO 179
<211> LENGTH: 16
<212> TYPE: PRT
<213> ORGANISM: Artificial Sequence
<220> FEATURE:
<223> OTHER INFORMATION: Peptide

<400> SEQUENCE: 179

Ala Ala Val Ala Leu Leu Pro Ala Val Leu Leu Ala Leu Leu Ala Pro
1               5                   10                  15

<210> SEQ ID NO 180
<211> LENGTH: 10
<212> TYPE: PRT

```
<213> ORGANISM: Artificial Sequence
<220> FEATURE:
<223> OTHER INFORMATION: Peptide

<400> SEQUENCE: 180

Val Pro Met Leu Lys Pro Met Leu Lys Glu
1               5                   10

<210> SEQ ID NO 181
<211> LENGTH: 28
<212> TYPE: PRT
<213> ORGANISM: Artificial Sequence
<220> FEATURE:
<223> OTHER INFORMATION: Peptide

<400> SEQUENCE: 181

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 182
<211> LENGTH: 18
<212> TYPE: PRT
<213> ORGANISM: Artificial Sequence
<220> FEATURE:
<223> OTHER INFORMATION: Peptide

<400> SEQUENCE: 182

Leu Leu Ile Ile Leu Arg Arg Arg Ile Arg Lys Gln Ala His Ala His
1               5                   10                  15

Ser Lys

<210> SEQ ID NO 183
<211> LENGTH: 21
<212> TYPE: PRT
<213> ORGANISM: Artificial Sequence
<220> FEATURE:
<223> OTHER INFORMATION: Peptide

<400> SEQUENCE: 183

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 184
<211> LENGTH: 18
<212> TYPE: PRT
<213> ORGANISM: Artificial Sequence
<220> FEATURE:
<223> OTHER INFORMATION: Peptide

<400> SEQUENCE: 184

Arg Gly Gly Arg Leu Ser Tyr Ser Arg Arg Arg Phe Ser Thr Ser Thr
1               5                   10                  15

Gly Arg

<210> SEQ ID NO 185
<211> LENGTH: 15
<212> TYPE: PRT
<213> ORGANISM: Artificial Sequence
<220> FEATURE:
<223> OTHER INFORMATION: Peptide
```

```
<400> SEQUENCE: 185

Ser Asp Leu Trp Glu Met Met Val Ser Leu Ala Cys Gln Tyr
1               5                   10                  15

<210> SEQ ID NO 186
<211> LENGTH: 12
<212> TYPE: PRT
<213> ORGANISM: Artificial Sequence
<220> FEATURE:
<223> OTHER INFORMATION: Peptide

<400> SEQUENCE: 186

Thr Ser Pro Leu Asn Ile His Asn Gly Gln Lys Leu
1               5                   10
```

METHODS AND COMPOSITIONS FOR INTERFERENCE WITH DNA POLYMERASE AND DNA SYNTHESIS

CROSS-REFERENCE TO RELATED APPLICATIONS

This application is a 371 application of International Application No. PCT/US2014/046275, filed Jul. 11, 2014, which claims benefit of U.S. Provisional Application No. 61/845,793, filed Jul. 12, 2013.

STATEMENT REGARDING FEDERALLY SPONSORED RESEARCH

This invention was made with government support under Grant No. R01GM095881 awarded by the National Institutes of Health (NIH). The government has certain rights in the invention.

FIELD OF THE INVENTION

The disclosed invention is generally in the field of regulation of DNA synthesis.

REFERENCE TO SEQUENCE LISTING

The Sequence Listing submitted on Apr. 22, 2016, as a text file named "GSURF 2013- 21_ST25.txt," created on Apr. 13, 2016, and having a size of 35,790 bytes is hereby incorporated by reference pursuant to 37 C.F.R § 1.52(e)(5).

BACKGROUND OF THE INVENTION

RNA participates widely in gene expression and regulation at the levels of transcription, mRNA maturation, and translation in cells (Fire et al., 1998; Mello & Conte, 2004; Ma et al., 2005; Macrae et al., 2006; Sudarsan et al., 2006; Cheah et al., 2007; Nagano et al., 2008; Guo et al., 2010; Heo & Sung, 2011; Wiedenheft et al., 2012). These observations are consistent with the RNA world hypothesis (Gesteland et al., 2006) and the preservation of functions of RNAs, such as ribosomal RNAs and the peptidyl transferase ribozyme (Nissen et al., 2000; Harms et al., 2001; Agmon, 2009; Fox et al., 2012). However, it is unknown whether RNA can directly influence DNA polymerase and synthesis both in vitro and in vivo, though the DNA synthesis in both prokaryotes and eukaryotes is highly regulated (Nishitani & Lygerou, 2002; Paulsson & Chattoraj, 2006).

Since dNTPs are constantly present in cells, regulation of the availability and level of the DNA precursors (dNTPs) is considered to be a major strategy in controlling DNA polymerization (Ji & Mathews, 1991; Chabes & Stillman, 2007; Rampazzo et al., 2010; Gon et al., 2011; Niida et al., 2011). Improper quantity and imbalance of dNTPs may hamper DNA polymerization and fidelity, leading to mutation, genomic instability, and even cell death (Elledge & Davis, 1990; Mathews & Ji, 1992; Zhao et al., 1998; Mathews, 2006). Clearly, tight control of the dNTP level helps regulating DNA synthesis in cells.

It is an object of the present invention to provide methods and compositions by which DNA synthesis is inhibited by RNA. It is also an object of the present invention to provide methods and compositions that inhibit cells and cell growth by inhibiting DNA synthesis. It is also an object of the present invention to provide methods and compositions for treating cancer by inhibiting cancer cells and cancer cell growth by inhibiting DNA synthesis.

BRIEF SUMMARY OF THE INVENTION

Disclosed are methods and compositions for inhibiting DNA synthesis in a cell. The method comprises bringing into contact RNA and the cell. The RNA can be any RNA, such as whole cell RNA, whole cell mRNA, whole cell ribosomal RNA, whole cell transfer RNA, synthetic RNA, recombinant RNA, modified RNA, or a combination. The RNA can be a complex mixture of sequences, a single sequence, or anywhere in between. The RNA can be fragments of various lengths, of similar lengths, of long lengths, of short lengths, or a combination. The amount of RNA can be sufficient to reduce or inhibit DNA synthesis in the cell.

The disclosed regulation of DNA synthesis by RNA can be used, for example, in analytical methods, as a research tool to affect cells under study, to synchronize cell cycle in a cell culture, and to inhibit cell growth.

In some forms, the cell can be a cell in a subject. In some forms, inhibition of DNA synthesis in the cell can inhibit the cell. In some forms, the cell can be a cancer cell. In some forms, inhibition of DNA synthesis in the cell can inhibit the cancer cell. In some forms, inhibition of DNA synthesis in the cell can inhibit growth of the cell. In some forms, inhibition of DNA synthesis in the cell can inhibit replication of the cell. In some forms, inhibition of DNA synthesis in the cell can kill the cell. In some forms, the RNA is administered to the subject. In some forms, the RNA can be brought into contact with the cell by targeting the RNA to the cell.

In some forms, the RNA can have a sequence complexity of 1,000 or more, 10,000 or more, or 100,000 or more. In some forms, the RNA can have a sequence complexity of 1,000 or less, 100 or less, or 10. In some forms, the RNA can consist essentially of sequences homologous to the cell. In some forms, the RNA does not functionally encode a protein.

In some forms, the RNA can be comprised in a composition. In some forms, the composition can further comprise a pharmaceutically acceptable carrier. In some forms, the composition can further comprise a targeting molecule. In some forms, the targeting molecule can be a tumor-targeting peptide.

Also disclosed are methods and compositions for treating cancer. The method comprises administering a composition to a subject diagnosed with cancer, where the composition comprises RNA, a targeting molecule, and a pharmaceutically acceptable carrier. In some forms, the targeting molecule can be a tumor-targeting peptide.

In some forms, the composition can comprise RNA and a pharmaceutically acceptable carrier. In some forms, the composition can comprise RNA, a targeting molecule, and a pharmaceutically acceptable carrier. In some forms, the composition can comprise RNA, a targeting molecule, and a pharmaceutically acceptable carrier, where the targeting molecule is a tumor-targeting peptide.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 3A, 3B, and 3C show the structure of deoxynucleoside triphosphate binding to DNA polymerase and the reaction mechanism of the deoxyribonucleoside triphosphate diphosphatase activity of DNA polymerase. (a) The active site of inosine triphosphate pyrophosphatase (or diphosphatase) in complex with ITP (PDB ID: 2Q16). (b) The alignment of the ddATP structure bound to the active site of DNA polymerase (PDB ID: 3EZ5) and the dATP hydrolysis model structure of the dNTP-DPase (the dATP and attacking water are in cyan). In the DNA polymerase structure (PDB ID: 3EZ5), the metal ions and coordinated water molecules are shown as light blue and red spheres, respectively. (c) The proposed mechanism of the dNTP-DPase transformed from DNA polymerase in the presence of RNA. The water molecule or 3'-HO can be activated as the nucleophile for attacking the incoming dNTP. Pyrophosphate is released as the by-product in each reaction. Pathway I: the dNTP hydrolysis because of the water activation and attack at the α-position of the incoming dNTP. Pathway II: the dNTP polymerization because of the 3'-OH activation and attack at the α-position of the incoming dNTP.

DETAILED DESCRIPTION OF THE INVENTION

Figure 1:
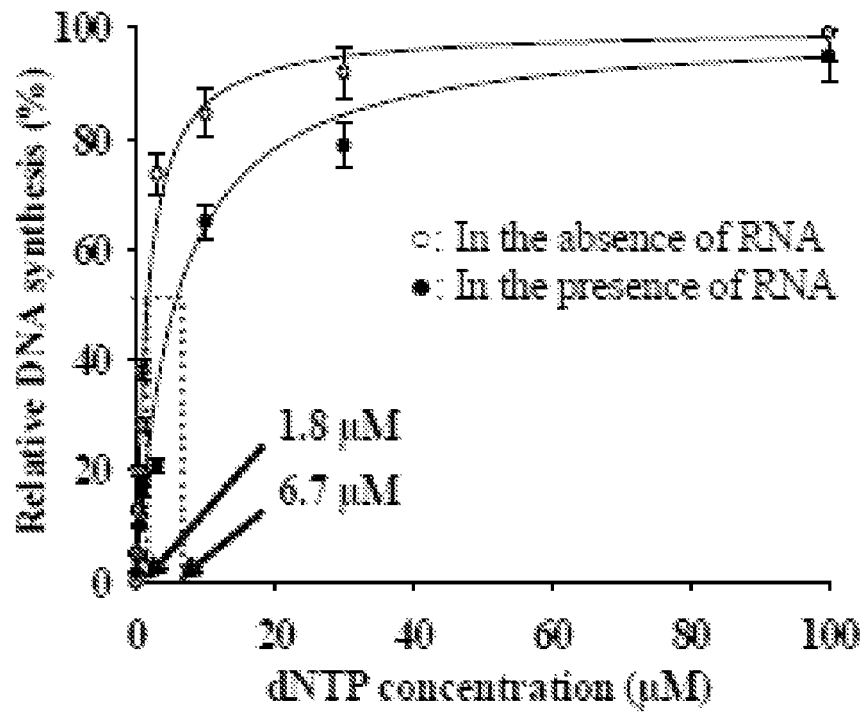
FIG. 1 is a graph of DNA synthesis versus concentration of deoxynucleoside triphosphates in the absence or presence of RNA.

The disclosed method and compositions may be understood more readily by reference to the following detailed description of particular embodiments and the Example included therein and to the Figures and their previous and following description.

RNA participates widely in gene expression regulation at the levels of transcription, mRNA maturation, and translation in cells. However, it was unknown whether RNA can directly participate in regulating DNA polymerization and replication. DNA synthesis in both prokaryotes and eukaryotes is a highly regulated process. The regulation of availability of DNA precursors (dNTPs) is considered to be a major strategy in controlling DNA polymerization and repair. Improper quantity and imbalance of dNTPs may hamper replication and fidelity, leading to mutation, genomic instability, and even cell death. Since dNTPs are constantly present in cells, tight control of dNTPs helps suppression of undesired DNA synthesis before and after the S phase in the cell cycle, where the RNA concentration may be higher than that in the S phase. A novel activity of DNA polymerases in the presence of RNA was discovered, which transforms DNA polymerases into deoxyribonucleoside triphosphate diphosphatase (dNTP-DPase) or pyrophosphatase. Upon binding to DNA polymerases, RNA turns them into the enzyme that hydrolyzes dNTPs into dNMPs and pyrophosphate. Both the polymerase transformation and the dNTP hydrolysis by the dNTP-DPase activity can inhibit DNA polymerization. This is the first observation of RNA interfering with DNA polymerase activity and DNA polymerization.

Cancer cells are in the constant DNA synthesis mode (or the S phase). Thus, the supply of DNA precursors (dNTPs) is very critical for cancer growth. The present discoveries on inhibition of dNTP availability can be generally applied to significantly suppress cancer DNA synthesis, thereby inhibiting tumor cell proliferation. The stimulation of the dNTP inhibition by the sequence-non-specific RNAs allows development of therapeutic RNA molecules that are stable in cellular environments and can be selectively delivered to the location for their specific anticancer activities. Because RNA-based DNA polymerase inhibition and activity conversion are broadly applicable to cells, these RNA molecules have general anticancer ability in treating various cancers.

Other methods of using interfering RNAs have completely different mechanisms on cell growth inhibition. They work on mRNA inactivation through specific binding (or blocking) and hydrolysis of mRNAs to prevent protein synthesis. The disclosed methods involve a strategy (or referred as inhibitive RNAs) that works on a much deeper level, which inhibits DNA synthesis, thereby preventing cell growth.

DNA synthesis and repair is selectively inhibited by the disclosed DNA synthesis-inhibitive RNAs. By conjugating the RNAs with compounds that can recognize specific proteins, such as specific proteins that appear in different phases of the cell cycle, in cancer cells and/or tumors, and/or in different stages of cancer development, the disclosed RNAs can be targeted to cells to be inhibited. The disclosed compositions can be used both for treatment of disease and for the study of cells and cell physiology, such as by affecting particular targeted cells or cell stages.

Disclosed are methods and compositions for inhibiting DNA synthesis in a cell. The method comprises bringing into contact RNA and the cell. The RNA can be any RNA, such as whole cell RNA, whole cell mRNA, whole cell ribosomal RNA, whole cell transfer RNA, synthetic RNA, recombinant RNA, modified RNA, or a combination. The RNA can be a complex mixture of sequences, a single sequence, or anywhere in between. The RNA can be fragments of various lengths, of similar lengths, of long lengths, of short lengths, or a combination. The amount of RNA can be sufficient to reduce or inhibit DNA synthesis in the cell. As used herein, "whole cell" refers to material or a component from or relating to most or all such material or component found or isolatable from unfractionated cells. That is, a whole cell component is produced without any special effort taken to fractionate some forms of the component from others.

The disclosed regulation of DNA synthesis by RNA can be used, for example, in analytical methods, as a research tool to affect cells under study, to synchronize cell cycle in a cell culture, and to inhibit cell growth.

In some forms, the cell can be a cell in a subject. In some forms, inhibition of DNA synthesis in the cell can inhibit the cell. In some forms, the cell can be a cancer cell. In some forms, inhibition of DNA synthesis in the cell can inhibit the cancer cell. In some forms, inhibition of DNA synthesis in the cell can inhibit growth of the cell. In some forms, inhibition of DNA synthesis in the cell can inhibit replication of the cell. In some forms, inhibition of DNA synthesis in the cell can kill the cell. In some forms, the RNA is administered to the subject. In some forms, the RNA can be brought into contact with the cell by targeting the RNA to the cell.

In some forms, the RNA can have a sequence complexity of 1,000 or more, 10,000 or more, or 100,000 or more. In some forms, the RNA can have a sequence complexity of 1,000 or less, 100 or less, or 10. In some forms, the RNA can consist essentially of sequences homologous to the cell. In some forms, the RNA does not functionally encode a protein.

In some forms, the RNA can be comprised in a composition. In some forms, the composition can further comprise a pharmaceutically acceptable carrier. In some forms, the composition can further comprise a targeting molecule. In some forms, the targeting molecule can be a tumor-targeting peptide.

Also disclosed are methods and compositions for treating cancer. The method comprises administering a composition to a subject diagnosed with cancer, where the composition comprises RNA, a targeting molecule, and a pharmaceutically acceptable carrier. In some forms, the targeting molecule can be a tumor-targeting peptide.

In some forms, the composition can comprise RNA and a pharmaceutically acceptable carrier. In some forms, the composition can comprise RNA, a targeting molecule, and a pharmaceutically acceptable carrier. In some forms, the composition can comprise RNA, a targeting molecule, and a pharmaceutically acceptable carrier, where the targeting molecule is a tumor-targeting peptide.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a RNA is disclosed and discussed and a number of modifications that can be made to a number of molecules including the RNA are discussed, each and every combination and permutation of the RNA and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. RNA

The disclosed compositions and methods use ribonucleic acid (RNA) as an active compound to affect DNA polymerase activity, cell growth, and cell cycling. The RNA can be any RNA, such as whole cell RNA, whole cell mRNA, whole cell ribosomal RNA, whole cell transfer RNA, synthetic RNA, recombinant RNA, modified RNA, or a combination. The nucleotide base sequence of the RNA is non-specific for use of the RNA as an active compound to affect DNA polymerase activity, cell growth, and cell cycling. That is, it is the chemical nature and chemical structure of the RNA that produces the effect and not any specific nucleotide sequence of the RNA. Thus, and in general, the nucleotide sequence of the RNA used in the disclosed compositions and methods is not important. However, it can be useful to use RNA that lacks some, most, or all sequence-specific properties or functions of RNA. For example, the RNA can lack functional sequences for translation initiation, translation termination, specific binding to ribosomal RNA or ribosomal proteins, specific binding to aminoacyl transferases, specific function of miRNAs, specific function of snRNAs, and specific function of siRNAs. In some forms, it can be useful to use RNA that has some sequence-specific properties or functions of RNA. For example, it can be useful to use RNA that can function as siRNA. This can be useful for providing two or more functions of the RNA on the cells, tissues, and subjects to which the RNA is administered.

RNA for use in the disclosed compositions and methods can have any sequence, length, and complexity. It has been discovered that the effect of RNA on DNA polymerase does not depend these features. Rather, the effect of RNA on DNA polymerase depends on the amount of RNA to which the DNA polymerase is exposed.

The RNA can be a natural RNA or RNA from a natural source. For example, the RNA can be whole cell RNA, whole cell mRNA, whole cell ribosomal RNA, whole cell transfer RNA, synthetic RNA, recombinant RNA, modified RNA, or a combination. Generally, RNA isolated from cells and tissues can be used regardless of the proportions or combinations of different types and sequences of RNA present. This can make production and preparation of RNA for use in the disclosed compositions and methods easier. However, natural RNA can also be processed, altered, fractionated, subdivided, etc. before use. In some embodiments, certain fractions and types of RNA can be used exclusively or preferentially. Techniques for isolating and fractionating different types of RNA are known and can be used to produce the disclosed RNA.

As used herein, "natural RNA" refers to RNA that is present in, isolated from, or directly derived from RNA that is naturally produced in a cell. The term "natural RNA" excludes RNA that is synthesized in vitro and RNA that is produced recombinantly. RNA that has or matches the sequence of natural RNA but that is produced in vitro, synthetically, recombinantly, or otherwise artificially is not considered to be "natural RNA" as that term is used herein.

The RNA can be artificial RNA. As used herein, "artificial RNA" refers to RNA that is not present in, isolated from, or directly derived from RNA that is naturally produced in a cell. The term "artificial RNA" includes RNA that is synthesized in vitro and RNA that is produced recombinantly. RNA that has or matches the sequence of natural RNA but that is produced in vitro, synthetically, recombinantly, or otherwise artificially is considered to be "artificial RNA" as that term is used herein. Thus, the term "artificial RNA" does not exclude RNA that has or matches the sequence of natural RNA but that is synthesized in vitro and RNA that is produced recombinantly.

The RNA can be synthetic RNA. As used herein, "synthetic RNA" refers to RNA that is synthesized in vitro. The synthesis can be chemical, enzymatic, or a combination. In some embodiments, enzymatic synthesis is preferred. The term "synthetic RNA" excludes RNA that is produced recombinantly. RNA that has or matches the sequence of natural RNA but that is produced synthetically is considered to be "synthetic RNA" as that term is used herein.

The RNA can be modified RNA. As used herein, "modified RNA" refers to nucleic acid that includes at least one nucleotide analog or nucleotide substitute. Nucleotide analogs are nucleotides that contain some type of modification to the base, sugar, or phosphate moieties. Nucleotide substitutes are nucleotides or nucleotide analogs that have had the phosphate moiety and/or sugar moieties replaced. Modified RNA, nucleotide analogs, and nucleotide substitutes are described in more detail elsewhere herein.

The RNA can be recombinant RNA. As used herein, "recombinant RNA" refers to RNA that is produced enzymatically from a recombinant or otherwise artificial construct enzymatically in cells or in vitro. In some embodiments, recombinant production in vitro is preferred. The term "recombinant RNA" excludes RNA that is produced synthetically. RNA that has or matches the sequence of natural RNA but that is produced recombinantly is considered to be "recombinant RNA" as that term is used herein.

Natural RNA, artificial RNA, synthetic RNA, and recombinant RNA can each be used alone or in any combination. In some embodiments, RNA of one type and source is preferred.

The RNA can be a complex mixture of sequences, a single sequence, or anywhere in between. For example, the RNA can be whole cell RNA, RNA all of the same sequence, a set of RNA molecules having two or more different sequences, or a combination. Whole cell RNA and whole cell mRNA generally are complex, heterogeneous mixtures of RNA molecules having numerous different sequences. Whole cell ribosomal RNA and whole cell transfer RNA generally are less complex, heterogeneous mixtures of RNA molecules having a number of different sequences.

The number of different nucleotide sequences represented in a mixture of nucleic acids is conventionally described as the complexity of the nucleic acid mixture. Complexity of nucleic acids is generally described in terms of the total length in nucleotides of the unique sequence present in the nucleic acid mixture. Whole cell RNA is made up of every type of RNA molecule produced in the cell and thus has a high complexity. As used herein, complexity of a nucleic acid (such as an RNA molecule) or a nucleic acid mixture (such as a mixture of RNA molecules) refers to the kinetic complexity of the RNA(s). Kinetic complexity is defined as the amount of nucleic acid measured in nucleotides needed so that every nucleotide sequence in the nucleic acid mixture is represented just once. Unless the context clearly indicates otherwise, reference to complexity of nucleic acid or RNA refers to kinetic complexity.

In some forms, the RNA can have a sequence complexity of 10 or more, 100 or more, 1,000 or more, 10,000 or more, or 100,000 or more. In some forms, the RNA can have a sequence complexity of 10,000 or less, 1,000 or less, 100 or less, or 10.

In some forms, the RNA can have a sequence complexity of from 6 to about 10, 15, 20, 25, 30, 40, 50, 60, 70, 80, 90, 100, 125, 150, 175, 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 10 to about 15, 20, 25, 30, 40, 50, 60, 70, 80, 90, 100, 125, 150, 175, 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 15 to about 20, 25, 30, 40, 50, 60, 70, 80, 90, 100, 125, 150, 175, 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 20 to about 25, 30, 40, 50, 60, 70, 80, 90, 100, 125, 150, 175, 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 30 to about 40, 50, 60, 70, 80, 90, 100, 125, 150, 175, 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 50 to about 60, 70, 80, 90, 100, 125, 150, 175, 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 60 to about 70, 80, 90, 100, 125, 150, 175, 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 80 to about 90, 100, 125, 150, 175, 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 90 to about 100, 125, 150, 175, 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 100 to about 125, 150, 175, 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 125 to about 150, 175, 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 150 to about 175, 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 175 to about 200, 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 200 to about 300, 400, 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 400 to about 500, 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 500 to about 750, 1,000, 2,000, 3,000, 4,000, 5,000, 7,500, 10,000, 20,000, 30,000, 40,000, 50,000, 75,000, or 100,000. In some forms, the RNA can have a sequence complexity of from about 750 to about 1,000, 2,000, 3,000, 4,000, 5,000, 7,500, 10,000, 20,000, 30,000, 40,000, 50,000, 75,000, or 100,000. In some forms, the RNA can have a sequence complexity of from about 1,000 to about 2,000, 3,000, 4,000, 5,000, 7,500, 10,000, 20,000, 30,000, 40,000, 50,000, 75,000, or 100,000. In some forms, the RNA can have a sequence complexity of from about 3,000 to about 4,000, 5,000, 7,500, 10,000, 20,000, 30,000, 40,000, 50,000, 75,000, or 100,000. In some forms, the RNA can have a sequence complexity of from about 4,000 to about 5,000, 7,500, 10,000, 20,000, 30,000, 40,000, 50,000, 75,000, or 100,000. In some forms, the RNA can have a sequence complexity of from about 5,000 to about 7,500, 10,000, 20,000, 30,000, 40,000, 50,000, 75,000, or 100,000. In some forms, the RNA can have a sequence complexity of from about 7,500 to about 10,000, 20,000, 30,000, 40,000, 50,000, 75,000, or 100,000. In some forms, the RNA can have a sequence complexity of from about 10,000 to about 20,000, 30,000, 40,000, 50,000, 75,000, or 100,000. In some forms, the RNA can have a sequence complexity of from about 20,000 to about 30,000, 40,000, 50,000, 75,000, or 100,000. In some forms, the RNA can have a sequence complexity of from about 30,000 to about 40,000, 50,000, 75,000, or 100,000. In some forms, the RNA can have a sequence complexity of from about 40,000 to about 50,000, 75,000, or 100,000. In some forms, the RNA can have a sequence complexity of from about 50,000 to about 75,000, or 100,000. In some forms, the RNA can have a sequence complexity of from about 75,000 to about 100,000.

The length of RNA molecules used is not critical. The RNA can be fragments of various lengths, of similar lengths, of long lengths, of short lengths, or a combination. For example, the RNA molecules can be 6, 10, 15, 20, 25, 30, 40, 50, 60, 70, 80, 90, 100, 125, 150, 175, 200, 300, 400, 500, 750, or 1,000 nucleotides in length. This can be, for example, the average or median length of the RNA molecules. In some forms, the RNA molecules can be from 6 to about 10, 15, 20, 25, 30, 40, 50, 60, 70, 80, 90, 100, 125, 150, 175, 200, 300, 400, 500, 750, or 1,000 nucleotides in length. In some forms, the RNA can be from about 10 to about 15, 20, 25, 30, 40, 50, 60, 70, 80, 90, 100, 125, 150, 175, 200, 300, 400, 500, 750, or 1,000 nucleotides in length. In some forms, the RNA can be from about 15 to about 20, 25, 30, 40, 50, 60, 70, 80, 90, 100, 125, 150, 175, 200, 300, 400, 500, 750, or 1,000 nucleotides in length. In some forms, the RNA can be from about 20 to about 25, 30, 40, 50, 60, 70, 80, 90, 100, 125, 150, 175, 200, 300, 400, 500, 750, or 1,000 nucleotides in length. In some forms, the RNA can be from about 30 to about 40, 50, 60, 70, 80, 90, 100, 125, 150, 175, 200, 300, 400, 500, 750, or 1,000 nucleotides in length. In some forms, the RNA can be from about 50 to about 60, 70, 80, 90, 100, 125, 150, 175, 200, 300, 400, 500, 750, or 1,000 nucleotides in length. In some forms, the RNA can be from about 60 to about 70, 80, 90, 100, 125, 150, 175, 200, 300, 400, 500, 750, or 1,000 nucleotides in length. In some forms, the RNA can be from about 80 to about 90, 100, 125, 150, 175, 200, 300, 400, 500, 750, or 1,000 nucleotides in length. In some forms, the RNA can be from about 90 to about 100, 125, 150, 175, 200, 300, 400, 500, 750, or 1,000 nucleotides in length. In some forms, the RNA can be from about 100 to about 125, 150, 175, 200, 300, 400, 500, 750, or 1,000 nucleotides in length. In some forms, the RNA can be from about 125 to about 150, 175, 200, 300, 400, 500, 750, or 1,000 nucleotides in length. In some forms, the RNA can be from about 150 to about 175, 200, 300, 400, 500, 750, or 1,000 nucleotides in length. In some forms, the RNA can be from about 175 to about 200, 300, 400, 500, 750, or 1,000 nucleotides in length. In some forms, the RNA can be from about 200 to about 300, 400, 500, 750, or 1,000 nucleotides in length. In some forms, the RNA can be from about 400 to about 500, 750, or 1,000 nucleotides in length. In some forms, the RNA can be from about 500 to about 750 or 1,000 nucleotides in length. In some forms, the RNA can be from about 750 to about 1,000 nucleotides in length.

It is preferred that the RNA have a complexity of between 6 and 30 nucleotides, be made up of copies of a single type of RNA molecule (that is, a RNA molecule of the same length and sequence).

The amount of RNA can be sufficient to reduce or inhibit DNA synthesis in the cell. For example, the RNA can be from about 1 ng/kg to about 1 g/kg. The amount of RNA can be adjusted based on such factors as half like of the RNA in the subject, the percent or amount of the RNA that reaches the target cells or tissue, and the effectiveness of the RNA on DNA synthesis in the target cells.

In some forms, the RNA can consist essentially of sequences homologous to the cell. As used in this context, "sequences homologous to the cell" refers to sequences that are present in natural RNA or DNA of the referenced cell. The RNA that is homologous to the cell can be natural RNA, artificial RNA, synthetic RNA, modified RNA, or recombinant RNA. Thus, being homologous to the cell refers to the sequence present in the RNA and not to the manner in which the RNA is produced.

In some forms, the RNA does not functionally encode a protein, by which is meant, the RNA does not include a substantial open reading frame, does not include functional translation control sequences or elements, or a combination.

1. Modified RNA

The RNA can be or include modified RNA. The disclosed RNA can be made up of for example, nucleotides, nucleotide analogs, or nucleotide substitutes. RNA will typically be made up of A, C, G, and U. For use in the disclosed compositions and methods, it is useful for the RNA to be made up of nucleotide analogs that reduce the degradation of the RNA in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein.

Many modified nucleotides are known and can be used in the disclosed RNA. A nucleotide analog is a nucleotide which contains some type of modification to the base, sugar, or phosphate moieties. Modifications to nucleotides are well known in the art and would include for example, 5-methylcytosine (5-Me-C), 5-hydroxymethyl cytosine, xanthine, hypoxanthine, and 2-aminoadenine as well as modifications at the sugar or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference in its entirety, and specifically for their description of base modifications, their synthesis, their use, and their incorporation into oligonucleotides and nucleic acids.

Nucleotide analogs can also include modifications of the sugar moiety. Modifications to the sugar moiety would include natural modifications of the ribose and deoxyribose as well as synthetic modifications, such as the sugar-locked nucleic acids. Sugar modifications include but are not limited to the following modifications at the 2' position: OH; F; O-, S-, Se-, or N-alkyl; O-, S-, Se-, or N-alkenyl; O-, S-, Se-, or N-alkynyl; or O-alkyl-O-alkyl, wherein the alkyl, alkenyl and alkynyl can be substituted or unsubstituted C1 to C10, alkyl or C2 to C10 alkenyl and alkynyl. 2' sugar modifications also include but are not limited to —O[($CH_2$)n O]m $CH_3$, —O($CH_2$)n $OCH_3$, —O($CH_2$)n $NH_2$, —O($CH_2$)n $CH_3$, —O($CH_2$)n-$ONH_2$, and —O($CH_2$)nON[($CH_2$)n $CH_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, $SCH_3$, $SeCH_3$, OCN, Cl, Br, CN, $CF_3$, $OCF_3$, $SOCH_3$, $SO_2CH_3$, $SeOCH_3$, $SeO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications can also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs can also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety, and specifically for their description of modified sugar structures, their synthesis, their use, and their incorporation into nucleotides, oligonucleotides and nucleic acids.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference its entirety, and specifically for their description of modified phosphates, their synthesis, their use, and their incorporation into nucleotides, oligonucleotides and nucleic acids.

It is understood that nucleotide analogs need only contain a single modification, but can also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to (base pair to) complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference its entirety, and specifically for their description of phosphate replacements, their synthesis, their use, and their incorporation into nucleotides, oligonucleotides and nucleic acids.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science 254:1497-1500 (1991)).

The disclosed RNA can be made up of different types of nucleotides or the same type of nucleotides. For example, one or more of the nucleotides in a RNA can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. Such RNAs can be referred to as chimeric RNAs.

B. Targeting Molecules

By including or associating a targeting molecule or targeting peptide with the RNA composition, the RNA composition can be targeted or can target the target of the targeting molecule or targeting peptide. In this way, the RNA composition can be said to target the target of the targeting molecule or targeting peptide. For convenience and unless otherwise indicated, reference to targeting of a RNA composition or other compound or composition is intended to indicate that the RNA composition or other compound or composition includes or is associated with an appropriate targeting molecule or targeting peptide.

The targeting molecule can selectively target tumor tissue, cancer, wounded tissue, regenerating tissue, sites of injury, surgical sites, sites of angiogenesis, sites of inflammation, sites of arthritis, lung tissue, pulmonary arterial hypertension lung vasculature, pulmonary arterial hypertension lesions, remodeled pulmonary arteries, or interstitial space of lungs. The RNA composition can selectively target wounded tissue, regenerating tissue, sites of injury, surgical sites, sites of angiogenesis, sites of inflammation, sites of arthritis, lung tissue, pulmonary arterial hypertension lung vasculature, pulmonary arterial hypertension lesions, remodeled pulmonary arteries, or interstitial space of lungs.

The disclosed RNA compositions can, for example, target brain cells, brain stem cells, brain tissue, and/or brain vasculature, kidney cells, kidney stem cells, kidney tissue, and/or kidney vasculature, skin cells, skin stem cells, skin tissue, and/or skin vasculature, lung cells, lung tissue, and/or lung vasculature, pancreatic cells, pancreatic tissue, and/or pancreatic vasculature, intestinal cells, intestinal tissue, and/or intestinal vasculature, adrenal gland cells, adrenal tissue, and/or adrenal vasculature, retinal cells, retinal tissue, and/or retinal vasculature, liver cells, liver tissue, and/or liver vasculature, prostate cells, prostate tissue, and/or prostate vasculature, endometriosis cells, endometriosis tissue, and/or endometriosis vasculature, ovary cells, ovary tissue, and/or ovary vasculature, bone cells, bone tissue, and/or bone vasculature, bone marrow cells, bone marrow tissue, and/or bone marrow vasculature, cartilage cells, cartilage tissue, and/or cartilage vasculature, stem cells, embryonic stem cells, pluripotent stem cells, induced pluripotent stem cells, adult stem cells, hematopoietic stem cells, neural stem cells, mesenchymal stem cells, mammary stem cells, endothelial stem cells, olfactory adult stem cells, neural crest stem cells, cancer stem cells, blood cells, erythrocytes, platelets, leukocytes, granulocytes, neutrophils, eosinphils, basophils, lymphoid cells, lymphocytes, monocytes, wound vasculature, vasculature of injured tissue, vasculature of inflamed tissue, atherosclerotic plaques, or a combination.

Targeting of cancer and tumors is well known (Wu et al., Targeted Therapy for Cancer, J. Cancer Molecules 2(2):57-66 (2006). Tumor targeting generally relies on tumor antigens expressed on the cell surface that serve as target devices for ligands containing different kinds of effector molecules. In these approaches, drugs can actively target tumors using tumor-specific MoAbs or peptide ligands binding to receptors that are present on tumor cells.

Examples of targeting molecules and targeting peptides are known. Useful peptides for tumor targeting include, for example, RGD, CAR, LyP-1, NGR, and RGR peptides. The prototypic tumor-targeting peptide is RGD. CAR has tumor-penetrating properties. This peptide has a unique target within tumors; it preferentially accumulates in the hypoxic/low nutrient areas of tumors (Laakkonen et al., Nature Med. 8:751-755 (2002); Laakkonen et al., Proc Natl Acad Sci USA 101: 9381-9386 (2004); Karmali et al., Nanomedicine, 5:73-82 (2009)). CRGRRST (RGR; SEQ ID NO:185; Joyce et al., Cancer Cell 4:393-403 (2003)) is a peptide that has been successfully used in targeting a cytokine antibody combination into tumors (Hamzah et al., J. Clin. Invest. 118:1691-1699, (2008)). This peptide is linear, which simplifies the synthesis. NGR peptides target angiogenic vasculature, including angiogenic vasculature associated with tumors, and $\alpha_v$ integrin and $\alpha_5\beta_1$ integrin (U.S. Pat. Nos. 6,576,239 and 6,177,542 and U.S. Patent Application Publication No. 20090257951).

Tumors and cancer can be targeted using tumor blood vessel targeting peptide such as: CNGRC (SEQ ID NO:9) and other peptides with the NGR motif (U.S. Pat. Nos. 6,177,542 and 6,576,239; U.S. Patent Application Publication No. 20090257951); RGD peptides, and RGR peptides. Other tumor targeting peptides include CSRPRRSEC (SEQ ID NO:10), CSRPRRSVC (SEQ ID NO:11) and CSRPRR-SWC (SEQ ID NO:12) (Hoffman et al., Cancer Cell, vol. 4 (2003)), F3 (KDEPQRRSARLSAKPAPPKPEPKPKKA-PAKK; (SEQ ID NO:13)), PQRRSARLSA (SEQ ID NO:14), PKRRSARLSA (SEQ ID NO:15) (U.S. Pat. No. 7,544,767), and CGRECPRLCQSSC (SEQ ID NO:16).

RGD peptides are peptides that contain the RGD (Arg-Gly-Asp) motif and that target angiogenesis and tumor vasculature. NGR peptides are peptides that contain the NGR (Asn-Gly-Arg) motif and that target angiogenesis and tumor vasculature. Examples of NGR peptides include CNGRCVSGCAGRC (SEQ ID NO:17), NGRAHA (SEQ ID NO:18), CVLNGRMEC (SEQ ID NO:19), and CNGRC (SEQ ID NO:20). GSL peptides are peptides that contain the GSL (Gly-Ser-Leu) motif and that target tumor vasculature. Examples of a GSL peptide include CGSLVRC (SEQ ID NO:21) and CLSGSLSC (SEQ ID NO:22).

Useful NGR peptides include peptide such as $X_2CNGRCX_2$ (SEQ ID NO:23), $CX_2(C/X)NGR(C/X)X_2C$ (SEQ ID NO:24), and $CNGRCX_6$ (SEQ ID NO:25) (where "X" is any amino acid), which can be linear or circular. Examples of NGR peptides include CNGRCVSGCAGRC (SEQ ID NO:26), NGRAHA (SEQ ID NO:27), CVLNGRMEC (SEQ ID NO:28), CNGRC (SEQ ID NO:29), ALNGREESP (SEQ ID NO:30), CVLNGRME (SEQ ID NO:31), CKVCNGRCCG (SEQ ID NO:32), CEMCNGRCMG (SEQ ID NO:33), CPLCNGRCAL (SEQ ID NO:34), CPTCNGRCVR (SEQ ID NO:35), CGVCNGRCGL (SEQ ID NO:36), CEQCNGRCGQ (SEQ ID NO:37), CRNCNGRCEG (SEQ ID NO:38), CVLCNGRCWS (SEQ ID NO:39), CVTCNGRCRV (SEQ ID NO:40), CTECNGRCQL (SEQ ID NO:41), CRTCNGRCLE (SEQ ID NO:42), CETCNGRCVG (SEQ ID NO:43), CAVCNGRCGF (SEQ ID NO:44), CRDLNGRKVM (SEQ ID NO:45), CSCCNGRCGD (SEQ ID NO:46), CWGCNGRCRM (SEQ ID NO:47), CPLCNGRCAR (SEQ ID NO:48), CKSCNGRCLA (SEQ ID NO:49), CVPCNGRCHE (SEQ ID NO:50), CQSCNGRCVR (SEQ ID NO:51), CRTCNGRCQV (SEQ ID NO:52), CVQCNGRCAL (SEQ ID NO:53), CRCCNGRCSP (SEQ ID NO:54), CASNNGRVVL (SEQ ID NO:55), CGRCNGRCLL (SEQ ID NO:56), CWLCNGRCGR (SEQ ID NO:57), CSKCNGRCGH (SEQ ID NO:58), CVWCNGRCGL (SEQ ID NO:59), CIRCNGRCSV (SEQ ID NO:60), CGECNGRCVE (SEQ ID NO:61), CEGVNGRRLR (SEQ ID NO:62), CLSCNGRCPS (SEQ ID NO:63), CEVCNGRCAL (SEQ ID NO:64).

Other examples of targeting peptides include: Brain targeting peptides such as: CNSRLHLRC (SEQ ID NO:65), CENWWGDVC (SEQ ID NO:66), WRCVLREGPAGGCAWFNRHRL (SEQ ID NO:67), CLSSRLDAC (SEQ ID NO:68), CVLRGGRC (SEQ ID NO:69), CNSRLQLRC (SEQ ID NO:70), CGVRLGC (SEQ ID NO:71), CKDWGRIC (SEQ ID NO:72), CLDWGRIC (SEQ ID NO:73), CTRITESC (SEQ ID NO:74), CETLPAC (SEQ ID NO:75), CRTGTLFC (SEQ ID NO:76), CGRSLDAC (SEQ ID NO:77), CRHWFDVVC (SEQ ID NO:78), CANAQSHC (SEQ ID NO:79), CGNPSYRC (SEQ ID NO:80), YPCGGEAVAGVSSVRTMCSE (SEQ ID NO:81), LNCDYQGTNPATSVSVPCTV (SEQ ID NO:82); kidney targeting peptides such as: CLPVASC (SEQ ID NO:83), CGAREMC (SEQ ID NO:84), CKGRSSAC (SEQ ID NO:85), CWARAQGC (SEQ ID NO:86), CLGRSSVC (SEQ ID NO:87), CTSPGGSC (SEQ ID NO:88), CMGRWRLC (SEQ ID NO:89), CVGECGGC (SEQ ID NO:90), CVAWLNC (SEQ ID NO:91), CRRFQDC (SEQ ID NO:92), CLMGVHC (SEQ ID NO:93), CKLLSGVC (SEQ ID NO:94), CFVGHDLC (SEQ ID NO:95), CRCLNVC (SEQ ID NO:96), CKLMGEC (SEQ ID NO:97); skin targeting peptides such as: CARSKNKDC (SEQ ID NO:98), CRKDKC (SEQ ID NO:99), CVALCREACGEGC (SEQ ID NO:100), CSSGCSKNCLEMC (SEQ ID NO:101), CIGEVEVC (SEQ ID NO:102), CKWSRLHSC (SEQ ID NO:103), CWRGDRKIC (SEQ ID NO:104), CERVVGSSC (SEQ ID NO:105), CLAKENVVC (SEQ ID NO:106); lung targeting peptides such as: CGFECVRQCPERC (SEQ ID NO:107), CGFELETC (SEQ ID NO:108), CTLRDRNC (SEQ ID NO:109), CIGEVEVC (SEQ ID NO:110), CGKRYRNC (SEQ ID NO:111), CLRPYLNC (SEQ ID NO:112), CTVNEAYKTRMC (SEQ ID NO:113), CRLRSYGTLSLC (SEQ ID NO:114), CRPWHNQAHTEC (SEQ ID NO:115); pancreas targeting peptides such as: SWCEPGWCR (SEQ ID NO:116), CKAAKNK (SEQ ID NO:117), CKGAKAR (SEQ ID NO:118), VGVGEWSV (SEQ ID NO:119); intestine targeting peptides such as: YSGKWGW (SEQ ID NO:120); uterus targeting peptides such as: GLSGGRS (SEQ ID NO:121); adrenal gland targeting peptides such as: LMLPRAD (SEQ ID NO:122), LPRYLLS (SEQ ID NO:123); retina targeting peptides such as: CSCFRDVCC (SEQ ID NO:124), CRDVVSVIC (SEQ ID NO:125); gut targeting peptides such as: YSGKWGK (SEQ ID NO:126), GISALVLS (SEQ ID NO:127), SRRQPLS (SEQ ID NO:128), MSPQLAT (SEQ ID NO:129), MRRDEQR (SEQ ID NO:130), QVRRVPE (SEQ ID NO:131), VRRGSPQ (SEQ ID NO:132), GGRGSWE (SEQ ID NO:133), FRVRGSP (SEQ ID NO:134), RVRGPER (SEQ ID NO:135); liver targeting peptides such as: VKSVCRT (SEQ ID NO:136), WRQNMPL (SEQ ID NO:137), SRRFVGG (SEQ ID NO:138), ALERRSL (SEQ ID NO:139), ARRGWTL (SEQ ID NO:140); prostate targeting peptides such as: SMSIARL (SEQ ID NO:141), VSFLEYR (SEQ ID NO:142), RGRWLAL (SEQ ID NO:143); ovary targeting peptides such as: EVRSRLS (SEQ ID NO:144), VRARLMS (SEQ ID NO:145), RVGLVAR (SEQ ID NO:146), RVRLVNL (SEQ ID NO:147); clot binding targeting peptide such as: CREKA (SEQ ID NO:148), CLOT1, and CLOT2; heart targeting peptides such as: CRPPR (SEQ ID NO:149), CGRKSKTVC (SEQ ID NO:150), CARPAR (SEQ ID NO:151), CPKRPR (SEQ ID NO:152), CKRAVR (SEQ ID NO:153), CRNSWKPNC (SEQ ID NO:154), RGSSS (SEQ ID NO:155), CRSTRANPC (SEQ ID NO:156), CPKTRRVPC (SEQ ID NO:157), CSGMARTKC (SEQ ID NO:158), GGGVFWQ (SEQ ID NO:159), HGRVRPH (SEQ ID NO:160), VVLVTSS (SEQ ID NO:161), CLHRGNSC (SEQ ID NO:162), CRSWNKADNRSC (SEQ ID NO:163), CGRKSKTVC (SEQ ID NO:164), CKRAVR (SEQ ID NO:165), CRNSWKPNC (SEQ ID NO:166), CPKTRRVPC (SEQ ID NO:167), CSGMARTKC (SEQ ID NO:168), CARPAR (SEQ ID NO:169), and CPKRPR (SEQ ID NO:170).

Targeting molecules can also be defined by their targets. For example, numerous antigens and proteins are known that can be useful for targeting. Any molecule that can bind, selectively bind, target, selectively, target, selectively target, etc. such target molecules can be used as a targeting molecule. For example, antibodies, nucleic acid aptamers, and compounds that can bind to target molecules can be used as targeting molecules. Examples of useful target molecules for targeting molecules include αv integrins, αvβ3 integrin, αvβ5 integrin, α5β1 integrin, aminopeptidase N, tumor endothelial markers (TEMs), endosialin, p32, gC1q receptor, annexin-1, nucleolin, fibronectin ED-B, fibrin-fibronectin complexes, interleukin-11 receptor a, and protease-cleaved collagen IV. These and other examples are described and referred to in Ruoslahti et al., J. Cell Biology, 2010 (doi: 10.1083/jbc.200910104), which is hereby incorporated by reference in its entirety and specifically for its description of and references to target molecules.

The RNA composition can comprise any number of targeting molecules. By way of example, the RNA composition, can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more targeting molecules. The RNA composition, can also comprise any number in between those numbers listed above.

It is understood that, although many targeting and targeting motifs and sequences are shown with cysteine residues at one or both ends, such cysteine residues are generally not required for targeting function. Generally, such cysteines are present due to the methods by which the targeting and targeting sequences were identified. Such terminal cysteines can be used to, for example, circularize peptides, such as those disclosed herein. For these reasons, it is also understood that cysteine residues can be added to the ends of any of the disclosed peptides.

Many targeting molecules and targeting peptides target to the vasculature of the target tissue. However, for the sake of convenience targeting is referred to in some places herein as targeting to the tissue associated with the vasculature to which the targeting molecule or targeting peptide may actually target. Thus, for example, a targeting peptide that targets tumor vasculature can be referred to herein as targeting to tumor tissue or to tumor cells.

C. Internalization Elements

The disclosed RNA compositions can comprise one or more internalization elements. Internalization elements can be incorporated into or fused with other peptide components of the composition, such as peptide targeting molecules. Internalization elements are molecules, often peptides or amino acid sequences, that allow the internalization element and components with which it is associated, to pass through biological membranes. "Internalization" refers to passage through a plasma membrane or other biological barrier. Internalization elements include, for example, cell-penetrating peptides (CPPs) and CendR peptides. Peptides that are internalized into cells are commonly referred to as cell-penetrating peptides. There are two main classes of such peptides: hydrophobic and cationic (Zorko and Langel, Adv Drug Deliv Rev. 57:529-45 (2005)). The cationic peptides, which are commonly used to introduce nucleic acids, proteins into cells, include the prototypic cell-penetrating peptides (CPP), Tat, and penetratin (Derossi et al., Trends Cell Biol. 8, 84-7 (1998); Meade and Dowdy, Advanced Drug Delivery Reviews. 59(2-3):134-40 (2007)). A herpes virus protein, VP22, is capable of both entering and exiting cells and carrying a payload with it (Elliott and O'Hare, 1997; Brewis et al., Mol. Ther. 7, 262-270 (2003)). CendR peptides are described in U.S. Patent Application Publication No. 2010/0322862.

Internalization elements can comprise an amino acid sequence of a protein selected from a group consisting of Antennapedia, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol and BGTC (Bis-Guanidinium-Tren-Cholesterol. Table 1 shows some examples of internalization elements.

TABLE 1

Internalization Elements

| Name | Sequence | SEQ ID NO |
|---|---|---|
| Antp | RQPKIWFPNRRKPWKK | (SEQ ID NO: 171) |
| HIV-Tat | GRKKRRQRPPQ | (SEQ ID NO: 172) |
| Penetratin | RQIKIWFQNRRMKWKK | (SEQ ID NO: 173) |
| Antp-3A | RQIAIWFQNRRMKWAA | (SEQ ID NO: 174) |
| Tat | RKKRRQRRR | (SEQ ID NO: 175) |
| Buforin II | TRSSRAGLQFPVGRVHRLLRK | (SEQ ID NO: 176) |
| Transportan | GWTLNSAGYLLGKINKALAALAKKIL | (SEQ ID NO: 177) |
| model amphipathic peptide (MAP) | KLALKLALKALKAALKLA | (SEQ ID NO: 178) |
| K-FGF | AAVALLPAVLLALLAP | (SEQ ID NO: 179) |
| Ku70 | VPMLK-PMLKE | (SEQ ID NO: 180) |
| Prion | MANLGYWLLALFVTMWTDVGLCKKRPKP | (SEQ ID NO: 181) |
| pVEC | LLIILRRRIRKQAHAHSK | (SEQ ID NO: 182) |
| Pep-1 | KETWWETWWTEWSQPKKKRKV | (SEQ ID NO: 183) |
| SynB1 | RGGRLSYSRRRFSTSTGR | (SEQ ID NO: 184) |
| Pep-7 | SDLWEMMMVSLACQY | (SEQ ID NO: 185) |
| HN-1 | TSPLNIHNGQKL | (SEQ ID NO: 186) |
| BGSC (Bis-Guanidinium-Spermidine-Cholesterol) | | |

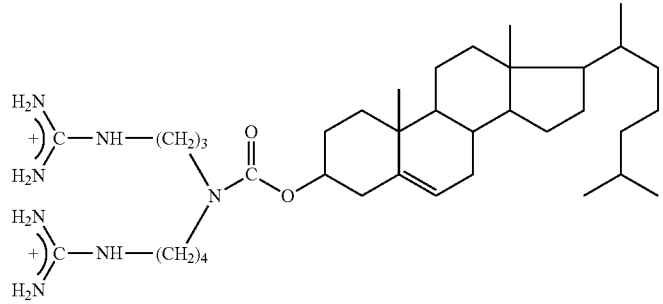

BGSC

TABLE 1-continued

Internalization Elements

| Name | Sequence | SEQ ID NO |
|---|---|---|
| BGTC (Bis-Guanidinium-Tren-Cholesterol) | BGTC structure | |

The disclosed RNA compositions can further comprise the amino acid sequence SEQ ID NO:171, SEQ ID NO:172 (Bucci, M. et al. 2000. Nat. Med. 6, 1362-1367), SEQ ID NO:173 (Derossi, D., et al. 1994. Biol. Chem. 269, 10444-10450), SEQ ID NO:174 (Fischer, P. M. et al. 2000. J. Pept. Res. 55, 163-172), SEQ ID NO:175 (Frankel, A. D. & Pabo, C. O. 1988. Cell 55, 1189-1193; Green, M. & Loewenstein, P. M. 1988. Cell 55, 1179-1188), SEQ ID NO:176 (Park, C. B., et al. 2000. Proc. Natl Acad. Sci. USA 97, 8245-8250), SEQ ID NO:177 (Pooga, M., et al. 1998. FASEB J. 12, 67-77), SEQ ID NO:178 (Oehlke, J. et al. 1998. Biochim. Biophys. Acta. 1414, 127-139), SEQ ID NO:179 (Lin, Y. Z., et al. 1995. J. Biol. Chem. 270, 14255-14258), SEQ ID NO:180 (Sawada, M., et al. 2003. Nature Cell Biol. 5, 352-357), SEQ ID NO:181 (Lundberg, P. et al. 2002. Biochem. Biophys. Res. Commun 299, 85-90), SEQ ID NO:182 (Elmquist, A., et al. 2001. Exp. Cell Res. 269, 237-244), SEQ ID NO:183 (Morris, M. C., et al. 2001. Nature Biotechnol. 19, 1173-1176), SEQ ID NO:184 (Rousselle, C. et al. 2000. Mol. Pharmacol. 57, 679-686), SEQ ID NO:185 (Gao, C. et al. 2002. Bioorg. Med. Chem. 10, 4057-4065), or SEQ ID NO:186 (Hong, F. D. & Clayman, G. L. 2000. Cancer Res. 60, 6551-6556). The disclosed RNA compositions can further comprise BGSC (Bis-Guanidinium-Spermidine-Cholesterol) or BGTC (Bis-Guanidinium-Tren-Cholesterol) (Vigneron, J. P. et al. 1998. Proc. Natl. Acad. Sci. USA. 93, 9682-9686).

D. Endosome Escape Signals

Endosome escape signals are compounds and compositions, including, for example, polymers and sequences, that, in response to a change in pH, are able to cause disruption or lysis of an endosome or provide for escape of a normally membrane-impermeable compound, such as a polynucleotide or protein, from a cellular internal membrane-enclosed vesicle, such as an endosome or lysosome. Endosomal release is important for the delivery of a wide variety of molecules which are endocytosed but incapable of diffusion across cellular membranes. Endosome escape signals undergo a shift in their physico-chemical properties over a physiologically relevant pH range (usually pH 5.5-8). This shift can be a change in the compound's solubility, ability to interact with other compounds, and a shift in hydrophobicity or hydrophilicity. Exemplary endosome escape signals can have pH-titratable groups or pH-labile groups or bonds. As used herein, pH-titratable groups reversibly accept or donate protons in water as a function of pH under physiological conditions, i.e. a pH range of 4-8. pH-titratable groups have $pK_a$'s in the range of 4-8 and act as buffers within this pH range. Thus, pH-titratable groups gain or lose charge in the lower pH environment of an endosome. Groups titratable at physiological pH can be determined experimentally by conducting an acid-base titration and experimentally determining if the group buffers within the pH-range of 4-8. Examples of groups that can exhibit buffering within this pH range include but are not limited to: carboxylic acids, imidazole, N-substituted imidazole, pyridine, phenols, and polyamines An example of an amino acid useful in endosome escape signals is histidine. Compounds with pH-titratable groups may disrupt internal vesicles by the so-called proton sponge effect. A reversibly masked membrane active compound, wherein the masking agents are attached to the compound via pH labile bonds, can therefore be considered to be an endosome escape signal.

A subset of endosome escape compounds is fusogenic compounds, including fusogenic peptides. Fusogenic peptides can facilitate endosomal release of agents such as oligomeric compounds to the cytoplasm. It is believed that fusogenic peptides change conformation in acidic pH, effectively destabilizing the endosomal membrane thereby enhancing cytoplasmic delivery of endosomal contents. Example fusogenic peptides include peptides derived from polymyxin B, influenza HA2, GALA, KALA, EALA, melittin and melittin-derived peptides, Alzheimer β3-amyloid peptide, and the like. Surface charge reversal of compounds and compositions (from anionic to cationic) selectively in the acidic pH of endosomes and lysosomes is a mechanism for rapid endosomal and lysosomal escape of compounds and compositions. One of the strategies developed to facilitate endosomal escape mimics the fusion of viral envelopes with host cell endosomal membranes, which occurs during viral infections. Several synthetic fusogenic peptides have been synthesized based on the fusion domain of the influenza virus. Oliveira et al. (Fusogenic peptides enhance endosomal escape improving siRNA-induced silencing of oncogenes, International J. Pharmaceuticals 331(2):211-214 (2007)) evaluated the effects of the influenza-derived fusogenic peptide diINF-7 on gene silencing efficiency of siRNA targeting the epidermal growth factor receptor (EGFR) and the K-ras oncogenes. For both targets, strong enhancement of gene silencing activity was noted after addition of diINF-7 fusogenic peptide, identifying endosomal escape as a limiting factor for siRNA silencing efficiency.

E. RNA Compositions

The disclosed RNA can be administered and delivered to target tissues and cells in compositions. These RNA compositions can be formulated to, for example, protect the RNA from degradation or elimination, increase the half-life of the RNA in the subject, aid in internalization of the RNA into cells and tissues, and other properties useful for pharmaceutical compositions. In addition to protecting the RNA, RNA compositions can also be formulated to target the RNA to particular tissues and cells, as well as internalization of the RNA into cells and tissues. Targeting of the RNA compositions can be accomplished by including one or more targeting molecules as part of the RNA composition. Internalization of the RNA can be accomplished by including one or more internalization elements as part of the RA composition.

Compositions and pharmaceutical formulations are provided for administering a therapeutically effective amount of one or more nucleic acids to a subject, individual, or patient in need thereof. The formulations can be administered in any one or more of a variety of forms, such as solutions, suspensions, tablets, dispersible tablets, pills, capsules, powders, delayed and/or sustained release formulations, or elixirs for oral administration, or in sterile solutions or suspensions for parenteral administration. The formulations can contain one or more nucleic acids and/or one or more nucleic acid carriers as described below. In some embodiments the carriers can be targeted to specific cells either based upon the size of the carriers or based upon the presence of targeting molecules. In some embodiments the carriers can deliver the nucleic acid to the cytosol of targeted cells. In some embodiments carriers can deliver the nucleic acid to the nucleus of targeted cells.

1. Nucleic Acid Carrier Compositions

The delivery of any therapeutic compound to a subject, individual, or patient in need thereof can be impeded by any one or several factors such as limited ability of the compound to reach a target cell or tissue, or by restricted entry or trafficking of the compound within cells. Typically, nucleic acid drugs should be delivered into the corresponding intracellular target site, i.e. the nucleus or cytosol. Because biosystems have developed several barriers to prevent the intrusion of external genetic material, the nucleic acids can be combined with sophisticated delivery machinery to overcome those barriers. Many nucleic acids are stable for only limited times in cells or plasma. However, compositions described herein can stabilize nucleic acids, which can then be dispersed for cellular delivery. The compositions can contain one or more nucleic acid carriers, each carrier independently containing one or more nucleic acids for delivery. The compositions can be prepared in many suitable formulations for administration to a subject, individual, or patient in need thereof.

Numerous carriers have been developed, for example those in the areas of molecular cloning and gene therapies, for the delivery of nucleic acids such as DNA, RNA, and synthetic or semi-synthetic derivatives of DNA and RNA. The carriers described herein can be used to deliver the disclosed RNA. Conventional carriers include vectors such as viral vectors, plasmid vectors, cosmids, and artificial chromosomes. Non-viral carriers include those based on lipids, polymers, and inorganic materials. Delivery can in some embodiments be accomplished using modified nucleic acids such as derivatives designed to resist enzymatic degradation and/or nucleic acid conjugates including conjugates of nucleic acids with polymers, lipids, targeting molecules, internalization elements, or combinations thereof. Nonviral carriers can have the benefit of low immune response and easy large-scale production. Although nonviral carriers can have lower efficacy of delivery compared with some viral vectors, they can have a higher maximum tolerant dose (MTD) that can result in appreciable in vivo efficacy.

i. Biological Barriers to Delivery

Most nucleic acid drugs are biologically active only after their uptake into cells. The disclosed RNA is intended to function in the nucleus of cells. To access the final target site, the nucleic acid drugs overcome several barriers that biosystems have developed for protection from invasion by external microorganisms and exogenous genetic material.

After injection into the blood stream, most low molecular weight drugs are rapidly excreted by the kidney because the cut-off value of the glomerular filtration is around 20,000 Da (Seymour, et al., *J Biomed Mater Res* 1987, 21:1341-1358). In some embodiments increasing the molecular weight of the delivery vehicle can increase blood level concentrations and efficacy of delivery. In some embodiments the carrier has a mass greater than about 20,000 Da, greater than about 40,000 Da, greater than about 80,000 Da, greater than about 100,000 Da, or greater than about 200,000 Da. The mass of the carriers, including viral vectors and non-viral vectors such as lipids, nucleic acid conjugates, and polymeric and inorganic nanoparticles can be designed to have any mass to allow for efficacy of delivery. In some embodiments, the carriers described herein protect the nucleic acids from degradation or digestions by extracellular nucleases.

Particles with a diameter of over 300 nm were previously observed to be rapidly trapped by the reticuloendothelial system (RES) in the liver, spleen, and lung before they reached the target tissue (Ikomi et al., *Radiology* 1995, 196:107-113). By carefully controlling the properties of the carriers, i.e. molecular weight and charge density and by controlling the particle formation, the diameter of the carriers can be controlled. In some embodiments the carriers are provided with a mean geometric diameter less than about 500 nm, less than about 400 nm, less than about 300 nm, less than about 275 nm, less than about 250 nm, less than about 225 nm, or less than about 200 nm. In some embodiments the mean geometric diameter of the carrier is about 60 nm, 75 nm, 100 nm, 125 nm, 150 nm, 175 nm, 200 nm, 225 nm, 250 nm, 275 nm, 300 nm, 325 nm, or 350 nm. In some embodiments, the mean geometric diameter is between 75 and 250 nm or between 50 and 300 nm. In some embodiments, 30%, 40%, 50%, 60%, 70%, 80%, 90%, or more of the carriers of a population of carriers have a diameter that is less than 300 nM. In some embodiments, 10%, 20%, 30%, 40%, 50%, 60%, 70%, 80%, 90%, or more of the carriers of a population of carriers have a diameter that is greater than 50 nm but less than 300 nm.

In some embodiments, controlling the charge of the carrier is desired to improve the efficacy of delivery. Because most serum proteins have net negative charges, cationic carriers may form aggregates with serum proteins such as albumin. These aggregates may accumulate in organs with fine capillary structures such as the lung, skin, or intestine and can block the blood stream (Pouton et al., *Adv Drug Deliv Rev* 2001, 46:187-203). However, carriers with too strong a negative surface charge may be removed from the blood stream by nonparenchymal cells such as Kupffer cells in the liver (Hashida, et al. *J. Control. Release* 1996, 41:91-97). In some embodiments the aggregate formation is prevented by carriers having a surface charge less than about +500 mV, less than about +400 mV, less than about +300 mV, less than about +200 mV, less than about +100 mV, less than about +50 mV, less than about +30 mV, or less than 0 mV. Elimination by nonparenchymal cells can in some embodiments be prevented by a carrier having a surface charge greater than about −500 mV, greater than about −400 mV, greater than about −300 mV, greater than about −200 mV, greater than about −100 mV, greater than about −50 mV, greater than about −30 mV, or greater than about 0 mV. In some embodiments the carriers can have a surface charge between −100 mV and +100 mV, between −50 mV and +50 mV, between −30 mV and +30 mV, or between −15 mV and +15 mV. Therefore, careful control of both the surface charge and size of carriers can in some embodiments be employed for overcoming extracellular barriers efficiently. In some embodiments the efficacy of delivery can be greatly improved in carriers having a mass greater than about 20,000 Da, a diameter less than about 250 nm, and a surface charge between about −30 mV and +30 mV.

Although hydrophobic small molecules typically diffuse freely into the cytosol, charged molecules may have difficulty penetrating through the plasma membrane, which is composed of a lipid bilayer. Highly negatively charged nucleic acid drugs, such as the disclosed RNA, may have even more difficulty interacting with the plasma membrane, which has an extracellular surface with many negative charges due to the high content of anionic glycosylated membrane proteins. Most carriers can be internalized into cells via the endocytosis, phagocytosis, or macropinocytosis pathways (Conner et al., *Nature* 2003, 422:37-44). Larger particles with a diameter of approximately 1-10 μm can be internalized by phagocytosis or macropinocytosis.

Endocytosis is classified into receptor-mediated endocytosis and nonspecific endocytosis on the basis of ligand-receptor interaction. Various ligands induce the receptor-mediated endocytosis, which can enhance the specificity of the delivery into target cells. On the other hand, nonspecific endocytosis mediates the internalization of nucleic acid drug carriers without any ligand. In many cases, nonspecific endocytosis can be induced by the electrostatic interaction between the delivery carriers and proteoglycans on the surface of the plasma membrane (Mislick et al., *Proc. Nat. Acad. Sci. USA* 1996, 93:12349-12354). Cationic carriers can interact more effectively with proteoglycans having negatively charged sulfate or carboxylate groups, so that they generally show higher endocytic efficiency than anionic carriers. Depending on the mechanism, endocytosis can also be classified into clathrin-mediated endocytosis (See Schmid, *Annu Rev Biochem* 1997, 66:511-548), caveolin-mediated endocytosis (See Pelkmans et al., *Traffic* 2002, 3:311-320), and clathrin- and caveolin-independent endocytosis (See Damke et al., *J. Cell. Biol.* 1995, 131:69-80).

In endocytosis, the endosome is gradually acidified by ATPases in the endosomal membrane. The acidification proceeds from the normal physiological pH value of 7.4 to the lysosomal pH value of 4.8. The fully acidified endosome will fuse with a lysosome. Successful delivery of intact nucleic acids in the cytosol can be improved by carriers that escape the endosome at the early stage of acidification prior to degradation or deactivation. In some embodiments effective delivery of intact nucleic acids to the cytosol is accomplished with carriers that escape the endosome at pH greater than about 5, at a pH greater than about 5.5, at a pH greater than about 6.0, or at a pH greater than about 6.5.

The disclosed RNA are preferably delivered through the cytosol into the nucleus. Cytosol is not a simple liquid phase that enables free diffusion of macromolecules, but a gel-like phase with a fine mesh structure primarily composed of actin filaments. The diffusion rate of large molecules over a hydrodynamic diameter of 85 nm is significantly lower than that of small molecules in cytosol. The cytosolic concentration of free DNA has been previously shown in some cases to rapidly decrease, with a half-life of 90 min, by the action of nucleases preventing the invasion of viral DNA or RNA (See Lechardeur et al., *Gene* 1999; 6:482-497). Hence, protection of nucleic acids to nuclease attack can enhance delivery to the nucleus without loss of activity. Viruses are actively and rapidly transported through the cystol by microtubule filaments. In some embodiments, carriers are delivered near the nuclear envelope quickly (i.e. within about 30 minutes) by mimicking active viral transport. In some embodiments the carrier results in a half-life of the nucleic acid in the cystol of greater than 120 minutes, greater than 180 minutes, or greater than 240 minutes. The carrier can in some embodiments result in a half-life of the nucleic acid in the cystol that is from about 240 to about 1,800 minutes, from about 240 to about 1,000 minutes, or from about 360 to about 600 minutes. In some embodiments the carrier delivers the nucleic acid through the cystol and into the nucleus in less than 45 minutes, less than 40 minutes, less than 35 minutes, less than 30 minutes, less than 25 minutes, or less than 20 minutes.

The final stage in nucleic acid delivery to the nucleus is penetration through the nuclear envelope. Along with the plasma membrane and the endosomal membrane, the double bilayer structure of the nuclear envelope can be one of the main barriers to nucleic acid delivery. The nuclear pore complex (NPC) controls the transport of macromolecules between the cytosol and nucleoplasm, but the passive diffusion cut-off value of the NPC is about 9 nm, so that it is difficult for large macromolecules such as free pDNA or polymer-pDNA complexes to enter the nucleus by passive diffusion through the NPC. The macromolecules can, however, enter into the nucleoplasm during mitosis, when the nuclear envelope disintegrates. The open state of the NPC facilitates the active transport of particles less than about 26 nm, therefore successful delivery of nucleic acids into the nucleus can be accomplished by the conjugation of the nucleus localization signal (NLS), which binds to importin, that controls transport of nuclear proteins. In other embodiments carriers overcome the barrier of nuclear entry using a carbohydrate-binding receptor, lectin, or through direct disruption of the nuclear envelope.

Examples of nuclear targeting molecules are described in, for example, U.S. Patent Application Publication Nos. 10100143454, 20100099627, 20090305329, 20090176710, 20090087899, 20070231862, 20070212332, 20060242725, 20060233807, 20060147922, 20060070133, 20060051315, 20050147993, 20050071088, 20030166601, 20030125283, 20030083261, 20030003100, 20020068272, and 20020055174, which are hereby incorporated by reference in their entirety and specifically for their description of nuclear targeting molecules and motifs.

ii. Conventional Vectors

Conventional vectors, for example those often used in cloning, typically consist of a DNA or RNA molecule used as a vehicle to carry foreign genetic material into cells. In general, a conventional vector is a nucleic acid molecule (typically DNA or RNA) that serves to transfer a passenger nucleic acid (i.e., DNA or RNA) into a host cell. In some embodiments the carrier is a conventional vector, for example a viral vector. Although vectors can be used to deliver nucleic acids intended to be expressed in cells, the disclosed RNA will not be expressed. Thus, the vector does not or need not promote replication or expression of the nucleic acid. For example, conventional vectors that do not promote insertion or replication of the genetic material can deliver nucleic acid drugs. In some embodiments a conventional vector, such as a viral vector, can contain cleavable bonds to release the nucleic acid within the cell. For example, conventional vectors can be modified with one or more hydrolysable bonds to promote delivery and release of the nucleic acid.

Viruses such as adenovirus, adeno-associated virus (AAV), and retrovirus have developed very sophisticated mechanisms for the delivery of their genomes into host cells. In some embodiments the viral machinery can be used as an efficient vehicle for delivering nucleic acid, if the expression of the original viral genes can be prevented. It has been reported that even modified viral carriers may induce excessive immune response because they still contain viral capsid proteins on the surface. Therefore, in some embodiments, the carrier is not a viral carrier. One skilled in the art will understand how to determine if a particular viral carrier has induced an immune response, and the level of immune response considered excessive can be considered in view of the therapeutic effect.

In some embodiments, the carrier can be a viral vector. Exemplary viral vectors that can be modified to deliver a nucleic acid include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; and WO 91/02805), alphavirus-based vectors (e.g., Sindbis vims vectors, Semliki forest virus (ATCC VR-67; ATCC VR-1247), Ross River virus (ATCC VR.-373; ATCC VR-1246) and Venezuelan equine encephalitis virus (ATCC VR-923; ATCC VR-1250; ATCC VR 1249; ATCC VR-532), adeno-associated vims (AAV) vectors (see, e.g., WO 94/12649, WO 93/03769; WO 93/19191; WO 94/28938; WO 95/11984 and WO 95/00655), and poxviras-based vectors (e.g., fowlpox, vaccinia, etc.). RNA viruses are preferred viral vectors for the disclosed RNA compositions.

Delivery of these vectors to the subject can be accomplished by methods appropriate to the viral vector selected, and according to methods well known in the art (e.g., administration by injection (e.g., intramuscular, subcutaneous, intravenous, and the like), oral administration, etc.) In some embodiments the viral vector contains one or more cleavable bonds to release the nucleic acid within the cell.

iii. Liposomal Carriers

In some embodiments the carrier is a liposomal carrier (i.e. a liposome), such as a stealth liposome or contain one or more lipids. In some embodiments, the liposome is a surface modified liposome. In some embodiments, the liposome comprises poly (ethylene glycol) lipids (PEG-modified, or long-circulating liposomes or stealth liposomes). In some embodiments, the carrier is a di-lipid amino acid (DILA$^2$). See U.S. patent application Ser. No. 12/114,284. In some embodiments, the liposomal carrier includes a Krebs Cycle analog such as those described in WO 2011/031561 A2.

Liposomes are vesicles with an aqueous interior enclosed by one or more phospholipid bilayers. Such vesicles have demonstrated utility as vehicles for delivering therapeutic and/or diagnostic agents to target tissues or organs. The liposomes are formed by methods known in the art from one or more vesicle-forming lipids. The term "vesicle-forming lipids" should be understood to mean lipids that are capable of forming liposome vesicles. See, e.g., U.S. Pat. No. 5,225,212. Exemplary vesicle-forming lipids include phosphatidyl-choline (PC), phosphatidylserine (PS), phosphatidylinositol (PI), cholesterylhemisuccinate (CHEMS), phosphatidylethanolamine (PE), oleic acid (OA), phosphatidic acid (PA), phosphatidylglycerol (PG), monosialoganglioside (GM1), phosphatidylethanolamine coupled to polyethylene glycol (PEG-PE, available from Avanti Polar Lipids, Birmingham, Ala.) and cholesterol.

In some embodiment the liposomal carrier is a pH-sensitive liposome. pH-sensitive liposomes that destabilize at acidic pH are particularly advantageous. In some embodiments pH-sensitive liposomes decompose at a pH less than about 6, less than about 5.5, less than about 5.0, or less than about 4.5.

The liposomes disclosed herein can be constructed to be pH-sensitive by including a pH-sensitive lipid in the liposome formulation. A pH sensitive liposome refers to a liposome which is designed and constructed so that the liposome structure decomposes (e.g., due to destabilization of the bilayer) when the liposome is exposed to a pH that differs from the pH at which the liposome was constructed. In general, pH sensitive liposomes can include the above-identified vesicle-forming lipids plus one or more pH-sensitive lipids. The term "pH-sensitive lipid", as used herein, generally refers to a lipid which contains a polar end (that is negatively charged at neutral pH) and a non-polar end. The polar end of the pH-sensitive lipid is in the unprotonated form at a first, higher pH but is in the protonated form at a second, lower pH. In some embodiments the pH-sensitive lipid is unprotonated at a pH greater than about 6.0, greater than about 6.5, greater than about 7.0, or at a pH of about 7.4. In some embodiments the pH-sensitive lipid is protonated at pH less than bout 6.5, less than about 6.0, less than about 5.5, less than about 5.0, or at a pH of about 4.8. Preferably the pH-sensitive lipid is protonated at a pH of about 6.0 or less. At the second, more acidic pHs, protonation of the polar end of the pH-sensitive lipid destabilizes the polar bilayer and thus, destabilizes the liposome. pH-sensitive lipids include molecules which are naturally occurring (e.g., oleic acid) or synthetic (e.g., diacyl-glycerol-3-succinate, Avanti Polar Lipids, Birmingham, Ala.).

In some embodiments, the liposomal carrier includes one or more acid-labile linkers, one or more hydrolysable linkers, or combinations thereof. Examples of acid-labile linkers include linkers containing an orthoester group, a hydrazone, a cis-acetonyl, an acetal, a ketal, a silyl ether, a silazane, an imine, a citraconic anhydride, a maleic anhydride, a crown ether, an azacrown ether, a thiacrown ether, a dithiobenzyl group, a cis-aconitic acid, a cis-carboxylic alkatriene, methacrylic acid, and mixtures thereof. Examples of acid-labile groups and linkers are given in U.S. Pat. Nos. 7,098,032; 6,897,196; 6,426,086; 7,138,382; 5,563,250; and 5,505,931. Examples of hydrolysable linkers or groups are given in U.S. Pat. Nos. 6,849,272; 6,200,599.

Exemplary lipids include, but are not limited to, 1,2-dioleoyl-sn-glycero-3-phosphatidylcholine (DOPC), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), lysophosphatidylcholine, dilinoleoylphosphatidylcholine distearoylphophatidylethanolamine ("DSPE"), dimyristoyl phosphatidylethanolamine ("DMPE"), dipalmitoyl phosphatidylethanolamine ("DPPE"), palmitoyloeoyl phosphatidylethanolamine ("POPE"), lysophosphatidylethanolamine, phosphatidylserine, phosphatidylglycerol, dimyristoyl phosphatidylserine ("DMPS"), dipalmitoyl phosphatidylserine ("DPPS"), brain phosphatidylserine ("BPS"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), dioleoylphosphatidylglycerol ("DOPG"), cholesterol or polyethyleneglycol (PEG).

iv. Nanoparticle Carriers

In some embodiments the carrier can be a particle or a nanoparticle. The particles can be polymeric or a nonpolymeric. Methods of making and loading particles and nanoparticles are known in the art.

In some embodiments the nanoparticle is a polymeric particle. A wide variety of polymers and methods for forming particles therefrom are known in the art of drug delivery. In some embodiments, the matrix of a polymeric particle comprises one or more polymers. Polymers can be natural or unnatural (synthetic) polymers. Polymers can be homopolymers or copolymers comprising two or more monomers. In terms of sequence, copolymers can be random, block, or comprise a combination of random and block sequences. The polymers can in some embodiments be linear polymers or branched polymers. In some embodiments polymeric particles are prepared from dendrimers.

In some embodiments, polymers include polymers which have been approved for use in humans by the U.S. Food and Drug Administration (FDA) under 21 C.F.R. §177.2600, including but not limited to polyesters (e.g. polylactic acid, poly(lactic-co-glycolic acid), polycaprolactone, polyvalerolactone, poly(1,3-dioxan-2one)); polyanhydrides (e.g. poly (sebacic anhydride)); polyethers (e.g., polyethylene glycol); polyurethanes; polymethacrylates; polyacrylates; and polycyanoacrylates.

Examples of polymers include polyethylenes, polycarbonates (e.g. poly(1,3-dioxan-2one)), polyanhydrides (e.g. poly(sebacic anhydride)), polyhydroxyacids (e.g. poly(β-hydroxyalkanoate)), polypropylfumerates, polycaprolactones, polyamides (e.g. polycaprolactam), polyacetals, polyethers, polyesters (e.g. polylactide, polyglycolide), poly (orthoesters), polycyanoacrylates, polyvinyl alcohols, polyurethanes, polyphosphazenes, polyacrylates, polymethacrylates, polyureas, polystyrenes, and polyamines.

In some embodiments, polymers can be hydrophilic. For example, polymers can comprise anionic groups (e.g. phosphate group, sulphate group, carboxylate group); cationic groups (e.g. quaternary amine group); or polar groups (e.g. hydroxyl group, thiol group, amine group).

In some embodiments, polymers can be modified with one or more moieties and/or functional groups. Any moiety or functional group can be used in accordance with the present invention. In some embodiments, polymers can be modified with polyethylene glycol (PEG), with a carbohydrate, and/or with acyclic polyacetals derived from polysaccharides (Papisov, 2001, ACS Symposium Series, 786:301). In some embodiments, polymers can be modified with a lipid or fatty acid group.

In some embodiments, polymers can be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include polyhydroxyacids; PEGylated polymers and copolymers of lactide and glycolide (e.g. PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly (ethylene imine), PEGylated poly(ethylene imine), poly(L-lactide-co-L-lysine), poly(serine ester), poly(4-hydroxy-L-proline ester), poly[α-(4-aminobutyl)-L-glycolic acid], and derivatives thereof.

In some embodiments, a polymer can be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers can be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer can comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines. Exemplary cationic polymers include pollysines, polyalkylimides, poly(amidoamines) and other amino acid derived polymers. Exemplary polylysines include poly-L-lysine, poly-D-lysine, racemic Poly-DL-lysine, derivatives thereof and copolymers thereof. Poly (amidoamines) (PAA) are a family of synthetic polymers characterized by the presence of tertiary amine groups and amide groups arranged regularly along the structure of the polymer. They can be synthesized in a controlled fashion to provide well defined polymers and dendrimers.

In some embodiments condensation with charged polymers shields the nucleic acid from nuclease digestion. In some embodiments the ratio (w/w) of nucleic acid to polymer is about 2:1, 1:1, 0.9:1, 0.8:1, 0.7:1, 0.6:1, 0.5:1, 0.4:1, 0.3:1, 0.2:1, or about 0.1:1. In some embodiments the amine-to-phosphate (N:P) ratio or the positive-t-negative charge ratio is greater than 1. In some embodiments the N:P ratio or the positive-to-negative charge ratio is about 1.1:1, 1.2:1, 1.3:1, or about 1.4:1. In some embodiments the cationic polymer is conjugated to a hydrophobic moiety. For example, the cationic polymer can be conjugated with a lipid moiety. Exemplary moieties include cholesterol, lauric acid, and myristic acid. In some embodiments the cationic polymers can be conjugated with temperature sensitive polymers or oligomers. Polymers or oligomers with a hydrophilic-hydrophobic transition below body temperature conjugated to cationic polymers can be optimized the strongly condense nucleic acids at body temperatures.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633). Poly(4-hydroxy-L-proline ester) was recently demonstrated to condense plasmid DNA through electrostatic interactions, and to mediate gene transfer (Putnam et al., 1999, Macromolecules, 32:3658; and Lim et al., 1999, J. Am. Chem. Soc., 121:5633). These new polymers are less toxic than poly(lysine) and PEI, and they degrade into non-toxic metabolites.

In some embodiments the particles can be inorganic particles. A co-precipitation of DNA with calcium phosphate (CaP particles) with varying chemical compositions was shown to provide DNA-containing CaP particles with successful transfection to mammalian cells (Chen et al., 1987, Mol. Cell. Biol. 2745-2752). The inorganic particles can be prepared by co-precipitation with one or more pharmaceutically acceptable salts, including those formed as pharmaceutically acceptable acid addition salts, metal salts, ammonium salts, organic amine addition salts, amino acid addition salts, and the like. Inorganic acid salts can include hydrochlorides, sulfates, nitrates, and phosphates. Organic acid salts can include acetates, maleates, fumarates, citrates, methanesulfonates, oxalates, malonates, succinates, and tartarates. Metal salts can include alkali metal salts, e.g., sodium salts and potassium salts; alkaline-earth metal salts, e.g., magnesium salts and calcium salts; aluminum salts; zinc salts; and the like. Ammonium salts can include ammonium, tetraethylammonium, and the like. Organic amine salts can include salts of morpholine, piperidine, and the like. Amino acid salts can include salts of glycine, phenylalanine, lysine, asparatic acid, glutamic acid, and the like. Exemplary inorganic particles include calcium phosphate particles, calcium chloride particles, and the like. In some embodiments the particles are inorganic particles stabilized by one or more organic polymers or co-precipitated with one or more organic polymers.

2. Pharmaceutical Formulations

The disclosed compositions can be formulated into suitable pharmaceutical preparations such as solutions, suspensions, tablets, dispersible tablets, pills, capsules, powders, delayed and/or sustained release formulations, or elixirs for oral administration, or in sterile solutions or suspensions for parenteral administration. In certain embodiments the disclosed compositions containing a therapeutically effective amount of nucleic acids are formulated into pharmaceutical compositions using techniques and procedures known in the art. It is understood that a therapeutically effective amount will depend upon multiple factors including but not limited to the type of formulation and route of administration; the specific disease or disorder to be treated; the presence, amount, and efficacy of additional therapeutic agents in the composition; among others. In the case of the disclosed RNA compositions, the effective amount can be an amount that effectively delivers an amount of RNA to the nucleus of target cells such that DNA polymerization is inhibited. For example, the RNA can be from about 1 ng/kg to about 1 g/kg. The amount of RNA can be adjusted based on such factors as half like of the RNA in the subject, the percent or amount of the RNA that reaches the target cells or tissue, and the effectiveness of the RNA on DNA synthesis in the target cells.

In some embodiments, the disclosed compositions can be formulated for single dosage administration. To formulate a composition, the weight fraction of active agent(s) (e.g., the disclosed RNA) is dissolved, suspended, dispersed or otherwise mixed in a selected carrier at an effective concentration such that the treated condition is relieved or one or more symptoms are ameliorated. The disclosed active agent(s) can be included in the pharmaceutically acceptable carrier in an amount sufficient to exert a therapeutically useful effect in the absence of undesirable side effects on the patient treated. The therapeutically effective concentration is determined empirically by testing the compounds in in vitro, ex vivo and in vivo systems, and then extrapolated therefrom for dosages for subjects. The concentration of active agent(s) in the pharmaceutical composition will depend on absorption, inactivation and excretion rates of the active compound, the physicochemical characteristics of the agent, the dosage schedule, and amount administered as well as other factors known to those of skill in the art.

Dosage forms or compositions containing active agent(s) in the range of 0.005% to 100% with the balance made up from non-toxic carrier can be prepared. Methods for preparation of these compositions are known to those skilled in the art. The contemplated compositions can contain 0.001%-100% active ingredient, or in one embodiment 0.1-95%.

Methods for solubilizing active agents or improving bioavailability can be used. Such methods are known to those of skill in this art, and include, but are not limited to, using cosolvents, such as dimethylsulfoxide (DMSO), using surfactants, such as TWEEN®, or dissolution in aqueous sodium bicarbonate. The pharmaceutical compositions of one or more of the active agents can be incorporated into a polymer matrix, for example, hydroxypropylmethyl cellulose, gel, permeable membrane, osmotic system, multilayer coating, microparticle, nanoparticle, liposome, microsphere, nanosphere, or the like. The active agent(s) can be suspended in micronized or other suitable form or can be derivatized (e.g., by adding one or more polyethylene glycol chains) to produce a more soluble active product or improve bioavailability.

Liquid pharmaceutically administrable compositions can, for example, be prepared by dissolving, dispersing, or otherwise mixing the active agent(s) and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Oral pharmaceutical dosage forms can be either solid, gel, or liquid. The solid dosage forms can be tablets, capsules, granules, and bulk powders. Types of oral tablets include compressed, chewable lozenges and tablets which can be enteric-coated, sugar-coated or film-coated. Capsules can be hard or soft gelatin capsules, while granules and powders can be provided in non-effervescent or effervescent form with the combination of other ingredients known to those skilled in the art.

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating.

The active agent(s), or a pharmaceutically acceptable salt(s) thereof, can be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents.

In all embodiments of tablets and capsules, the tablet and capsule formulations can be coated as known by those of skill in the art in order to modify or sustain dissolution of the active ingredient. Thus, for example, they can be coated with a conventional enterically digestible coating, such as phenylsalicylate, waxes, and cellulose acetate phthalate.

The pharmaceutical composition can be in a parenteral administration form. Injectables can be prepared in conventional forms, either as liquid solutions or suspensions, solid forms suitable for solution or suspension in liquid prior to injection, or as emulsions. The injectables, solutions, and emulsions can also contain one or more excipients. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. The percentage of active compound contained in such parenteral compositions is highly dependent on the specific nature thereof, as well as the activity of the compound and the needs of the subject.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

The unit-dose parenteral preparations can be packaged in an ampoule, a vial or a syringe with a needle. All preparations for parenteral administration should be sterile, as is known and practiced in the art. The injectable compositions described herein can be optimized for local and/or systemic administration.

Implantation of a slow-release or sustained-release system, such that a constant level of dosage is maintained is also contemplated herein. In such cases, the active agent(s) provided herein can be dispersed in a solid matrix optionally coated with an outer rate-controlling membrane. The compound diffuses from the solid matrix (and optionally through the outer membrane) sustained, rate-controlled release. The solid matrix and membrane can be formed from any suitable material known in the art including, but not limited to, polymers, bioerodible polymers, and hydrogels.

Lyophilized powders can be reconstituted for administration as solutions, emulsions and other mixtures. They can also be reconstituted and formulated as solids or gels. The sterile, lyophilized powder can be prepared by dissolving nucleic acids or nucleic acid carriers. The solvent can contain an excipient which improves the stability or other pharmacological component of the powder or reconstituted solution, prepared from the powder. The solvent can also contain a buffer, such as citrate, sodium or potassium phosphate or other such buffer known to those of skill in the art at. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The disclosed nucleic acids and carriers can be formulated to be targeted to a particular tissue, receptor, or other area of the body of the subject to be treated. Many such targeting methods are well known to those of skill in the art. In one embodiment, liposomal suspensions, including tissue-targeted liposomes, such as tumor-targeted liposomes, can also be suitable as pharmaceutically acceptable carriers. These can be prepared according to methods known to those skilled in the art.

Compositions can be formulated to provide immediate or delayed release of one or more of the active agent(s), including nucleic acids or nucleic acid carriers. Also disclosed are sustained release formulations to maintain therapeutically effective amounts of a nucleic acid over a period of time. In compositions containing multiple active agents, the active agents can be individually formulated to control the duration and/or time release of each active agent.

Such sustained and/or timed release formulations can be made by sustained release means of delivery devices that are well known to those of ordinary skill in the art. These pharmaceutical compositions can be used to provide slow or sustained release of one or more of the active agents using, for example, hydroxypropylmethyl cellulose, other polymer matrices, gels, permeable membranes, osmotic systems, multilayer coatings, microparticles, nanoparticles, liposomes, microspheres, nanospheres or the like. The active agents can also be suspended, micronized, or derivatized to vary release of the active ingredient(s).

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist". One that decreases, or prevents, a known activity is an "antagonist".

The term "inhibit" means to reduce or decrease in activity or expression. This can be a complete inhibition or activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "monitoring" as used herein refers to any method in the art by which an activity can be measured.

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that includes the knowledge that the subject is ill, or will be ill, as the result of a condition that is treatable by the compounds of the invention.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

A cell can be in vitro. Alternatively, a cell can be in vivo and can be found in a subject. A "cell" can be a cell from any organism including, but not limited to, a bacterium.

In one aspect, the compounds described herein can be administered to a subject comprising a human or an animal including, but not limited to, a mouse, dog, cat, horse, bovine or ovine and the like, that is in need of alleviation or amelioration from a recognized medical condition.

By the term "effective amount" of a compound as provided herein is meant a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compounds or compositions according to the methods described herein can be determined by evaluating the particular aspects of the medical history, signs, symptoms, and objective laboratory tests that are known to be useful in evaluating the status of a subject in need of treatment of cancer or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

F. Mixtures

Disclosed are mixtures formed by performing or preparing to perform the disclosed method. Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

EXAMPLES

Example 1

RNA Interference with DNA Polymerase and Synthesis

RNA can regulate many biological activities, including transcription and translation in cells. However, it was unknown whether RNA can directly affect DNA polymerization. It was discovered that RNA can directly interfere with DNA synthesis by altering DNA polymerase activity and turning DNA polymerase into deoxyribonucleoside triphosphate diphosphatase (dNTP-DPase). This example details the discovery and analysis of these effects of RNA on DNA polymerases. It was found that DNA polymerases of the A, B, C, and X families generally have similar dNTP-DPase activity. Moreover, it was observed that though extra RNA is lethal to cells, addition of dNTPs can rescue the cells. Furthermore, the dNTP-DPase competes with DNA polymerase for dNTPs. It was found that when the dNTP level in cell was relatively low, the dNTP-DPase activity shut down cellular DNA synthesis by hydrolyzing dNTPs. However, when the dNTP level in cell was relatively high, cellular DNA synthesis was not affected. The described findings at the molecular level indicate that DNA polymerases have multiple functions in cells and that RNA can interfere with and regulate cellular DNA synthesis and polymerase activity.

A. Results

1. DNA Polymerase in the Presence of RNA can Function as Deoxyribonucleoside Triphosphate Diphosphatase dNTPs were incubated in the presence of RNA and/or DNA polymerases. It was discovered that dNTP was hydrolyzed when only both RNA and DNA polymerase were present. The overall reaction scheme of the dNTP hydrolysis by the RNA-dependent dNTP-DPase activity of DNA polymerases is as follows:

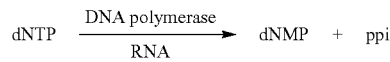

Single-stranded RNA as short as 6 nucleotides can still assist the dNTP hydrolysis. RNA can transform *E. coli* DNA polymerase I (DNA pol. I) into the dNTP-DPase, which hydrolyzes dNTPs into dNMPs and pyrophosphate (ppi), under DNA polymerization conditions. dATP (or dCTP) was not hydrolyzed in the presence of DNA polymerase I or RNA alone. However, the presence of both caused the hydrolysis of dATP (or dCTP) into dAMP (or dCMP). Excitingly, it was found that Klenow (the large fragment of DNA pol. I, without the 5'-3' exonuclease activity) and Klenow mutant (3'-5' exo-, without the 3'-5' exonuclease activity) have also the RNA-dependent dNTP-DPase activity. The RNA-dependent dNTP-DPase activities of these three enzymes indicate that the DNA polymerase itself, rather than the 5'-3' and 3'-5' exonuclease activities, is primarily responsible for the dNTP-DPase activity. Thus, the polymerase active site is likely where dNTPs are hydrolyzed. Mass spectrometry analysis of the dATP-hydrolyzed product confirmed its identity as dAMP.

Hydrolysis of $\alpha$-$^{32}$P-dATP by Klenow DNA polymerase (50 nM, final) was assessed in the presence of various short RNAs (200 nM each, final). The different assays were conducted with: cold dATP; co-spot of cold dATP and $^{32}$P-$\alpha$-dATP; $^{32}$P-$\alpha$-dATP; $^{32}$P-$\alpha$-dATP and Klenow DNA polymerase; $^{32}$P-$\alpha$-dATP and 6-mer RNA; $^{32}$P-$\alpha$-dATP and Klenow DNA polymerase and 6-mer RNA; $^{32}$P-$\alpha$-dATP and various RNAs (TR-RNA (12 nt), TC-RNA (12 nt; TC-RNA complementary to TR-RNA), TR-RNA/TC-RNA duplex, 18-mer-RNA, and 24-mer RNA); $^{32}$P-$\alpha$-dATP, Klenow DNA polymerase, and various RNAs (TR-RNA (12 nt), TC-RNA (12 nt; TC-RNA complementary to TR-RNA), TR-RNA/TC-RNA duplex, 18-mer-RNA, and 24-mer RNA); and cold dAMP. Hydrolysis of $\alpha$-$^{32}$P-dCTP by *E. coli* DNA polymerase I, Klenow, and Klenow (3'-5' exo-) in the presence of RNA (*E. coli* or yeast total RNA) was also assessed. Hydrolysis of $\alpha$-$^{32}$P-dATP by DNA pol. I, Klenow, and Klenow (3'-5' exo-) was also assessed.

2. NTPs are Inhibitors of the dNTP Hydrolysis, while dNTP is Hydrolyzed to Give dNMP and Pyrophosphate The hydrolysis of dATP by the dNTP-DPase activity was inhibited by both ATP and CTP, and ATP was not hydrolyzed by the dNTP-DPase. Likewise, the presence of ATP or CTP can inhibit the hydrolysis of dCTP. The inhibition of the RNA-dependent dNTP-DPase activity on dNTP hydrolysis is probably due to the NTP competition for the dNTP-DPase active site. Moreover, the formation of pyrophosphate in the reaction of the dNTP hydrolysis by the dNTP-DPase was demonstrated. The product formed by hydrolyzing $\gamma$-$^{32}$P-dATP with the RNA-dependent dNTP-DPase can be quantitatively degraded to inorganic phosphate with pyrophosphatase, thereby confirming the formation of pyrophosphate.

Formation of pyrophosphate from the hydrolysis of γ-$^{32}$P-dATP by *E. coli* DNA polymerase I in the presence of cellular RNA was assessed. The different assays were conducted in the following forms: heating γ-$^{32}$P-ATP in 10 mM NaOH, which produced $^{32}$P-lable pyrophosphate and monophosphate; heating γ-$^{32}$P-ATP in 10 mM NaOH and then digested with inorganic pyrophosphatase, where the formed pyrophosphate was converted into monophosphate; γ-ATP incubated with the inorganic pyrophosphatase (no reaction); γ-ATP incubated with DNA pol. I and RNA (no reaction), indicating that NTP is not the dNTP-DPase substrate; γ-$^{32}$P-dATP was incubated with DNA pol. I and RNA, where γ-$^{32}$P-dATP was hydrolyzed into dAMP and $^{32}$P-pyrophosphate; γ-$^{32}$P-dATP was incubated with DNA pol. I and RNA and then digested with pyrophosphatase, which converted the formed $^{32}$P-pyrophosphate into monophosphate; with γ-$^{32}$P-ATP; and with γ-$^{32}$P-dATP.

3. Arbitral RNA Binds to DNA Polymerase and Transforms it into the dNTP-Diphosphatase It was also demonstrated that DNA polymerase is capable of binding to arbitral RNA by a gel-shift assay using *E. coli* DNA polymerase I and a transcribed $^{32}$P-labeled-RNA (69 nt.). The binding result of DNA polymerase and RNA is consistent with the literature reports, where DNA polymerase I and Klenow can bind to ssDNA, dsDNA, and DNA primer-template complex (Freemont et al., 1988; Wowor et al., 2010). Specific binding between DNA polymerase and RNA was also reported in literature (Pavlov & Karam, 1994). Furthermore, it was demonstrated experimentally that cellular RNAs from different sources can stimulate this RNA-dependent dNTP-DPase activity. For instance, both human and *E. coli* total RNAs are able to stimulate the dNTP-DPase activity of Klenow DNA polymerase. This was accomplished by assessing hydrolysis of α-$^{32}$P-dCTP by Klenow in the presence of an arbitral RNA (RNA-1: human total RNA; RNA-2: *E. coli* total RNA).

4. DNA Polymerases Generally have the dNTP-DPase Activity in the Presence of RNA To examine whether the RNA-dependent dNTP hydrolysis can be generally observed with many DNA polymerases, several other DNA polymerases were investigated. Surprisingly, the DNA polymerases of A, B, C, and X families have displayed the similar dNTP-DPase activity. This was shown via analysis of hydrolysis of α-$^{32}$P-dATP (alpha-dATP) by *E. coli* DNA polymerase I (A family polymerase), T7 DNA polymerase (A family), and T4 DNA polymerase (B family) and of hydrolysis of α-$^{32}$P-dATP by human DNA polymerase β (Pol. β; X family) and *E. coli* DNA polymerase III (α-subunit; Pol. III; C family).

5. RNA can Efficiently Inhibit In Vitro DNA Polymerization when dNTP Concentrations are Relatively Low Since the RNA-dependent dNTP-DPase activity of DNA polymerase hydrolyzes dNTPs, it was realized that RNA may directly affect DNA polymerization, especially when the dNTP concentrations are low. Thus, RNA was added into a DNA polymerization reaction, where DNA polymerase, dNTPs, a template and a primer were present. In the absence of RNA, the DNA polymerization proceeded normally at a relatively low dNTP level (such as 3 µM each). However, in the presence of RNA, at the same dNTP concentrations, the DNA synthesis was disrupted. The dNTP concentrations needed for 50% DNA synthesis in the absence and presence of RNA were 1.8 and 6.7 µM, respectively (FIG. 1). The assays also revealed that when the dNTP concentrations were relatively high (such as 10 µM), the presence of RNA didn't significantly affect DNA synthesis (FIG. 1). Furthermore, it was discovered that when the RNA quantity was low, DNA polymerase reaction was not significantly affected. When the RNA concentration increased, however, significant decrease of the DNA synthesis was observed and even the complete shutdown of DNA polymerization, when the dNTP concentrations were relatively low (such as 3.5 µM). These observations indicate that RNA can directly interfere with DNA polymerization in vitro when the dNTP level is relatively low.

Synthesis of DNA, in the absence and presence of RNA, with various dNTP concentrations was assessed. The dNTP concentrations were: 0 nM, 100, 250, 500, 750 nM, 1 µM, 3, 10, 30, and 100 µM, for each dNTP. Inhibition of DNA polymerization via the dNTP hydrolysis was also assessed in the presence of various amounts of RNA. DNA template (55-mer, 200 nM) was annealed with the 5'-$^{32}$P-labeled primer (21-mer, 20 nM), and the reactions [containing DNA pol. I, dNTPs (3.5 µM each), and the increasing amounts of *E. coli* total RNA] were incubated for 30 min. The RNA amounts were: 0, 5, 25, 50, 100, 150, 200, 250, 300, 350, and 400 ng/µL of RNA.

6. Extra RNA Inhibits DNA Synthesis and Causes Cell Death, while Additional dNTPs and NTPs Rescue Cells Furthermore, since the RNA-dependent dNTP-DPase activity of DNA polymerases can affect in vitro DNA polymerization, it was realized that the presence of extra cellular RNA may affect cell survival and death (two extreme phenotypes). Though DNA polymerase is ubiquitous throughout the cell cycle, extra DNA polymerase may also be introduced into cells. In order to perform the experiments where exogenous DNA polymerase and cellular RNA can be delivered into the cells, competent cells were used, which allow passive diffusion of RNA and DNA polymerase. Similarly, the cellular dNTP level was easily controlled by simply adding dNTPs into the cell culture. Thus, chemically competent *E. coli* cells prepared by the CaCl$_2$ treatment were used, which also allow permeation of plasmids. The rationale of the experiments was that by delivering extra DNA polymerase and cellular RNA into the competent cells, the dNTP-DPase could form in cells in order to reduce the cellular dNTP level, thereby interfering the cellular DNA synthesis and creating phenotypes for observation (i.e., cell growth inhibition and death). It was realized that adding only relatively low quantity of DNA polymerase or RNA into the cell culture would not significantly influence cell growth. On the contrary, it was realized that significant growth inhibition and cell death would be observed when both DNA polymerase and cellular RNA are added simultaneously into the cell culture, even if their individual quantity is relatively low. It was also realized that if the cellular dNTPs are replenished by delivering additional dNTPs into the cells to compensate for the dNTPs depleted by the dNTP-DPase, the cells should be able to carry out DNA synthesis and survive normally. Furthermore, to monitor the delivery of extra DNA polymerase, RNA and/or dNTPs into cells, the competent cells were also simultaneously transformed using the plasmids with an antibiotics-resistant marker, which allowed the cells to grow in the presence of the corresponding antibiotics. During the cell growth, both genomic and plasmid DNAs (herein referred as cellular DNA) would be synthesized in cells.

Therefore, in the competent cell cultures, the plasmids, dNTPs, NTPs, cellular RNA and/or polymerases were included as additives in various combinations. Subsequently, the competent cells with the additives were heat-shocked to allow the transformation and permeation, followed by the cell culture incubation and agar plating. The synergistic effect of DNA polymerase and RNA on inhibition of cellular DNA synthesis was investigated by assaying the effect of DNA polymerase, RNA, and dNTPs added to cells. The additives were added individually (or combined) to the competent cells in each tube. After the heat-shock, the cells in each tube were incubated at 37° C. for 10 min, followed by addition of $\alpha$-$^{32}$P-dATP and incubation for 0, 5, 10, 20 and 30 min at 37° C. The additives in different assays were, for each time point: water, RNA (50 ng/µL), DNA polymerase (50 nM), and RNA (50 ng/µL) plus DNA polymerase (50 nM). On each plate, the additives to each competent cell tube were: $H_2O$; RNA; E. coli DNA polymerase I; dNTPs (10 µM each); RNA and Pol. I; RNA, Pol. I and dNTPs; RNA, Pol. I, and NTPs (10 µM each); and RNA, Pol. I, dNTPs, and NTPs. In the experiments, water was used as a control for each additive.

The experiments confirmed the realizations regarding control of DNA polymerase and DNA synthesis. The experimental results are that (I) at their relatively low quantities, adding DNA polymerase or cellular RNA alone doesn't significantly inhibit the cellular DNA synthesis, compared to the control experiment, where water was used as the additive. The DNA synthesis was monitored by the radioactive tracing, using $\alpha$-$^{32}$P-dATP, which was included in the cell culture as a dATP additive. The $\alpha$-$^{32}$P-dATP radioactivity was incorporated into cellular DNA when the cells survived and grew. Finally, after lysing the cells by heating, the cellular DNA was analyzed by polyacrylamide gel electrophoresis. When the cells are not growing or dead, cellular DNA is not synthesized, thus no radioactive DNA will be detected on film by autoradiography. Since 6% PAGE gel was used, DNA sequences over 800 nt. were not resolved, while shorter DNAs were visible on X-ray film as the smears. (II) Even at their relatively low quantities, it was discovered that adding both DNA polymerase and RNA did significantly inhibit the cellular DNA synthesis, indicating formation of the dNTP-DPase, which hydrolyzes dNTPs and directly inhibits cellular DNA synthesis. The same phenomenon was also observed at the cell colony level. (III) Even at their relatively low quantities, it was found that DNA polymerase or RNA alone didn't significantly inhibit the cell growth, compared to the control experiment, where water was used as the additive. However, when relatively-high quantity of RNA was added into the culture, the cellular RNA (final concentration: 200 ng/µL) inhibited cellular DNA synthesis and caused cell death, probably because of the assistance of endogenous DNA polymerases. Interestingly, addition of dNTPs into the cell culture (final concentration: 10 µA each dNTP) rescued both DNA synthesis and cells from the RNA lethal effect. (IV) Even at their relatively low quantities, it was discovered that adding both DNA polymerase and RNA did significantly inhibit the cell growth. Consistent with the pre-experiment realization and rationale that additional dNTPs can replenish the cellular dNTPs consumed by the dNTP-DPase (see FIG. 2), the added dNTPs in the culture should rescue the cells. Thus, extra dNTPs were included with DNA polymerase and RNA, and it was found that (V) by replenishing the consumed dNTPs, the added dNTPs can reverse the killing effect of addition of both DNA polymerase and cellular RNA. Similarly, according to the rationale, additional NTPs should inhibit the dNTP-DPase activity, thereby rescuing the cells. Therefore, NTPs were added together with DNA polymerase and RNA, and revealed that (VI) NTPs can indeed inhibit the toxic effect of the dNTP-DPase activity and rescue the cells (see FIG. 2). In addition, when total cellular RNAs of yeast and human were used for examining the cell survival and death, the same results were obtained.

B. Discussion

Figure 2:
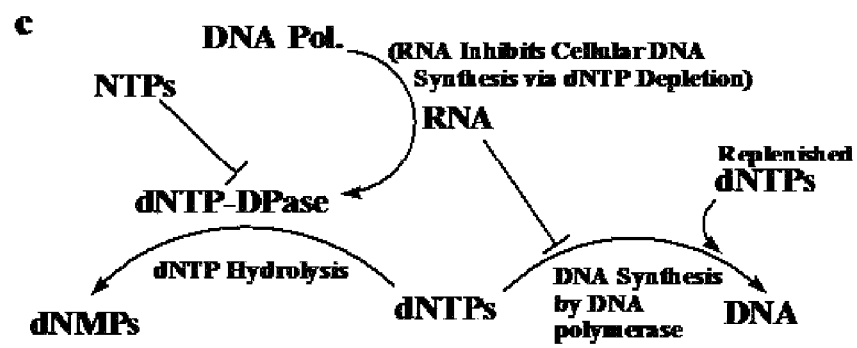
FIG. 2 is a diagram showing the mechanism of inhibition of cellular DNA synthesis and cell growth by exogenous DNA polymerase and cellular RNA.

This study indicates that the dNTP-DPase activity was low and only a part of DNA polymerases was transformed into the dNTP-DPase in the presence of RNA (FIG. 1). To simplify the qualitative analysis, the concentration of dNTPs needed for reaching 50%-yield inhibition of the maximal full-length DNA synthesis as the dNTP half concentration (dNTP-$C_{50}$) is referenced. In these in vitro experiments, the dNTP-$C_{50}$ values in the absence and presence of RNA are 1.8 and 6.7 µA, respectively. In the absence of RNA, DNA polymerase synthesizes the full-length DNA efficiently even at a low dNTP concentration (3 µA each dNTP; FIG. 2). In the presence of RNA, when the dNTP concentration is low (such as 3 µA each), the hydrolyzed dNTPs formed by the dNTP-DPase are relatively significant, thereby interfering with the DNA polymerization. However, due to the low activity of the dNTP-DPase, when the dNTP concentration is higher (such as 10 µM), the dNTPs hydrolyzed by the dNTP-DPase are relatively insignificant, thereby not interfering with the DNA polymerization.

In order to demonstrate the in vivo interference of RNA on DNA synthesis in cells, experiments were performed with the competent cells and with the cellular dNTP level kept low. The experimental results indicate that DNA synthesis in cells can be interfered with by the RNA level (FIG. 2), especially when the dNTP level is low. During the cell growth phase where a large quantity of cellular RNA is transcribed and the dNTP level is low, this RNA-dependent dNTP-PDase activity of DNA polymerase may efficiently suppress the non-programmed cellular DNA synthesis to maintain the genome integrity. Since the dNTP level plays an important role in regulating cellular DNA synthesis, this RNA-dependent mechanism is consistent with the regulation mechanism of the availability and level of the DNA precursors (dNTPs) in order to control DNA polymerization (Ji & Mathews, 1991; Chabes & Stillman, 2007; Rampazzo et al., 2010; Gon et al., 2011; Niida et al., 2011). In contrast, during the S phase of the cell cycle where the dNTP level is high, this RNA interference mechanism can no longer interfere with DNA synthesis.

The in vitro observation of the RNA interference with DNA polymerase and synthesis is consistent with the in vivo observation of the RNA-dependent inhibition of the cellular DNA synthesis. The dNTP level plays an essential role in mediating the RNA interference of DNA synthesis both in vitro and in vivo. Since RNA is ubiquitous throughout all phases of the cell cycle, the close link between RNA and dNTP level provides a suppression mechanism for non-programed DNA synthesis in the cell growth G phase, where the RNA quantity is relatively high and the dNTP level is relatively low.

Moreover, the structural analysis (FIG. 3) is consistent with the experimental observations on the dNTP hydrolysis by the RNA-dependent dNTP-DPase activity of DNA polymerase. A model structure of the dATP hydrolysis by the dNTP-DPase has also been established on the basis of the ddATP binding to the active site of Bacillus stearothermophilus DNA polymerase in the crystal structure (PDB ID: 3EZ5) (Golosov et al., 2010). The model structure of the dATP hydrolysis by the dNTP-DPase reveals that only subtle changes (e.g., the slight shifts of the dATP sugar pucker and the attacking water) are required (FIG. 3B) for DNA polymerase-incoming dATP complex to switch from the mode of the dATP binding and polymerization to the mode of the dATP hydrolysis. This structural analysis is also consistent with the DNA polymerase transformation into the diphosphatase upon a slight alteration in the conformation. Furthermore, the model structure was compared with the structure of inosine triphosphate pyrophosphatase (or diphosphatase, or ITP-DPase) complexed with ITP (Savchenko et al., 2007) (PDB ID: 2Q16; FIGS. 3A and 3B). This revealed that the dATP-DPase model structure and the ITP-DPase structure share striking similarities in their triphosphate hydrolysis reactions, including the two-metal-catalytic mechanism, the cation-assisted water activation, the hydrophobic pocket for the binding of these two nucleobases of dATP and dITP, and the enhanced binding affinity through the aromatic stacking interaction.

It was demonstrated that the active site of DNA polymerase is involved in the dNTP hydrolysis, which is consistent with the structural analysis (FIG. 3). Interestingly, from the chemical point of view, the dNTP hydrolysis and polymerization reactions by DNA polymerase are closely related (FIG. 3c). The hydrolysis happens when the activated water molecule (a nucleophile) attacks the alpha position of dNTPs (Pathway I), while the DNA polymerization occurs when the activated 3'-hydroly group (a nucleophile) attacks the alpha position of dNTPs (Pathway II). Pyrophosphate is released as the leaving group and by-product in these two similar reactions (or processes). The observations here indicate that the binding of RNA may slightly alter the DNA polymerase conformation, and the polymerase active site is subsequently reorganized into the alternative conformation that is capable of catalyzing the dNTP hydrolysis. Thus, a subtle conformation change in the polymerase local environment may shift the reaction from the dNTP polymerization to hydrolysis, potentially enhancing the polymerase editing ability.

The results demonstrated that RNA can bind and transform DNA polymerase into deoxyribonucleoside triphosphate diphosphatase (dNTP-DPase), which selectively hydrolyzes dNTPs into dNMPs and pyrophosphate. The structural analysis indicates that the small conformation changes can facilitate the transformation. It was found that NTPs are not the dNTP-DPase substrates, but inhibitors. Moreover, it was observed both in vitro and in vivo that when the dNTP concentrations are relatively low, in the presence of RNA, the dNTP-DPase activity can deplete dNTPs in DNA synthesis, thereby negatively influencing DNA polymerization. However, when dNTP concentrations are relatively high, the DNA synthesis is not affected. Furthermore, it was observed that when the dNTP level is low, high RNA level suppresses cellular DNA synthesis and cell proliferation, while additional dNTPs and/or NTPs can rescue the cells. It was also found that DNA polymerases of A, B, C, and X families generally have the similar dNTP-DPase activity. The findings at the molecular level indicate that in cells, DNA polymerases are of multiple-functions and cellular RNA regulates non-programed DNA synthesis via a feedback mechanism, such as in the G phase of cell cycle.

C. Materials and Methods dNTP Hydrolysis by the RNA-Dependent dNTP-DPase of DNA Polymerase.

A reaction solution (5 µL) containing various individual DNA polymerases, RNA (short RNAs and *E. coli*, yeast or human total RNAs, or other RNAs), 0.1 µL of α-$^{32}$P-dATP (or γ-$^{32}$P-dATP, α-$^{32}$P-dCTP, α-$^{32}$P-CTP, or α-$^{32}$P-ATP), buffer (final: 10 mM Tris-HCl, 10 mM MgCl$_2$, 50 mM NaCl, 1 mM DTT, pH 7.9), and water was incubated in water bath for 30 min to 1 hr. at 37° C. The reaction was then analyzed by thin layer chromatography (TLC). In each negative control experiment, RNA or DNA polymerase was replaced with water.

Thin Layer Chromatography (TLC) Analysis of the dNTP Hydrolysis by the dNTP-DPase.

TLC plates of 100 micron layer thickness were purchased from Micron Technology, USA. 0.2 µL (or 0.5 µL) reaction solutions were spotted on the TLC plate with corresponding controls. The bottom of the plate was submerged in an eluent (isopropyl alcohol:ammonium hydroxide:water=5:4:2 or 6:3:1), keeping the loading spots one inch above the eluent. The chromatographic plates were allowed to run for 30-45 minutes at room temperature in an air-tight tank.

Gel-Shift Assay of DNA Polymerase-RNA Binding.

In order to demonstrate RNA binding to DNA polymerase, gel-shift assay was performed. A mixture (5 µL) containing bodily $^{32}$P-labeled RNA 69-mer (50 nM, final), DNA polymerase I (0, 20, 40, 60, or 80 nM), and binding buffer (final: 10 mM KCl, 1 mM DTT, 5% glycerol, pH 7.0) was incubated at room temperature for 30 minutes and then placed at 4° C. overnight. The binding solutions were mixed with the gel loading dye (final: 10 mM KCl, 1 mM DTT, 5% glycerol, 0.001% xylene blue w/v) and then loaded on 10% non-denaturing polyacrylamide gel in the running buffer (5 mM Tris-HCl, 10 mM EDTA, and pH 7.5). The gel was pre-run for 1 hour at 250 volts. After loading the samples, the gel was run with a constant voltage (250 volts) for one hour; all operations were performed in 4° C. cold room. The gel was fixed with 7% acetic acid (in methanol), dried, and scanned. The radioactive bands were quantified by phosphorimager using image quantifying software. Data from the gel-shift assays were plotted with Sigma Plot by placing enzyme concentration as X-axis and DNA polymerase-RNA complex (bound fraction) as Y-axis. Dissociation constant was determined from the binding curves.

Inhibition of In Vitro DNA Polymerization by RNA.

A reaction (5 µL) containing 5'-$^{32}$P-labeled DNA primer 21.1 (1 µL, 100 nM; final: 20 nM), DNA template 55.1 (0.5 µL, 2 µM; final 200 nM), 0.5 µL 10× buffer (final: 10 mM Tris-HCl, 10 mM MgCl$_2$, 50 mM NaCl, 1 mM DTT, pH 7.9), 0.8 µL dNTPs (final: 3.5 µM each), 0.2 µL DNA polymerase I (50 nM, final) and 2 µL TR-RNA (12 nt; 0, 25, 50, 75, 100, 150, 200, 300, 400 nM, final) or 2 µL *E. coli* total RNA (0, 5, 25, 50, 100, 150, 200, 250, 300, 350, or 400 ng/µL, final) was incubated at 37° C. for 30 min. In the negative control reaction, water was added to replace the RNA. After the incubation, the reactions were quenched by adding the gel loading dye (containing 7 M urea and 1 mM EDTA) and immediately placing on dry ice. The reactions were analyzed by denaturing polyacrylamide gel (15% w/v; acrylamide:bisacrylamide=19:1) and autoradiography. The product bands were quantified by phosphorimager using image quantification software.

Interference of Cellular DNA Synthesis by the RNA-Dependent dNTP-DPase when the dNTP Level is Low.

To Eppendorf tube (1.5 mL each), chemically competent *E. coli* cells (10 µL; BL21, Invitrogen), pUC19 plasmid (0.5 pmol), and different additives (or combinations) were added and swirled gently. DNA polymerase and/or RNA at various quantities were added. After the transformations (including on ice for 5 min) and incubation at 37° C. for 10 min, SOC medium (50 µL) and α-$^{32}$P-dATP (1 µL) were added to each tube, which was swirled gently. After incubation at 37° C. for 20 min, each tube was centrifuged to recover the cell pellet. Each pellet was suspended completely in the Tris buffer (10 µL, 20 mM, pH 8.5), and the gel loading dye (10 µL) was added to each tube. The samples were then heated at 95° C. for 5 min to lyse the cells, and 10 µL of each sample was used to perform denaturing PAGE analysis (6% gel). The synthesized cellular DNAs were visualized by autoradiography.

Cell Growth Inhibition and Death by the RNA-Dependent dNTP-DPase when the dNTP Level is Low.

To Eppendorf tube (1.5 mL each), chemically competent E. coli cells (10 µL; BL21, Invitrogen), pUC19 plasmid (0.5 pmol), and different additives (or combinations discussed above) were added and swirled gently. Transformations were conducted by placing the tubes on ice for 30 minutes and heat-shocking at 42° C. for 1 min, followed by immediately placing them on ice for 5 min. To each tube, SOC medium (50 µL) was added, and each tube was shaken at 225 rpm for 30 min at 37° C. On each section of a LB-ampicillin plate, the bacterial culture (10 µL) from each tube was spread. The plates were incubated at 37° C. overnight, and E. coli colonies were observed visually next day.

Synthesis and Purification of Oligonucleotides:

```
6-mer RNA:
5'-UCGACA-3'

TR-RNA(12 nt):
                                        (SEQ ID NO: 1)
5'-AUCCGAGUCAGG-3';

TC-RNA(12 nt;TC-RNA complementary to TR-RNA):
                                        (SEQ ID NO: 2)
5'-CCUGACUCGGAU-3';

18-mer-RNA:
                                        (SEQ ID NO: 3)
5'-UCGACAUCGACA-UCGACA-3';

24-mer RNA:
                                        (SEQ ID NO: 4)
5'-UCGACAUCGACAUCGACAUCGACA-3';

RNA24.1:
                                        (SEQ ID NO: 5)
5'-AUGUGGAUUGGCGAUAAAAAACAA-3';

RNA-69mer:
                                        (SEQ ID NO: 6)
5'-rGGGAGCCCUGUCACCGGAUGUGCUUUCCGGUCUGAUG

AGUCCGU-GAGGACAAAACAGGGCUCCCGAAUU-3';

DNA template (55.1):
                                        (SEQ ID NO: 7)
5'-d(TGTACGTTTCGGCCTTTCGGCCTCATCAGGTTGCC

TATAGTGAGTCGTATTA CGC)-3';

DNA primer (21.1):
                                        (SEQ ID NO: 8)
5'-d(GCGTAATACGACTCACTATAG)-3';
```

Other RNA samples: human total RNA, yeast total RNA, E. coli total RNA, ladder RNAs (0.2, 0.5, 1.0, 2.0, 4.0, and 6.0 kb).

DNA primer (21.1), DNA template (55.1), and RNA24.1 oligonucleotides were synthesized by solid phase methods. Chemical synthesis was performed on a 1.0 µmolscale using an ABI392 DNA/RNA Synthesizer. After synthesis DNA was cleaved from the beads by reacting overnight with aqueous ammonium hydroxide at 55° C. Deprotection of RNA was performed as described (Carrasco et al., 2004). Products were separated by 12 or 19% urea-polyacrylamide gel (7 M urea, 89 mM Tris-HCl, 89 mM boric acid and 2 mM EDTA, gel size 40 cm×35 cm×1.6 mm) Gels were pre-run for 1 hr at 700 volts without cooling to keep the plate warm. After mixed with the loading dye, sample was loaded on the gel and run for 2-4 hours. After electrophoresis, the desired bands of the oligonucleotides were cut from the gel, which was placed on the top of a TLC plate and visualized under UV light. The excised gel was crushed in 1.5 mL Eppendorf tube, and 3 volumes of water were added. Each tube was placed in a rotator for overnight soaking at room temperature. Oligonucleotides were recovered by ethanol precipitation, and their concentrations were measured by UV spectrophotometer.

In Vitro Transcription of RNAs.

RNA-69mer was transcribed from the plasmid pHHRZ carrying the RNA gene with T7RNAP promoter, and the in vitro transcription reaction was performed by using Ampliscribe™ Transcription Kit (Epicentre). A typical transcription reaction (20 µL) consists of 50 ng plasmid (1 µL), 4 µL 5× buffer (200 mM Tris-HCl pH 7.5, 30 mM $MgCl_2$, 50 mM NaCl, 10 mM DTT, and 10 mM spermidine), 10 mM each NTP (8 µL total), 0.05 U/µL T7 RNA polymerase (1 µL), and RNase free water (6 µL). The reaction was incubated at 37° C. for 1 hr. and RNA-69mer was recovered by spinning column purification and ethanol precipitation.

Extraction of Total Cellular RNAs.

Total cellular RNA from E. coli and yeast were extracted using RNA purification kit (Epicentre). Briefly, an overnight culture (0.5 mL) of E. coli (0.5-3×10$^6$ cells) or yeast was lysed with the tissue-and-cell lysis solution (300 µL) containing proteinase K by incubating at 65° C. for 10 min. MPC protein precipitation reagent (150 µL) was added to the lysed solution and centrifuged for 10 minutes (≥10,000×g), and the supernatant was collected. Total nucleic acid from supernatant was recovered by precipitation with 70% isopropanol. Contaminated DNA was removed by incubating nucleic acid with 200 µL DNase I solution for 10 minutes at 37° C. DNA-free RNA was recovered by centrifugation with 70% isopropanol at 4° C. for 10 minutes (≥10,000×g). Total RNA from human prostate cancer cells and RNA ladder (0.2, 0.5, 1.0, 2.0, 4.0, and 6.0 kb, 150 ng/µL) were purchased from Ambion Technologies (USA).

dNTP Hydrolysis Assay by the RNA-Dependent dNTP-DPase of DNA Polymerases.

A reaction solution (5 µL) containing various individual DNA polymerases, cellular RNA (final concentration: 200 ng/µL; E. coli, yeast or human total RNAs, and other RNAs), 0.1 µL of α-$^{32}$P-dATP (or γ-$^{32}$P-dATP, α-$^{32}$P-dCTP, α-$^{32}$P-CTP, or α-$^{32}$P-ATP), buffer (final: 10 mM Tris-HCl, 10 mM $MgCl_2$, 50 mM NaCl, 1 mM DTT, pH 7.9) and water was incubated in water bath for 30 min to 1 hr. at 37° C. The reaction was then analyzed by TLC (thin layer chromatography). In each negative control experiment, RNA or DNA polymerase was replaced with water. DNA polymerases [E. coli DNA polymerase I, Klenow, and Klenow (3'-5' exo-)] were purchased from New England Biolabs. Dpo4 was expressed in our laboratory by using the Dpo4-expressing plasmid kindly given by Dr. Roger Woodgate at National Institutes of Health, while the initial Dpo4 sample was kindly given by Dr. Zucai Suo (Ohio State University). Human DNA polymerase β and E. coli DNA polymerase III (α-subunit) were kindly given by Dr. Michael O'Donnell (Rockefeller University). Other polymerases were purchased from commercially sources.

Alkali Hydrolysis of Triphosphates.

γ-$^{32}$P-ATP was hydrolyzed by NaOH (14 µL total): γ-$^{32}$P-ATP (2 µL), NaOH (1.4 µL, 100 mM; final: 10 mM), and water (10.6 µL) were mixed and heated at 90° C. for 1 hr. The hydrolyzed products were used to serve as markers for TLC analysis.

Pyrophosphatase Reaction.

A reaction (5 µL) containing γ-$^{32}$P-dATP dNTP-DPase hydrolysis (2 µL), 0.5 µL buffer (final: 10 mM Tris-HCl, 10 mM MgCl$_2$, 50 mM NaCl, 1 mM DTT, pH 7.9), inorganic pyrophosphatase (0.25 µL; 0.05 unit; EC 3.6.1.1), and water (2.25 µL) was incubated at 37° C. for 15 min and analyzed by TLC.

Polynucleotide Kinase Reaction.

A reaction (10 µL) containing DNA primer 21.1 (1 µL from 1 µM stock), 10×PNK buffer (1 µL; 70 mM Tris-HCl, 10 mM MgCl$_2$, 5 mM DTT, pH 7.6, final), γ-$^{32}$P-ATP (0.5 µL, 3,000 Ci/mmol, 5 mCi/ml), T4 polynucleotide kinase (1 unit, 1 µL), and water (6.5 µL) was incubated in a water bath for 1 hr at 37° C. The reaction was then heated at 68° C. for 10 min to inactivate the enzyme. Ethanol precipitation was performed to recover $^{32}$P-labeled DNA by adding NaCl (1.1 µL, 3 M; final 0.3 M) and 100% ethyl alcohol (33.3 µL), followed by centrifugation (14,000 rpm). Supernatant was discarded. The pellet was washed 3 times with 70% ethanol, air-dried, and dissolved in H2O (10 µL).

Inhibition of In Vitro DNA Polymerization by RNA.

A reaction (5 µL) containing 5'-$^{32}$P-labeled DNA primer 21.1 (1 µL, 100 nM; final: 20 nM), DNA template 55.1 (0.5 µL, 2 µM; final 200 nM), 0.5 µL 10× buffer (final: 10 mM Tris-HCl, 10 mM MgCl$_2$, 50 mM NaCl, 1 mM DTT, pH 7.9), 0.8 µL dNTPs (final: 3.5 µM each), 0.2 µL DNA polymerase I (50 nM, final) and 2 µL TR-RNA (12 nt; 0, 25, 50, 75, 100, 150, 200, 300, 400 nM, final) or 2 µL E. coli total RNA (0, 5, 25, 50, 100, 150, 200, 250, 300, 350, and 400 ng/µL, final) was incubated at 37° C. for 30 min. In the negative control reaction, water was added to replace the cellular RNA. After the incubation, the reactions were quenched by adding the gel loading dye (containing 7 M urea and 1 mM EDTA) and immediately placing on dry ice. The reactions were analyzed by denaturing polyacrylamide gel (15% w/v; acrylamide:bisacrylamide=19:1) and autoradiography. The product bands were quantified by phosphorimager using image quantification software.

Thin Layer Chromatography (TLC) Analysis of dNTP Hydrolysis by the dNTP-DPase.

TLC plates of 100 micron layer thickness were purchased from Micron Technology, USA. 0.2 µL (or 0.5 µL) reaction solutions were spotted on the TLC plate with corresponding controls. The bottom of the plate was submerged in an eluent (isopropyl alcohol:ammonium hydroxide:water=5:4:2 or 6:3:1), keeping the loading spots one inch above the eluent. The chromatographic plates were allowed to run for 30-45 minutes at room temperature in an air-tight tank.

FPLC and MS Analyses of the Product of dNTP Hydrolysis.

50 µL solution was removed from a reaction cocktail (150 µL) containing E. coli total RNA (200 ng/mL, final), 100 µM dATP (final), and reaction buffer (final: 10 mM Tris-HCl, 10 mM MgCl2, 50 mM NaCl, 1 mM DTT, pH 7.9) before addition of DNA polymerase I. This solution was regarded as "0 minute" reaction. The dATP hydrolysis reaction was initiated by adding DNA polymerase I (100 nM, final) to the rest reaction solution (100 µL) and by incubating in 37° C. water bath. Aliquots (50 µL each) were removed at 30 min and 1 hr, which were referred as "30 min" and "1 hr" reaction, respectively. All three reaction solutions were analyzed by anion exchange column (HiTrap Q HP, 5 mL, Amersham bioscience) and the product was purified by FPLC. In more details, the column was washed with 10 column volumes (CV) of buffer B (final: 10 mM sodium phosphate, pH 7.8, 1 M NaCl) to remove impurities, and the column was then equilibrated by washing with 10 CV of buffer A (10 mM sodium phosphate, pH 7.8). After loading the sample onto FPLC, the column was eluted with 5 CV of buffer A, followed by applying buffer B gradient (0-100%) over 60 mL with a flow rate 1 mL/min and monitored by UV absorption at 259 nm. The retention time of dATP, dADP or dAMP was determined by analyzing each reaction solution separately, followed by co-injection of it with dATP, dADP or dAMP. The dATP hydrolysis product was purified by FPLC and HPLC (for desalting), and the product was finally analyzed by MS to confirmed it as dAMP {Mol. Formula: $C_{10}H_{14}N_5O_6P$; [M-H$^+$]$^-$: 330 (calculated: 330)}.

Gel-Shift Assay of DNA Polymerase-RNA Binding.

In order to demonstrate RNA binding to DNA polymerase, gel-shift assay was performed. A mixture (5 µL) containing bodily $^{32}$P-labeled RNA 69-mer (50 nM, final), DNA polymerase I (0, 20, 40, 60, or 80 nM), and binding buffer (final: 10 mM KCl, 1 mM DTT, 5% glycerol, pH 7.0) was incubated at room temperature for 30 minutes and then placed at 4° C. overnight. The binding solutions were mixed with the gel loading dye (final: 10 mM KCl, 1 mM DTT, 5% glycerol, 0.001% xylene blue w/v) and then loaded on 10% non-denaturing polyacrylamide gel in the running buffer (5 mM Tris-HCl, 10 mMEDTA, and pH 7.5). The gel was pre-run for 1 hr at 250 volts. After loading the samples, the gel was run with a constant voltage (250 volts) for one hour, all operations were performed in 4° C. cold room. The gel was fixed with 7% acetic acid (in methanol), dried, and scanned. The radioactive bands were quantified by phosphorimager using image quantifying software. Data from the gel-shift assays were plotted with Sigma Plot by placing enzyme concentration as X-axis and DNA polymerase-RNA complex (bound fraction) as Y-axis. Dissociation constant was determined from the binding curves.

Interference of Cellular DNA Synthesis by the RNA-Dependent dNTP-DPase when the dNTP Level is Low.

Growth of E. coli (BL21; from Invitrogen) with cellular RNA (E. coli total RNA) and/or DNA polymerase I as well as their cellular DNA synthesis were examined Cellular RNA (50 ng/µL, final) and/or DNA polymerase I (50 nM, final) were added to the competent cell suspension containing the pUC19 plasmid (0.5 pmol) before transformation. Transformations were conducted by placing the tubes on ice for 30 minutes and heat-shocking at 42° C. for 1 min, followed by immediately placing them on ice for 5 min. After the transformations (10 µL in each tube) and incubation at 37° C. for 10 min, SOC medium (50 µL) and α-$^{32}$P-dATP (2 µL, total) were added, and each tube was swirled gently. Aliquot (10 µL) from each culture was removed and immediate frozen at −80° C. These samples were referred to zero min, and the rest culture was incubated at 37° C. by shaking at 225 rpm. Aliquot (10 µL) of each culture was removed at 5, 10, 20, and 30 min and immediately frozen at −80° C. These samples were finally centrifuged at high speed for 10 min, and pellets were recovered. Each pellet was suspended completely in Tris buffer (10 µL, 20 mM, pH 8.5), and the gel loading dye (10 µL) was added to each tube. The samples were then heated at 95° C. for 5 min to lyse the cells, and 10 µL of each sample was used to perform denaturing PAGE analysis (6% gel, running for 1 hr at 700 volts). The synthesized cellular DNAs were visualized by autoradiography and quantified by phosphorimager using image quantification software.

When both cellular RNA and polymerase were used, lower dosage of each can lead to cell killing. Clearly, DNA polymerase and RNA have the synergistic effect in cell death, which was confirmed by analyzing cellular DNA synthesis (Figure S2). The combination of DNA polymerase and cellular RNA at lower quantity can almost completely inhibit DNA synthesis. This is most likely the mechanism of the cell death caused by DNA polymerase and cellular RNA, which result in the dNTP depletion of the competent cells.

Cell Growth Inhibition and Death by the RNA-Dependent dNTP-DPase when the dNTP Level is Low:

Chemically competent *E. coli* cells (Top 10) were purchased from Invitrogen. A vial (20 µL) of competent cells was mixed with 10 pmol pUC19 plasmid (4 µL; purchased from Invitrogen), and the mixture was distributed into 8 tubes (3 µL each). To these tubes, different combinations of water, cellular RNA (*E. coli*, yeast or human total RNA), DNA Polymerase I, dNTPs (final: 10 µM each), and/or NTPs (final: 10 µM each) were added. The final mixture volume in each tube was 5 µL. Each tube was kept on ice for 30 minutes and the cells were then heat-shocked for 45 seconds at 42° C. Put tubes back on ice for 2 minutes, and added LB (1 mL, without antibiotics). Incubated the tubes for 0.5 hour at 37° C. Cultures (50 µL each) were spread on a LB-ampicillin plate. Each plate was incubated at 37° C. overnight and *E. coli* colonies were observed visually the next day.

On the plates, total RNA samples from three different organisms: *E. coli*, yeast, and human were used. Bacteria grew normally in the presence of additional water, cellular RNA, Klenow or dNTPs alone. The competent cells did not survive when simultaneously adding both cellular RNA and DNA polymerase. However, cell growth was rescued by adding dNTPs and/or NTPs when extra RNA and DNA polymerase were added. The added dNTPs could have replenished the dNTPs hydrolyzed by the RNA-dependent dNTP-DPase activity of DNA polymerase, while added NTPs were able to efficiently inhibit the dNTP-DPase activity.

Analysis of the dNTP-DPase Model Structure:

The model study (FIG. 3) is consistent with the observations on the dNTP hydrolysis by the RNA-dependent dNTP-DPase activity of DNA polymerase. A dATP hydrolysis model was established on the basis of the ddATP binding to the active site of *Bacillus stearothermophilus* DNA polymerase in the crystal structure (PDBID: 3EZ5). The dATP hydrolysis model reveals that only subtle changes (e.g., the slight dATP rotation and the attacking water shift) are required (FIG. 3B) in the DNA polymerase to switch from the dATP binding and polymerizing state to the dATP-hydrolyzing state. This is consistent with the observation that DNA polymerase can also behave as a diphosphatase.

Furthermore, the model was compared with the structure of inosine triphosphate pyrophosphatase (or diphosphatase) complexed with ITP (PDBID: 2Q16; FIGS. 3A and 3B). It was found that the modeled dNTP-DPase and the triphosphate pyrophosphatase have shared the striking similarities in their triphosphate hydrolysis reactions, including the two-metal-catalytic mechanism, cation-assisted water activation, hydrophobic pocket for the nucleobase binding, and binding affinity via the aromatic stacking interaction.

REFERENCES

Agmon, 2009. The dimeric proto-ribosome: Structural details and possible implications on the origin of life. Int J Mol Sci 10:2921-2934.

Carrasco et al., 2004. Selenium derivatization and crystallization of DNA and RNA oligonucleotides for X-ray crystallography using multiple anomalous dispersion. Nucleic Acids Res 32:1638-1646.

Chabes and Stillman, 2007. Constitutively high dNTP concentration inhibits cell cycle progression and the DNA damage checkpoint in yeast *Saccharomyces cerevisiae*. Proc Natl Acad Sci USA 104:1183-1188.

Cheah et al., 2007. Control of alternative RNA splicing and gene expression by eukaryotic riboswitches. Nature 447:497-500.

Elledge and Davis, 1990. Two genes differentially regulated in the cell cycle and by DNA-damaging agents encode alternative regulatory subunits of ribonucleotide reductase. Genes Dev 4:740-751.

Fire et al., 1998. Potent and specific genetic interference by double-stranded RNA in *Caenorhabditis elegans*. Nature 391:806-811.

Fox et al., 2012. An exit cavity was crucial to the polymerase activity of the early ribosome. Astrobiology 12:57-60.

Freemont et al., 1988. Cocrystal structure of an editing complex of Klenow fragment with DNA. Proc Natl Acad Sci USA 85:8924-8928.

Gesteland et al., 2006. The RNA World: The Nature of Modern RNA Suggests a Prebiotic RNA, ed. 3, Cold Spring Harbor, N.Y.: Cold Spring Harbor Laboratory Press.

Golosov et al., 2010. The mechanism of the translocation step in DNA replication by DNA polymerase I: a computer simulation analysis. Structure 18:83-93.

Gon et al., 2011. Increase in dNTP pool size during the DNA damage response plays a key role in spontaneous and induced-mutagenesis in *Escherichia coli*. Proc Natl Acad Sci USA 108:19311-19316.

Guo et al., 2010. Mammalian microRNAs predominantly act to decrease target mRNA levels. Nature 466:835-840.

Harms et al., 2001. High resolution structure of the large ribosomal subunit from a mesophilic *eubacterium*. Cell 107:679-688.

Heo and Sung, 2011. Vernalization-mediated epigenetic silencing by a long intronic noncoding RNA. Science 331:76-79.

Ji and Mathews, 1991. Analysis of mutagenesis induced by a thermolabile T4 phage deoxycytidylate hydroxymethylase suggests localized deoxyribonucleotide pool imbalance. Mol Gen Genet 226:257-264.

Ma et al., 2005. Structural basis for 5'-end-specific recognition of guide RNA by the *A. fulgidus* Piwi protein. Nature 434:666-670.

Macrae et al., 2006. Structural basis for double-stranded RNA processing by Dicer. Science 311:195-198.

Mathews, 2006. DNA precursor metabolism and genomic stability. FASEB J 20:1300-1314.

Mathews and Ji, 1992. DNA precursor asymmetries, replication fidelity, and variable genome evolution. Bioessays 14:295-301.

Mello and Conte, 2004. Revealing the world of RNA interference. Nature 431:338-342.

Nagano et al., 2008. The Air noncoding RNA epigenetically silences transcription by targeting G9a to chromatin. Science 322:1717-1720.

Niida et al., 2011. Mechanisms of dNTP supply that play an essential role in maintaining genome integrity in eukaryotic cells. Cancer Sci 101:2505-2509.

Nishitani and Lygerou, 2002. Control of DNA replication licensing in a cell cycle. Genes Cells 7:523-534.

Nissen et al., 2000. The structural basis of ribosome activity in peptide bond synthesis. Science 289:920-930.

Paulsson and Chattoraj, 2006. Origin inactivation in bacterial DNA replication control. Mol Microbiol 61:9-15.

Pavlov and Karam, 1994. Binding specificity of T4 DNA polymerase to RNA. J Biol Chem 269:12968-12972.

Rampazzo et al., 2010. Regulation by degradation, a cellular defense against deoxyribonucleotide pool imbalances. Mutat Res 703:2-10.

Savchenko et al., 2007. Molecular basis of the antimutagenic activity of the house-cleaning inosine triphosphate pyrophosphatase RdgB from *Escherichia coli*. J Mol Biol 374:1091-1103.

Sudarsan et al., 2006. Tandem riboswitch architectures exhibit complex gene control functions. Science 314:300-304.

Wiedenheft et al., 2012. RNA-guided genetic silencing systems in bacteria and archaea. Nature 482:331-338.

Wowor et al., 2010. Thermodynamics of the DNA structural selectivity of the Pol I DNA polymerases from *Escherichia coli* and *Thermus aquaticus*. Biophys J 98:3015-3024.

Zhao et al., 1998. A suppressor of two essential checkpoint genes identifies a novel protein that negatively affects dNTP pools. Mol Cell 2:329-340.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a RNA" includes a plurality of such RNAs, reference to "the RNA" is a reference to one or more RNAs and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different RNAs does not indicate that the listed RNAs are obvious one to the other, nor is it an admission of equivalence or obviousness.

Every compound or component disclosed herein is intended to be and should be considered to be specifically disclosed herein. Further, every subgroup that can be identified within this disclosure is intended to be and should be considered to be specifically disclosed herein. As a result, it is specifically contemplated that any compound or component, or subgroup of compounds or components can be either specifically included for or excluded from use or included in or excluded from a list of compounds or components. For example, as one option, a group of RNAs is contemplated where each compound or component is as described herein but is not tRNA, siRNA, snRNA, mRNA or rRNA. As another example, a group of RNAs is contemplated where each RNA is as described herein and is not able to be translated. mRNA and siRNA can be independently and specifically included or excluded from the compounds or components and methods disclosed herein.

Those skilled in the art will recognize, or be able to ascertain using no more than routine experimentation, many equivalents to the specific embodiments of the method and compositions described herein. Such equivalents are intended to be encompassed by the following claims.

We claim:

1. A method of inhibiting DNA synthesis in a cell, the method comprising bringing into contact RNA and the cell such that the RNA enters the cell and binds to DNA polymerase in the cell such that DNA synthesis in the cell is inhibited, wherein the RNA has a sequence complexity of $1 \times 10^4$ or more.

2. The method of claim 1, wherein the cell is a cell in a subject.

3. The method of claim 2, wherein the cell is a cancer cell, wherein inhibition of DNA synthesis in the cell kills the cancer cell, or inhibits replication or growth of the cancer cell.

4. The method of claim 2, wherein the RNA is administered to the subject.

5. The method of claim 1, wherein the RNA is modified RNA.

6. The method of claim 1, wherein the RNA is comprised in a composition, wherein the composition further comprises a pharmaceutically acceptable carrier.

7. The method of claim 6, wherein the composition further comprises a targeting molecule, wherein the RNA is brought into contact with the cell by targeting the RNA to the cell via the targeting molecule.

8. The method of claim 7, wherein the targeting molecule is a tumor-targeting peptide selected from the group consisting of RGD, CAR, LyP-1, NGR, and RGR.

9. The method of claim 1, wherein the RNA consists essentially of sequences homologous to cellular RNAs inside the cell.

10. The method of claim 1, wherein the RNA does not include a substantial open reading frame, does not include functional translation control sequences or elements, or a combination thereof, whereby the RNA does not functionally encode a protein.

11. The method of claim 1, wherein inhibition of DNA synthesis in the cell inhibits growth of the cell.

12. The method of claim 1, wherein inhibition of DNA synthesis in the cell inhibits replication of the cell.

13. The method of claim 1, wherein inhibition of DNA synthesis in the cell kills the cell.

* * * * *